US011434290B2

(12) United States Patent
Davila

(10) Patent No.: US 11,434,290 B2
(45) Date of Patent: Sep. 6, 2022

(54) CHIMERIC ANTIGEN RECEPTORS WITH ENHANCED NFκB SIGNALING

(71) Applicant: H. Lee Moffitt Cancer Center and Research Institute, Inc., Tampa, FL (US)

(72) Inventor: Marco L. Davila, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 16/632,091

(22) PCT Filed: Sep. 11, 2018

(86) PCT No.: PCT/US2018/050417
§ 371 (c)(1),
(2) Date: Jan. 17, 2020

(87) PCT Pub. No.: WO2019/060174
PCT Pub. Date: Mar. 28, 2019

(65) Prior Publication Data
US 2020/0216534 A1 Jul. 9, 2020

Related U.S. Application Data

(60) Provisional application No. 62/666,385, filed on May 3, 2018, provisional application No. 62/666,381, filed on May 3, 2018, provisional application No. 62/640,153, filed on Mar. 8, 2018, provisional application No. 62/597,128, filed on Dec. 11, 2017, provisional application No. 62/516,815, filed on Sep. 22, 2017.

(51) Int. Cl.
*C07K 16/28* (2006.01)
*C07K 14/705* (2006.01)
*C12N 5/0783* (2010.01)

(52) U.S. Cl.
CPC .... *C07K 16/2803* (2013.01); *C07K 14/70521* (2013.01); *C12N 5/0638* (2013.01); *C07K 2317/622* (2013.01); *C07K 2319/02* (2013.01); *C07K 2319/03* (2013.01); *C07K 2319/33* (2013.01); *C07K 2319/70* (2013.01); *C12N 2501/515* (2013.01); *C12N 2510/00* (2013.01)

(58) Field of Classification Search
CPC ..... C07K 14/7051–70578; C07K 2319/00–03; C07K 2319/70
See application file for complete search history.

(56) References Cited

U.S. PATENT DOCUMENTS

| 10,800,833 | B2 * | 10/2020 | Jantz | C07K 14/7051 |
| 11,286,291 | B2 * | 3/2022 | Jantz | C07K 14/7051 |
| 2014/0328812 | A1 | 11/2014 | Campana et al. | |
| 2017/0211055 | A1 | 7/2017 | Brogdon et al. | |

FOREIGN PATENT DOCUMENTS

EP 3336107 A1 * 6/2018 ............ A61K 35/15
WO 2016/028896 A 2/2016

OTHER PUBLICATIONS

Maude et al., New England Journal of Medicine, 371:1507-17 (Year: 2014).*
Davila et al., Science Translational Medicine, vol. 6, 23 pages (Year: 2014).*
Davila et al., OncoImmunology vol. 1, No. 9, pp. 1577-1583 (Year: 2012).*
Geldres et al., Sem Immunol 28:3-9 (Year: 2016).*
Li et al., poster presented Feb. 2017 at the American Society for Bone Marrow Transplantation Conference; DOI:10.13140/RG.2.2.14247.75682 (Year: 2017).*
Japan Office Action, Application No. 2020-516722, dated Feb. 1, 2022.
Arch, Robert H., et al., "4-1BB and Ox40 Are Members of a Tumor Necrosis Factor (TNF)-Nerve Growth Factor Receptor Subfamily that Bind TNF Receptor-Associated Factors and Activate Nuclear Factor kB," Molecular and Cellular Biology, (1998), pp. 558-565.
Long, Adrienne H., et al., "4-1BB Costimulation Ameliorates T Cell Exhaustion Induced by Tonic Signaling of Chimeric Antigen Receptors," Nat. Med. vol. 21, No. 6 (2015) pp. 581-590.
Sadelain, Michel, et al, "Targeting Tumours with Genetically Enhanced T Lymphocytes," Nature Reviews, vol. 3 (2003) pp. 35-44.
Rosenberg, Steven A., et al., "Use of Tumor-Infiltrating Lymphocytes and Interleukin-2 in the Immunotherapy of Patients with Metastatic Melanoma," The New England Journal of Medicine, vol. 319, No. 25 (1988), pp. 1676-1680.
Narni-Mancinelli, Emilie, et al., "The 'T-cell'ness' of NK cells: unexpected similarities between NK cells and T cells," International Immunology, vol. 23, No. 7 (2011), pp. 427-431.
Godfrey, James, et al., "The role of natural killer cells in immunity against multiple myeloma," Leukemia & Lymphoma, No. 53 (2012), pp. 1666-1676.

(Continued)

*Primary Examiner* — Jessica H Roark
(74) *Attorney, Agent, or Firm* — Thomas | Horstemeyer, LLP

(57) ABSTRACT

Disclosed herein are chimeric antigen receptor (CAR) polypeptides, which can be used with adoptive cell transfer to target and kill cancers, that comprise a co-stimulatory signaling region having a mutated form of a cytoplasmic domain of CD28 that enhances CAR-T cell function, a mutated form of a cytoplasmic domain of 41BB that enhances nuclear factor kappaB (NFκB) signaling, or a combination thereof. Also disclosed are immune effector cells, such as T cells or Natural Killer (NK) cells, that are engineered to express these CARs. Also disclosed are immune effector cells co-expressing a CAR and one or more TRAF proteins. Therefore, also disclosed are methods of providing an anti-tumor immunity in a subject with a tumor associated antigen-expressing cancer that involves adoptive transfer of the disclosed immune effector cells.

18 Claims, 57 Drawing Sheets
Specification includes a Sequence Listing.

(56) References Cited

OTHER PUBLICATIONS

Woof, Jenny M., et al., "Human Antibody-FC Receptor Interactions Illuminated by Crystal Structures," Nature Reviews, vol. 4 (2004), (11 pages).
Maher, John, et al., "Human T-lymphocyte cytotoxicity and proliferation directed by a single chimeric TCR/CD28 receptor," Nature Biotechnology, vol. 20 (2002), pp. 70-75.
Fesnak, Andrew D., et al, "Engineered T Cells: The Promise and Challenges of Cancer Immunotherapy," Nat. Rev. Cancer, vol. 16, No. 9 (2016), pp. 566-581.
Gangadhar, Tara C., et al., "Mitigating the toxic effects of anticancer immunotherapy," Nature Reviews, vol. 11 (2014), pp. 91-99.
Fauriat, C., et al., "Impaired activating receptor expression pattern in natural killer cells from patients with multiple myeloma," Leukemia, vol. 20 (2006) (2 pages).
Porter, David L., et al., "Chimeric Antigen Receptor-Modified T Cells in Chronic Lymphoid Leukemia," The New England Journal of Medicine, vol. 365, No. 8 (2011), pp. 725-733.
Morgan, Richard A., et al., "Case Report of a Serious Adverse Event Following the Administration of T-Cells Transduced With a Chimeric Antigen Receptor Recognizing ERBB2," Molecular Therapy, vol. 18, No. 4 (2010), pp. 843-851.
Imai, C., et al., "Chimeric receptors with 4-1BB signaling capacity provoke potent cytotoxicity against acute lymphoblastic leukemia," Leukemia, vol. 18 (2004), pp. 676-684.
Maude, Shannon L., et al., "Chimeric Antigen Receptor T Cells for Sustained Remissions in Leukemia," The New England Journal of Medicine, No. 371, No. 16 (2014), pp. 1507-1517.
Davila, Marco L., et al, "Efficacy and Toxicity Management of 19-28z CAR T Cell Therapy in B Cell Acute Lymphoblastic Leukemia," Sci Transl. Med., vol. 6 (2014) (23 pages).
Davila, Marco L., et al., "How do CARs work? Early insights from recent clinical studies targeting CD19," Oncolmmunology, vol. 1, No. 9 (2012), pp. 1577-1583.
Esensten et al., CD28 Costimulation: From Mechanism to Therapy, Immunity, vol. 44(5), p. 973-88, 2016.
Pagan et al., CD28 Promotes CD4+ T Cell Clonal Expansion during Infection Independently of Its YMNM and PYAP Motifs, J Immunol., vol. 189(6), pt 2909-17, 2012.
Boomer et al., An Enigmatic Tail of CD28 Signaling, Cold Spring Harb Perspect Biol., vol. 2(8), p. 1-20, 2010.
Liu et al., A Chimeric Switch-Receptor Targeting PD1 Augments the Efficacy of Second-Generation CAR T Cells in Advanced Solid Tumors, Caner Res., vol. 76(6), p. 1578-90, 2016.
Liu et al., Targeting the phosphoinositide 3-kinase (PI3k) pathway in cancer, Nat Rev Drug Discov., vol. 8(8), p. 627-44, 2009.
Tang et al., Third-generation CD38/4-1BB chimeric antigen receptor T cells for chemotherapy relapsed or refractory acute lymphoblastic leukaemia: a non-randomised, open-label phase I trial protocol, BMJ Open, vol. 6(12), p. 1-7, 2016.
So et al., Antigen-independent signalosome of CARMA1, PKC?, and TNF receptor-associated factor 2(TRAF2) determines NF-?B signaling in T cells, Proc Natl Acad Sci USA, vol. 108(7), p. 2303-8, 2011.
International Search Report issued for PCT/US2018/050417, dated Jan. 28, 2019.

\* cited by examiner hum41BB IC domain 1 KRGRKKLLYIFKQPFMRPVQTTQEEDGCSCRFPEEE--GGCEL 42
mus41BB IC domain 1 KWIRKKFPHIFKQPFKKTTGAAQEEDACSCRCPQEEEGGGGYEL 45
                    *  *** * ****        **  * *** *  **

```
h19BBz  1  KRGRKKLLYIFKQFMPRPVQTTQEEDGCSCRFPEEEEGGCEL  42
mut01   1  KRGRKKLLYIFKQFMPRPVQTTAAAGCSCRFPEEEEGGCEL   42
mut02   1  KRGRKKLLYIFKQFMPRPVQTTQEEDGCSCRFPAAAAGGCEL  42
mut03   1  KRGRKKLLYIFKQFMPRPVQTTAAAGCSCRFPAAAAGGCEL   42
mut04   1  KRGRKKLLYIFKQFMPRPVQTTQEEDGCSCRFPEEEEGGCEL  84
```

FIG. 5C

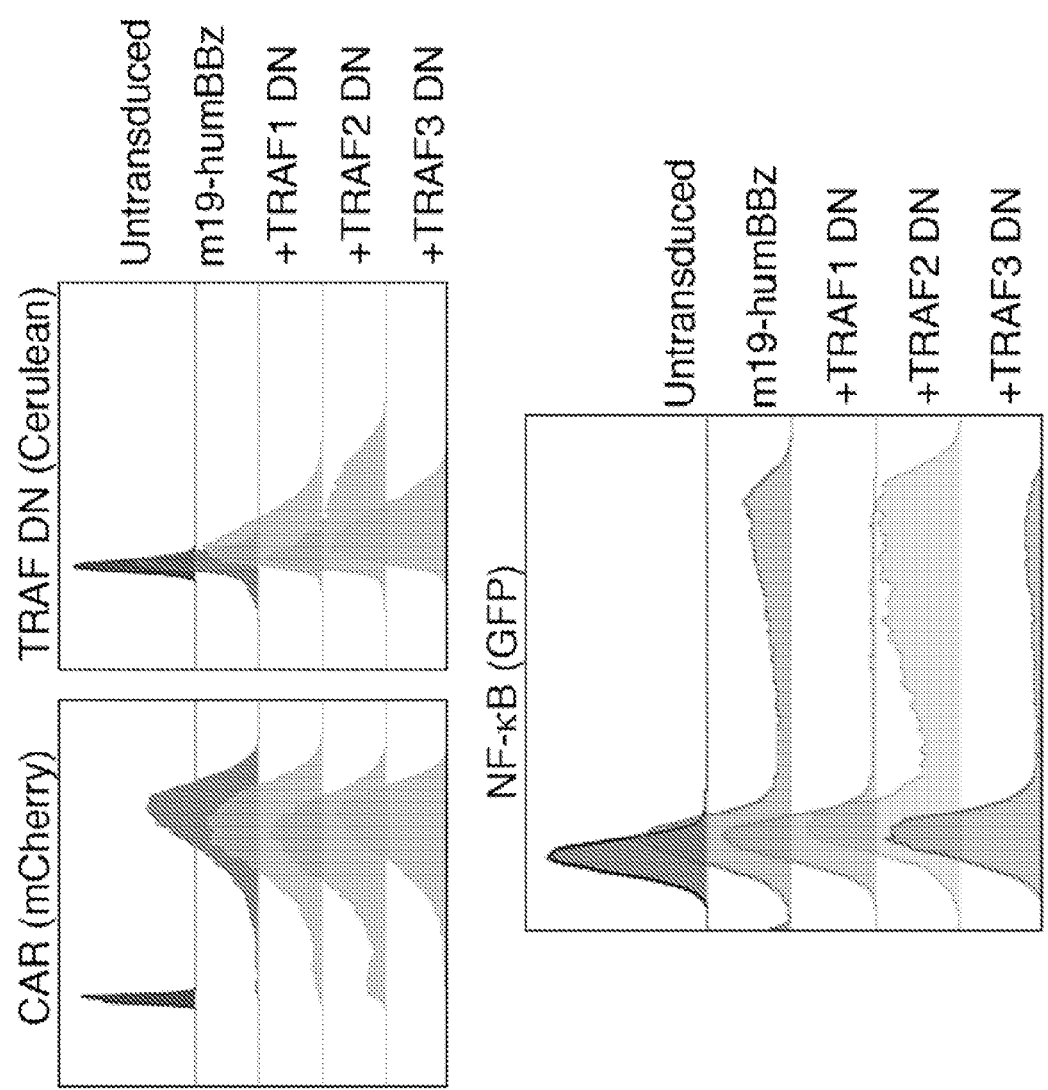

```
                         SEQUENCE LISTING

<160> NUMBER OF SEQ ID NOS: 28

<210> SEQ ID NO 1
<211> LENGTH: 42
<212> TYPE: PRT
<213> ORGANISM: Artificial Sequence
<220> FEATURE:
<223> OTHER INFORMATION: Synthetic Construct

<400> SEQUENCE: 1

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 2
<211> LENGTH: 42
<212> TYPE: PRT
<213> ORGANISM: Artificial Sequence
<220> FEATURE:
<223> OTHER INFORMATION: Synthetic Construct

<400> SEQUENCE: 2

Lys Arg Gly Arg Lys Lys Leu Leu Tyr Ile Phe Lys Gln Pro Phe Met
1               5                   10                  15

Arg Pro Val Gln Thr Thr Ala Ala Ala Ala Gly Cys Ser Cys Arg Phe
            20                  25                  30

Pro Glu Glu Glu Glu Gly Gly Cys Glu Leu
        35                  40

<210> SEQ ID NO 3
<211> LENGTH: 42
<212> TYPE: PRT
<213> ORGANISM: Artificial Sequence
<220> FEATURE:
<223> OTHER INFORMATION: Synthetic Construct

<400> SEQUENCE: 3

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
```

```
                 20                  25                  30

Pro Ala Ala Ala Ala Gly Gly Cys Glu Leu
        35                  40

<210> SEQ ID NO 4
<211> LENGTH: 42
<212> TYPE: PRT
<213> ORGANISM: Artificial Sequence
<220> FEATURE:
<223> OTHER INFORMATION: Synthetic Construct

<400> SEQUENCE: 4

Lys Arg Gly Arg Lys Lys Leu Leu Tyr Ile Phe Lys Gln Pro Phe Met
1               5                   10                  15

Arg Pro Val Gln Thr Thr Ala Ala Ala Gly Cys Ser Cys Arg Phe
            20                  25                  30

Pro Ala Ala Ala Ala Gly Gly Cys Glu Leu
        35                  40

<210> SEQ ID NO 5
<211> LENGTH: 84
<212> TYPE: PRT
<213> ORGANISM: Artificial Sequence
<220> FEATURE:
<223> OTHER INFORMATION: Synthetic Construct

<400> SEQUENCE: 5

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Gln Glu Glu Asp Gly Cys Ser Cys Arg Phe Pro Glu Glu Glu Glu Gly
65                  70                  75                  80

Gly Cys Glu Leu

<210> SEQ ID NO 6
<211> LENGTH: 84
<212> TYPE: PRT
<213> ORGANISM: Artificial Sequence
<220> FEATURE:
<223> OTHER INFORMATION: Synthetic Construct

<400> SEQUENCE: 6

Lys Arg Gly Arg Lys Lys Leu Leu Tyr Ile Phe Lys Gln Pro Phe Met
1               5                   10                  15

Arg Pro Val Gln Thr Thr Ala Ala Ala Gly Cys Ser Cys Arg Phe
            20                  25                  30

Pro Glu Glu Glu Glu Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Gln Glu Glu Asp Gly Cys Ser Cys Arg Phe Pro Glu Glu Glu Glu Gly
65                  70                  75                  80

Gly Cys Glu Leu
```

```
<210> SEQ ID NO 7
<211> LENGTH: 84
<212> TYPE: PRT
<213> ORGANISM: Artificial Sequence
<220> FEATURE:
<223> OTHER INFORMATION: Synthetic Construct

<400> SEQUENCE: 7

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Ala Ala Ala Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Gln Glu Glu Asp Gly Cys Ser Cys Arg Phe Pro Glu Glu Glu Glu Gly
65                  70                  75                  80

Gly Cys Glu Leu

<210> SEQ ID NO 8
<211> LENGTH: 84
<212> TYPE: PRT
<213> ORGANISM: Artificial Sequence
<220> FEATURE:
<223> OTHER INFORMATION: Synthetic Construct

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Ala Ala Ala Ala Gly Cys Ser Cys Arg Phe Pro Glu Glu Glu Glu Gly
65                  70                  75                  80

Gly Cys Glu Leu

<210> SEQ ID NO 9
<211> LENGTH: 84
<212> TYPE: PRT
<213> ORGANISM: Artificial Sequence
<220> FEATURE:
<223> OTHER INFORMATION: Synthetic Construct

<400> SEQUENCE: 9

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Gln Glu Glu Asp Gly Cys Ser Cys Arg Phe Pro Ala Ala Ala Ala Gly
65                  70                  75                  80

Gly Cys Glu Leu
```

<210> SEQ ID NO 10
<211> LENGTH: 84
<212> TYPE: PRT
<213> ORGANISM: Artificial Sequence
<220> FEATURE:
<223> OTHER INFORMATION: Synthetic Construct

<400> SEQUENCE: 10

Lys Arg Gly Arg Lys Lys Leu Leu Tyr Ile Phe Lys Gln Pro Phe Met
1               5                   10                  15

Arg Pro Val Gln Thr Thr Ala Ala Ala Gly Cys Ser Cys Arg Phe
            20                  25                  30

Pro Ala Ala Ala Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Gln Glu Glu Asp Gly Cys Ser Cys Arg Phe Pro Glu Glu Glu Glu Gly
65                  70                  75                  80

Gly Cys Glu Leu

<210> SEQ ID NO 11
<211> LENGTH: 84
<212> TYPE: PRT
<213> ORGANISM: Artificial Sequence
<220> FEATURE:
<223> OTHER INFORMATION: Synthetic Construct

<400> SEQUENCE: 11

Lys Arg Gly Arg Lys Lys Leu Leu Tyr Ile Phe Lys Gln Pro Phe Met
1               5                   10                  15

Arg Pro Val Gln Thr Thr Ala Ala Ala Gly Cys Ser Cys Arg Phe
            20                  25                  30

Pro Glu Glu Glu Glu Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Ala Ala Ala Ala Gly Cys Ser Cys Arg Phe Pro Glu Glu Glu Glu Gly
65                  70                  75                  80

Gly Cys Glu Leu

<210> SEQ ID NO 12
<211> LENGTH: 84
<212> TYPE: PRT
<213> ORGANISM: Artificial Sequence
<220> FEATURE:
<223> OTHER INFORMATION: Synthetic Construct

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Ala Ala Ala Gly Cys Ser Cys Arg Phe
            20                  25                  30

Pro Glu Glu Glu Glu Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Gln Glu Glu Asp Gly Cys Ser Cys Arg Phe Pro Ala Ala Ala Ala Gly
65                  70                  75                  80

Gly Cys Glu Leu

<210> SEQ ID NO 13
<211> LENGTH: 84
<212> TYPE: PRT
<213> ORGANISM: Artificial Sequence
<220> FEATURE:
<223> OTHER INFORMATION: Synthetic Construct

<400> SEQUENCE: 13

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Ala Ala Ala Ala Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Ala Ala Ala Ala Gly Cys Ser Cys Arg Phe Pro Glu Glu Glu Glu Gly
65                  70                  75                  80

Gly Cys Glu Leu

<210> SEQ ID NO 14
<211> LENGTH: 84
<212> TYPE: PRT
<213> ORGANISM: Artificial Sequence
<220> FEATURE:
<223> OTHER INFORMATION: Synthetic Construct

<400> SEQUENCE: 14

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Ala Ala Ala Ala Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Gln Glu Glu Asp Gly Cys Ser Cys Arg Phe Pro Ala Ala Ala Ala Gly
65                  70                  75                  80

Gly Cys Glu Leu

<210> SEQ ID NO 15
<211> LENGTH: 84
<212> TYPE: PRT
<213> ORGANISM: Artificial Sequence
<220> FEATURE:
<223> OTHER INFORMATION: Synthetic Construct

<400> SEQUENCE: 15

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

```
Ala Ala Ala Ala Gly Cys Ser Cys Arg Phe Pro Ala Ala Ala Gly
65                  70                  75                  80

Gly Cys Glu Leu

<210> SEQ ID NO 16
<211> LENGTH: 84
<212> TYPE: PRT
<213> ORGANISM: Artificial Sequence
<220> FEATURE:
<223> OTHER INFORMATION: Synthetic Construct

<400> SEQUENCE: 16

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Ala Ala Ala Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Ala Ala Ala Ala Gly Cys Ser Cys Arg Phe Pro Ala Ala Ala Gly
65                  70                  75                  80

Gly Cys Glu Leu

<210> SEQ ID NO 17
<211> LENGTH: 84
<212> TYPE: PRT
<213> ORGANISM: Artificial Sequence
<220> FEATURE:
<223> OTHER INFORMATION: Synthetic Construct

<400> SEQUENCE: 17

Lys Arg Gly Arg Lys Lys Leu Leu Tyr Ile Phe Lys Gln Pro Phe Met
1               5                   10                  15

Arg Pro Val Gln Thr Thr Ala Ala Ala Gly Cys Ser Cys Arg Phe
            20                  25                  30

Pro Glu Glu Glu Glu Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Ala Ala Ala Ala Gly Cys Ser Cys Arg Phe Pro Ala Ala Ala Gly
65                  70                  75                  80

Gly Cys Glu Leu

<210> SEQ ID NO 18
<211> LENGTH: 84
<212> TYPE: PRT
<213> ORGANISM: Artificial Sequence
<220> FEATURE:
<223> OTHER INFORMATION: Synthetic Construct

<400> SEQUENCE: 18

Lys Arg Gly Arg Lys Lys Leu Leu Tyr Ile Phe Lys Gln Pro Phe Met
1               5                   10                  15

Arg Pro Val Gln Thr Thr Ala Ala Ala Gly Cys Ser Cys Arg Phe
            20                  25                  30

Pro Ala Ala Ala Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
```

```
                      50                  55                  60
Gln Glu Glu Asp Gly Cys Ser Cys Arg Phe Pro Ala Ala Ala Gly
 65                  70                  75                  80

Gly Cys Glu Leu

<210> SEQ ID NO 19
<211> LENGTH: 84
<212> TYPE: PRT
<213> ORGANISM: Artificial Sequence
<220> FEATURE:
<223> OTHER INFORMATION: Synthetic Construct

<400> SEQUENCE: 19

Lys Arg Gly Arg Lys Lys Leu Leu Tyr Ile Phe Lys Gln Pro Phe Met
  1               5                  10                  15

Arg Pro Val Gln Thr Thr Ala Ala Ala Gly Cys Ser Cys Arg Phe
                 20                  25                  30

Pro Ala Ala Ala Ala Gly Gly Cys Glu Leu Lys Arg Gly Arg Lys Lys
             35                  40                  45

Leu Leu Tyr Ile Phe Lys Gln Pro Phe Met Arg Pro Val Gln Thr Thr
         50                  55                  60

Ala Ala Ala Ala Gly Cys Ser Cys Arg Phe Pro Glu Glu Glu Glu Gly
 65                  70                  75                  80

Gly Cys Glu Leu

<210> SEQ ID NO 20
<211> LENGTH: 84
<212> TYPE: PRT
<213> ORGANISM: Artificial Sequence
<220> FEATURE:
<223> OTHER INFORMATION: Synthetic Construct

<400> SEQUENCE: 20

Lys Arg Gly Arg Lys Lys Leu Leu Tyr Ile Phe Lys Gln Pro Phe Met
  1               5                  10                  15

Arg Pro Val Gln Thr Thr Ala Ala Ala Gly Cys Ser Cys Arg Phe
                 20                  25                  30

Pro Ala Ala Ala Ala Gly Gly Cys Glu Leu Lys Arg Gly Arg Lys Lys
             35                  40                  45

Leu Leu Tyr Ile Phe Lys Gln Pro Phe Met Arg Pro Val Gln Thr Thr
         50                  55                  60

Ala Ala Ala Ala Gly Cys Ser Cys Arg Phe Pro Ala Ala Ala Ala Gly
 65                  70                  75                  80

Gly Cys Glu Leu

<210> SEQ ID NO 21
<211> LENGTH: 42
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (23)..(23)
<223> OTHER INFORMATION: Xaa is not Gln
<220> FEATURE:
<221> NAME/KEY: MISC_FEATURE
<222> LOCATION: (24)..(25)
<223> OTHER INFORMATION: Xaa is not Glu
<220> FEATURE:
<221> NAME/KEY: MISC_FEATURE
<222> LOCATION: (26)..(26)
```

<223> OTHER INFORMATION: Xaa is not Asp

<400> SEQUENCE: 21

Lys Arg Gly Arg Lys Lys Leu Leu Tyr Ile Phe Lys Gln Pro Phe Met
1               5                   10                  15

Arg Pro Val Gln Thr Thr Xaa Xaa Xaa Xaa Gly Cys Ser Cys Arg Phe
            20                  25                  30

Pro Glu Glu Glu Glu Gly Gly Cys Glu Leu
        35                  40

<210> SEQ ID NO 22
<211> LENGTH: 42
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (34)..(37)
<223> OTHER INFORMATION: Xaa is not Glu

<400> SEQUENCE: 22

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Xaa Xaa Xaa Xaa Gly Gly Cys Glu Leu
        35                  40

<210> SEQ ID NO 23
<211> LENGTH: 42
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (23)..(23)
<223> OTHER INFORMATION: Xaa is not Gln
<220> FEATURE:
<221> NAME/KEY: MISC_FEATURE
<222> LOCATION: (24)..(25)
<223> OTHER INFORMATION: Xaa is not Glu
<220> FEATURE:
<221> NAME/KEY: MISC_FEATURE
<222> LOCATION: (26)..(26)
<223> OTHER INFORMATION: Xaa is not Asp
<220> FEATURE:
<221> NAME/KEY: MISC_FEATURE
<222> LOCATION: (34)..(37)
<223> OTHER INFORMATION: Xaa is not Glu

<400> SEQUENCE: 23

Lys Arg Gly Arg Lys Lys Leu Leu Tyr Ile Phe Lys Gln Pro Phe Met
1               5                   10                  15

Arg Pro Val Gln Thr Thr Xaa Xaa Xaa Xaa Gly Cys Ser Cys Arg Phe
            20                  25                  30

Pro Xaa Xaa Xaa Xaa Gly Gly Cys Glu Leu
        35                  40

<210> SEQ ID NO 24
<211> LENGTH: 84
<212> TYPE: PRT
<213> ORGANISM: Artificial Sequence
<220> FEATURE:
<223> OTHER INFORMATION: Synthetic Construct
<220> FEATURE:

```
<221> NAME/KEY: MISC_FEATURE
<222> LOCATION: (23)..(23)
<223> OTHER INFORMATION: Xaa is not Gln
<220> FEATURE:
<221> NAME/KEY: MISC_FEATURE
<222> LOCATION: (24)..(25)
<223> OTHER INFORMATION: Xaa is not Glu
<220> FEATURE:
<221> NAME/KEY: MISC_FEATURE
<222> LOCATION: (26)..(26)
<223> OTHER INFORMATION: Xaa is not Asp
<220> FEATURE:
<221> NAME/KEY: MISC_FEATURE
<222> LOCATION: (34)..(37)
<223> OTHER INFORMATION: Xaa is not Glu
<220> FEATURE:
<221> NAME/KEY: MISC_FEATURE
<222> LOCATION: (65)..(65)
<223> OTHER INFORMATION: Xaa is not Gln
<220> FEATURE:
<221> NAME/KEY: MISC_FEATURE
<222> LOCATION: (66)..(67)
<223> OTHER INFORMATION: Xaa is not Glu
<220> FEATURE:
<221> NAME/KEY: MISC_FEATURE
<222> LOCATION: (68)..(68)
<223> OTHER INFORMATION: Xaa is not Asp
<220> FEATURE:
<221> NAME/KEY: MISC_FEATURE
<222> LOCATION: (76)..(79)
<223> OTHER INFORMATION: Xaa is not Glu

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Xaa Xaa Xaa Xaa Gly Cys Ser Cys Arg Phe
            20                  25                  30

Pro Xaa Xaa Xaa Xaa Gly Gly Cys Glu Leu Lys Arg Gly Arg Lys Lys
        35                  40                  45

Leu Leu Tyr Ile Phe Lys Gln Pro Phe Met Arg Pro Val Gln Thr Thr
    50                  55                  60

Xaa Xaa Xaa Xaa Gly Cys Ser Cys Arg Phe Pro Xaa Xaa Xaa Xaa Gly
65                  70                  75                  80

Gly Cys Glu Leu

<210> SEQ ID NO 25
<211> LENGTH: 45
<212> TYPE: PRT
<213> ORGANISM: Artificial Sequence
<220> FEATURE:
<223> OTHER INFORMATION: Synthetic Construct

<400> SEQUENCE: 25

Lys Trp Ile Arg Lys Lys Phe Pro His Ile Phe Lys Gln Pro Phe Lys
1               5                   10                  15

Lys Thr Thr Gly Ala Ala Gln Glu Glu Asp Ala Cys Ser Cys Arg Cys
            20                  25                  30

Pro Gln Glu Glu Glu Gly Gly Gly Gly Tyr Glu Leu
        35                  40                  45

<210> SEQ ID NO 26
<211> LENGTH: 4
<212> TYPE: PRT
<213> ORGANISM: Artificial Sequence
<220> FEATURE:
<223> OTHER INFORMATION: Synthetic Construct

<400> SEQUENCE: 26
```

```
Tyr Met Asn Met
1

<210> SEQ ID NO 27
<211> LENGTH: 4
<212> TYPE: PRT
<213> ORGANISM: Artificial Sequence
<220> FEATURE:
<223> OTHER INFORMATION: Synthetic Construct

<400> SEQUENCE: 27

Pro Arg Arg Pro
1

<210> SEQ ID NO 28
<211> LENGTH: 4
<212> TYPE: PRT
<213> ORGANISM: Artificial Sequence
<220> FEATURE:
<223> OTHER INFORMATION: Synthetic Construct

<400> SEQUENCE: 28

Pro Tyr Ala Pro
1
```

CHIMERIC ANTIGEN RECEPTORS WITH ENHANCED NFκB SIGNALING

CROSS-REFERENCE TO RELATED APPLICATIONS

PCT/US2018/050417, filed Sep. 11, 2018, which claims benefit of U.S. Provisional Application No. 62/561,815, filed Sep. 22, 2017, U.S. Provisional Application No. 62/597,128, filed Dec. 11, 2017, U.S. Provisional Application No. 62/640,153, filed Mar. 8, 2018, U.S. Provisional Application No. 62/666,381, filed May 3, 2018, and U.S. Provisional Application No. 62/666,385, filed May 3, 2018, all of which are hereby incorporated herein by reference in their entirety.

SEQUENCE LISTING

This application contains a sequence listing filed in electronic form as an ASCII.txt file entitled "320103-2020 Sequence Listing_ST25" created on Jan. 18, 2022, having 20,060 bytes. The content of the sequence listing is incorporated herein in its entirety.

BACKGROUND

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed.

A major advance for anti-cancer T cell therapy is the chimeric antigen receptor (CAR), which is a single chain variable fragment (scFv) derived from an antibody fused to the signaling domains of a T cell receptor (TCR) (Davila, M. L., et al., Oncoimmunology, 2012. 1(9):1577-1583). The intracellular domain of a first-generation CAR includes only CD3ζ, while second-generation CARs also include co-stimulatory domains such as CD28 or 41BB. These second-generation CAR domains support highly-efficacious tumor killing in mice and led to the clinical evaluation of CAR T cell therapies in patients. The potential of CD19-targeted CAR T cells was confirmed by reports of complete remission rates of 90% for patients with B cell acute lymphoblastic leukemia (B-ALL) (Davila, M. L., et al., Sci Transl Med, 2014. 6(224):224ra25; Maude, S. L., et al., N Engl J Med, 2014. 371(16):1507-17). However, poor CAR T cell persistence and excessive T cell activation contribute to relapses and severe toxicities, respectively, and suggest a critical need to understand CAR T cell biology (Gangadhar, T. C. and R. H. Vonderheide, Nat Rev Clin Oncol, 2014. 11(2):91-9). Furthermore, relapses and toxicities have been seen with all second-generation CARs suggesting that the addition of co-stimulatory domains to CARs improved efficacy, but at the cost of biologic complications.

SUMMARY

Disclosed herein are chimeric antigen receptor (CAR) polypeptides that can be used with adoptive cell transfer that have enhanced co-stimulation. The disclosed CARs comprise a costimulatory signaling region with one or more mutations in the cytoplasmic domains of CD28 and/or 41BB that enhance signaling that CAR-T cell function.

In some embodiments, the mutated costimulatory signaling region reduces CAR-T cell exhaustion. The CD28 domain includes 3 intracellular subdomains (YMNM (SEQ ID NO:26), PRRP (SEQ ID NO:27), and PYAP (SEQ ID NO:28)) that regulate signaling pathways post TCR-stimulation. In some embodiments, the disclosed CAR comprises mutation or deletion of one or more of these subdomains that enhances CAR-T cell function, e.g. reducing CAR-T cell exhaustion.

As disclosed herein, the level of nuclear factor kappaB (NFκB) signaling supported by chimeric antigen receptors (CARs) correlates with their function. Therefore, disclosed herein are chimeric antigen receptors (CARs) with enhanced NFκB signaling. As further disclosed herein, the co-stimulatory protein 41BB (CD137) activates NFκB signaling in T-cells through tumor necrosis factor receptor-associated factor (TRAF). Therefore, the disclosed CARs can enhance 41BB activation by TRAF proteins. In some cases, the disclosed CARs comprise two or more copies of 41BB. Also as disclosed herein, TRAF proteins can independently regulate CAR expression, persistence, proliferation, cytokine production, and cytotoxicity. Moreover, each TRAF has a different impact on CAR T cell function.

Therefore, disclosed herein are CARs comprising one or more 41BB domains with mutations that enhance binding to specific TRAF proteins, such as TRAF1, TRAF2, TRAF3, TRAF4, TRAF5, TRAF6, or any combination thereof. In some cases, the 41BB mutation enhances TRAF1- and/or TRAF2-dependent proliferation and survival of the T-cell, e.g. through NF-κB. In some cases, the 41BB mutation enhances TRAF3-dependent antitumor efficacy, e.g. through IRF7/INFβ.

Also as disclosed herein, TRAF proteins can in some cases enhance CAR T cell function independent of NFκB and 41BB. For example, TRAF proteins can in some cases enhance CD28 co-stimulation in T cells. Therefore, also disclosed herein are immune effector cells co-expressing CARs with one or more TRAF proteins, such as TRAF1, TRAF2, TRAF3, TRAF4, TRAF5, TRAF6, or any combination thereof. In some cases, the CAR is any CAR that targets a tumor antigen. For example, first-generation CARs typically had the intracellular domain from the CD3ζ chain, while second-generation CARs added intracellular signaling domains from various costimulatory protein receptors (e.g., CD28, 41BB, ICOS) to the endodomain of the CAR to provide additional signals to the T cell. In some cases, the CAR is the disclosed CAR with enhanced 41BB activation.

In some embodiments, the CAR polypeptides further comprise one or more deletions or mutations in CD3zeta and/or 41BB that enhance CAR T cell function.

As with other CARs, the disclosed CAR polypeptides contain in an ectodomain a binding agent that can bind cancer cells expressing tumor associated antigen (TAA). The disclosed polypeptides can also contain a transmembrane domain and an endodomain capable of activating an immune effector cell. For example, the endodomain can contain an intracellular signaling domain and optionally one or more co-stimulatory signaling regions.

The anti-TAA binding agent is in some embodiments an antibody fragment that specifically binds a TAA. For example, the antigen binding domain can be a Fab or a single-chain variable fragment (scFv) of an antibody that specifically binds a TAA. The anti-TAA binding agent is in some embodiments an aptamer that specifically binds the TAA. For example, the anti-TAA binding agent can be a peptide aptamer selected from a random sequence pool based on its ability to bind TAA. The anti-TAA binding agent can also be a natural ligand of TAA, or a variant and/or fragment thereof capable of binding the TAA.

In some embodiments, the intracellular signaling domain is a CD3 zeta (CD3ζ) signaling domain. In some cases, the costimulatory signaling region contains 1, 2, 3, or 4 cytoplasmic domains of one or more intracellular signaling molecules.

Also disclosed are isolated nucleic acid sequences encoding the disclosed CAR polypeptides, vectors comprising these isolated nucleic acids, and cells containing these vectors. For example, the cell can be an immune effector cell selected from the group consisting of an alpha-beta T cells, a gamma-delta T cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, and a regulatory T cell.

In some embodiments, the cell exhibits an anti-tumor immunity when the antigen binding domain of the CAR binds to the TAA on a tumor.

Also disclosed is a method of providing an anti-tumor immunity in a subject with a TAA-expressing cancer that involves administering to the subject an effective amount of an immune effector cell genetically modified with a disclosed TAA-specific CAR.

The details of one or more embodiments of the invention are set forth in the accompanying drawings and the description below. Other features, objects, and advantages of the invention will be apparent from the description and drawings, and from the claims.

AAPC at 10:1 E:T ratio overnight, FACS-sorted, and lysed to isolate RNA. Each group of CAR T cells was transduced, stimulated, and sorted independently in triplicates.

FIG. 10 shows fluorescent protein tagged CAR T cells function similarly to non-tagged counterparts. (A) Cytokines released by fluorescent protein tagged CAR T cells upon antigen stimulation. Day 4 CAR T cells were co-cultured with 3T3-mCD19 at 10:1 ratio for 24 hr. Supernatant was subjected to luminex assay for IFNγ and TNFα. (B) Immune phenotype of CAR T cells with a fluorescent protein tag. Day 4 CAR T cells were harvested, beads removed and subjected to flow cytometry. Cells were pre-gated on single live cells (top) or CD3+CAR+ cells (middle & bottom). (C) Survival (n=50), in vivo B cell killing and CAR T persistence in mice treated by CAR T cells with a fluorescent protein tag. Seven days after i.v. injection with 1×106 Eμ-ALL cells, mice were i.p. injected with CTX at 250 mg/kg and then one day later i.v. injected with $1 \times 10^6$ CAR T cells. Survival was monitored. BM was isolated 11 days after CAR T injection and subjected to flow cytometry. B (B220+CD19+) and CAR T (CD3+-CAR+) cells were counted using CountBright beads. Each dot indicates one mouse (n=3 per group). Data are from one single experiment. (D) B and CAR T cell counts over time in the blood after CAR T treatment. B6 mice were injected with CTX (250 mg/kg) and CAR T cells ($3 \times 10^5$). Blood samples were collected overtime and B and CAR T cell numbers were measured by flow cytometry (n=10 per group). Survival curve, log rank test; all other data, unpaired t test. *p<0.05; p<0.01; *p<0.001; ****p<0.0001; ns, not significant.

Figures 2A, 2B:
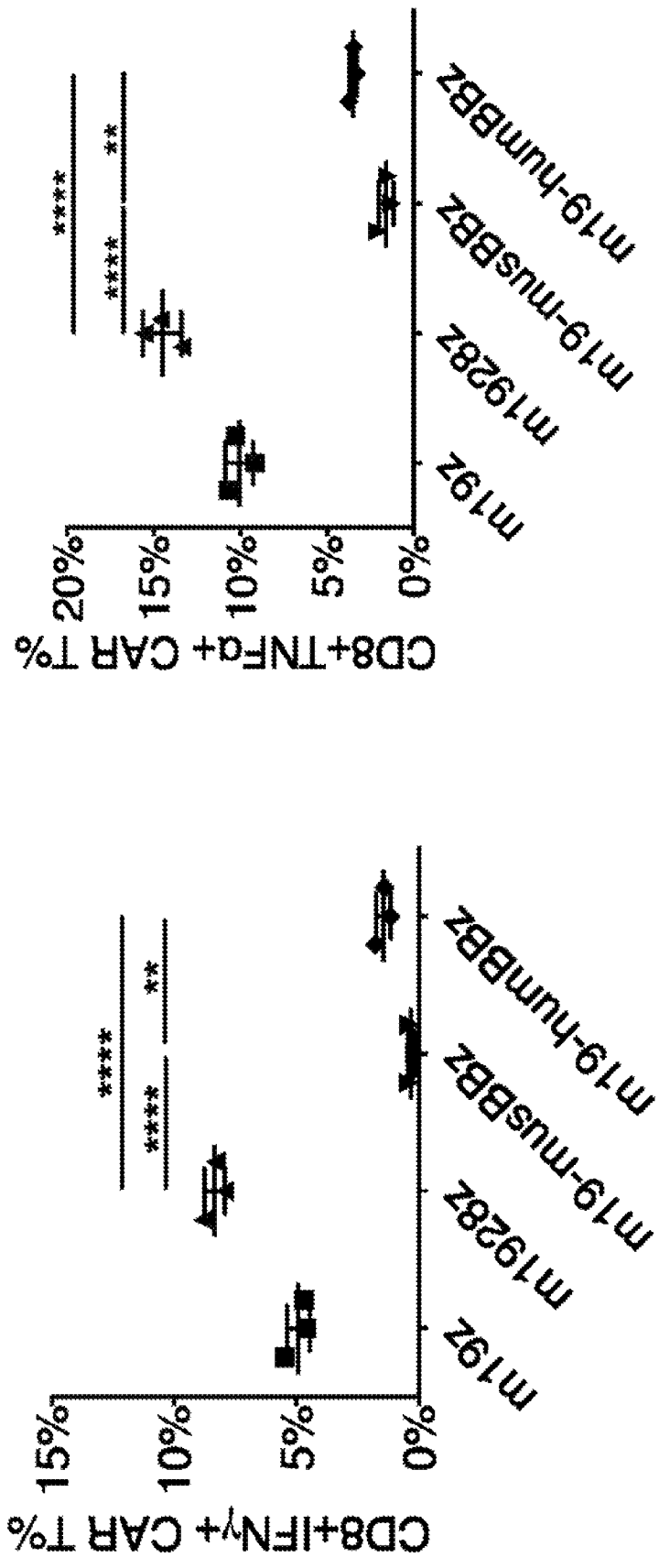
FIG. 2 shows at a stress test dose mCD19-targeted CAR T cells containing a human 4-1BB endodomain (m19-humBBz) display comparable in vivo function to m1928z CAR T cells. (A) Amino acid sequence alignment of mouse (SEQ ID NO:25) and human (SEQ ID NO:1) 4-1BB endodomains. Identical amino acids are indicated with an asterisk. (B) Intracellular IFNγ and TNFα in CAR T cells upon mCD19 antigen stimulation. One million transduced T cells were co-cultured with 1×10$^5$ irradiated 3T3-mCD19 for 4 hr in the presence of protein transport inhibitor. Cells were subjected to flow cytometry. Data are representative of two independent experiments performed in triplicate. (C) Cytotoxicity assay. CAR T cells were co-cultured with 3T3-mCD19 at a E:T ratio of 10:1 and target cell killing was monitored on an xCELLigence RTCA system. Data are from one experiment in triplicate. (D) Overall survival. Mice were treated with i.p. CTX (250-300 mg/kg) and iv. CAR T cells (1.5-3×10$^5$ CAR T cells per mouse). Data are pooled from 4 independent experiments. n=127. (E) B (CD19+B220+) and CAR T (CD3+ CAR+) cells in femurs 1 week after CAR T cell injection. Bone marrow cells were isolated and subjected to flow cytometry. Data are pooled from two independent experiments (n=33 total). Each dot indicates one mouse. All counts were calculated with Countbright beads. Survival curve, log rank test; all other data, unpaired t test. *p<0.05; p<0.01; *p<0.001; ****p<0.0001; ns, not significant.
Figure 2C:
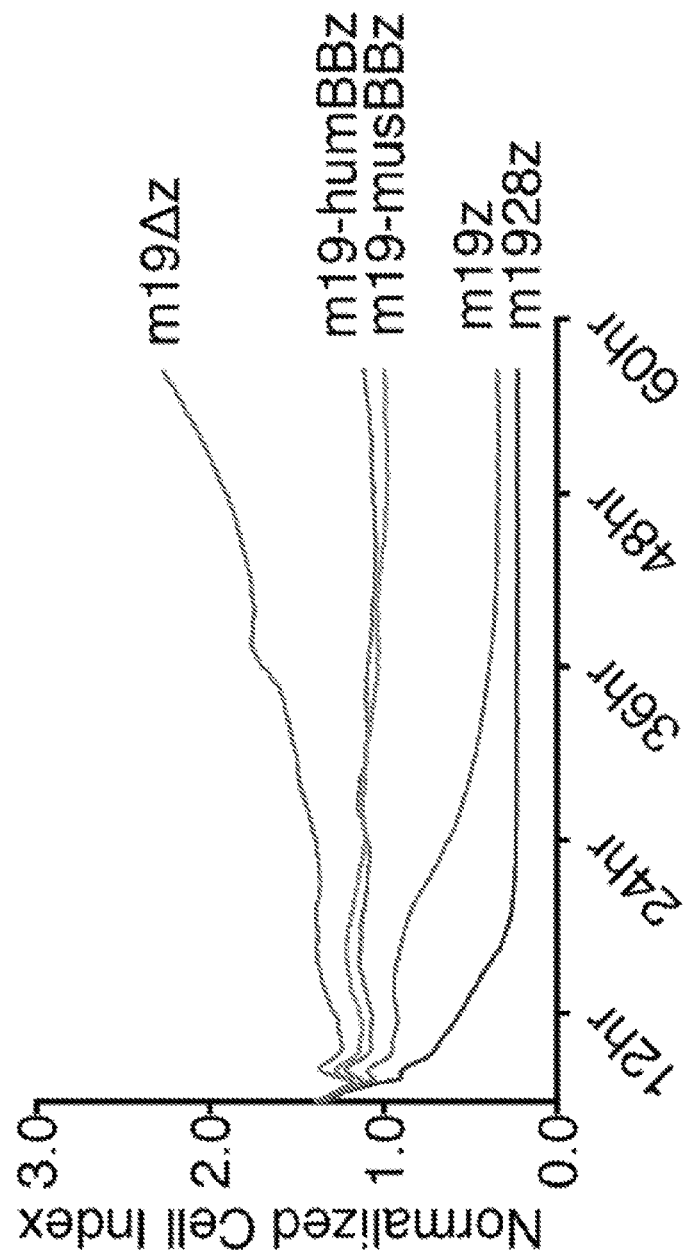
Figure 2D:
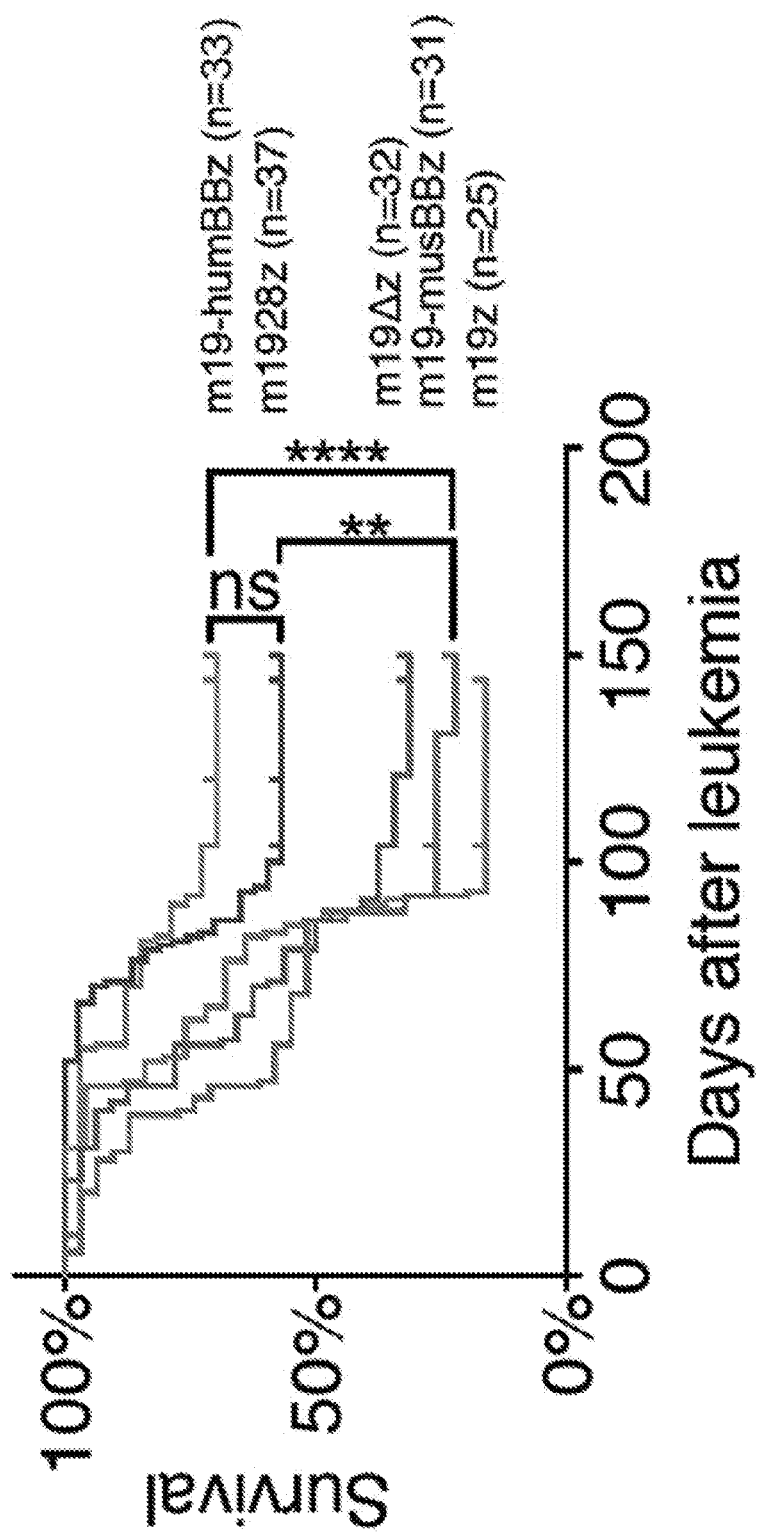
Figure 11:
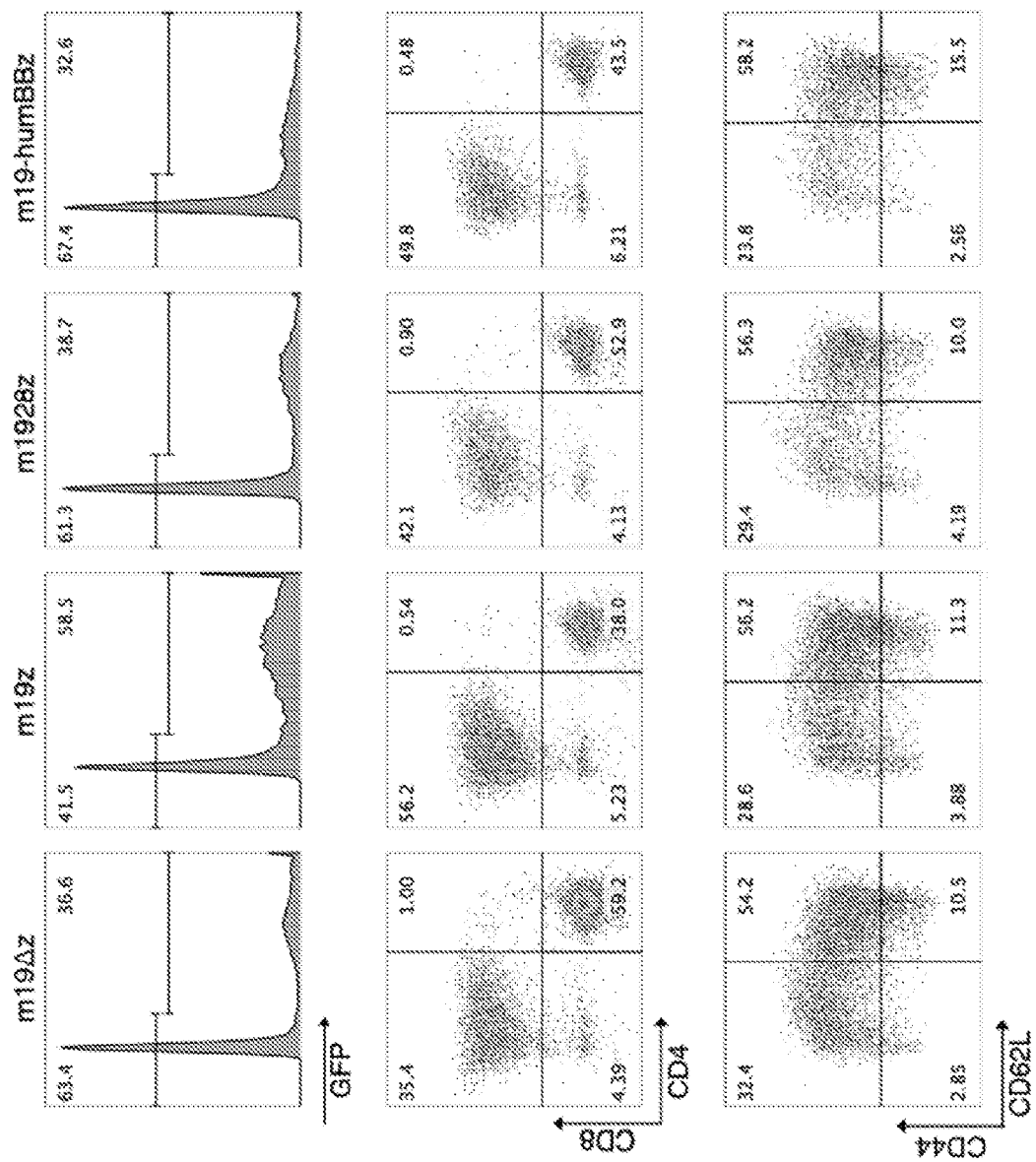

FIG. 11 shows transduction efficiency and immune phenotype of mCD19 targeted CAR T cells for survival study (FIG. 2D). Data are representative of four independent productions used to generate CAR T cells for the survival experiments of FIG. 2D. For transduction efficiency (top panel), cells were pre-gated on single live cells. For immune phenotype (middle and bottom panels), cells were pre-gated on single live CAR T (CD3+CAR+) cells.

Figure 3A:
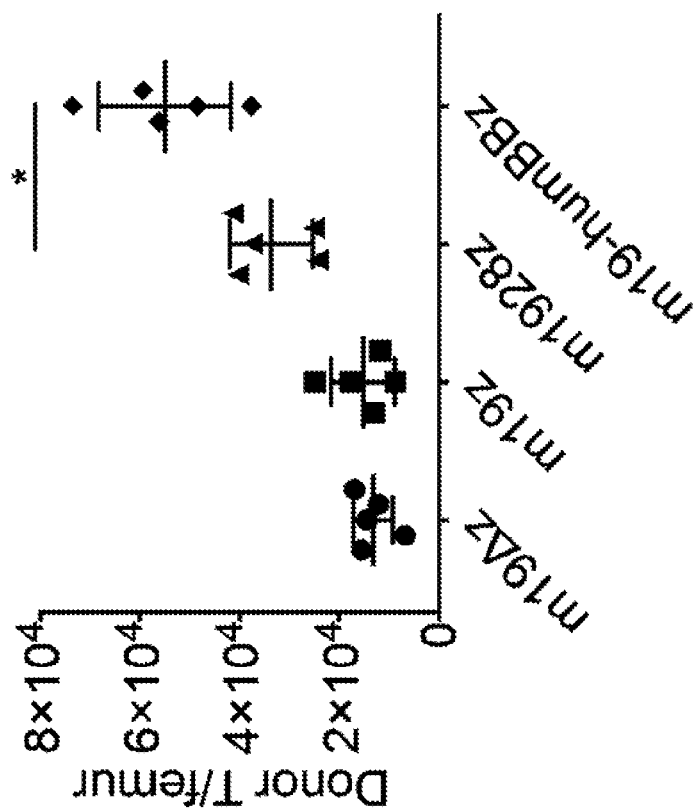
FIG. 3 shows persistence of m19-humBBz CAR T cells is required for optimal function in vivo. (A) CAR T (CD3+ CAR+) and Donor T (CD3+ Thy1.1+) cell numbers in Rag1$^{-/-}$ mice 1 week after transfer. One million CAR T cells were i.v. injected in Rag1$^{-/-}$ mice. One week later, BM cells were isolated, stained and analyzed by flow cytometry. Each dot indicates one mouse. n=5 per group. For (B) and (C), one million irradiated or non-irradiated CAR T cells were i.v. injected into CTX (300 mg/kg) pre-conditioned C57BL/6 mice. One week later, blood and BM were collected, stained and analyzed by flow cytometry. (B) Irradiated and non-irradiated CAR T cell (CD3+ CAR+) numbers in the blood and BM 1 week after transfer. (C) B cell (B220+CD19+) numbers in the blood and B cell percentages in the BM 1 week after CAR T transfer. Data are from one experiment. Each dot indicates one mouse. n=10 per group for blood samples; n=3 per group for BM samples. All data, unpaired t test. *p<0.05; p<0.01; **p<0.0001; ns, not significant.
Figure 3A:
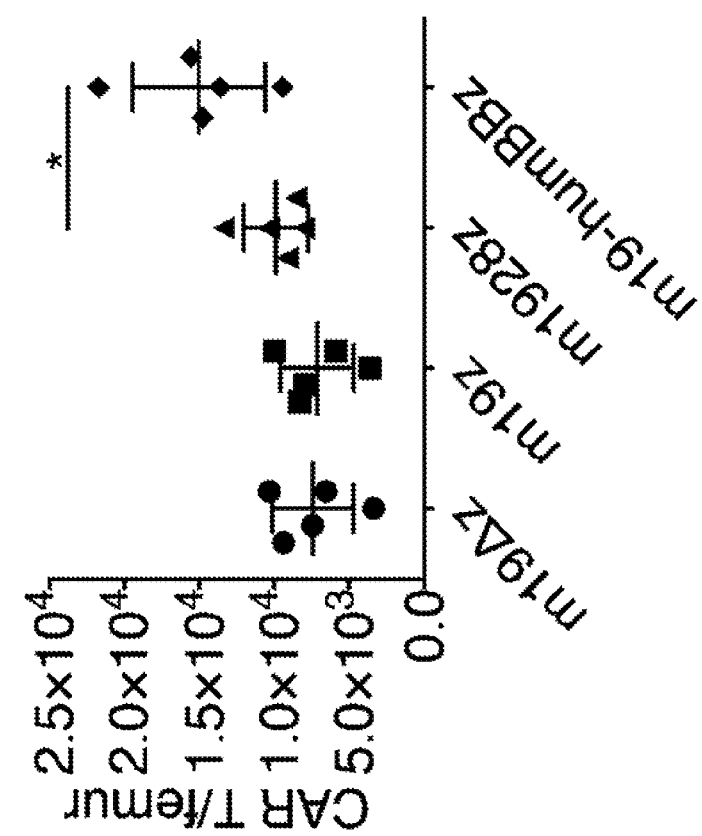
Figure 3B:
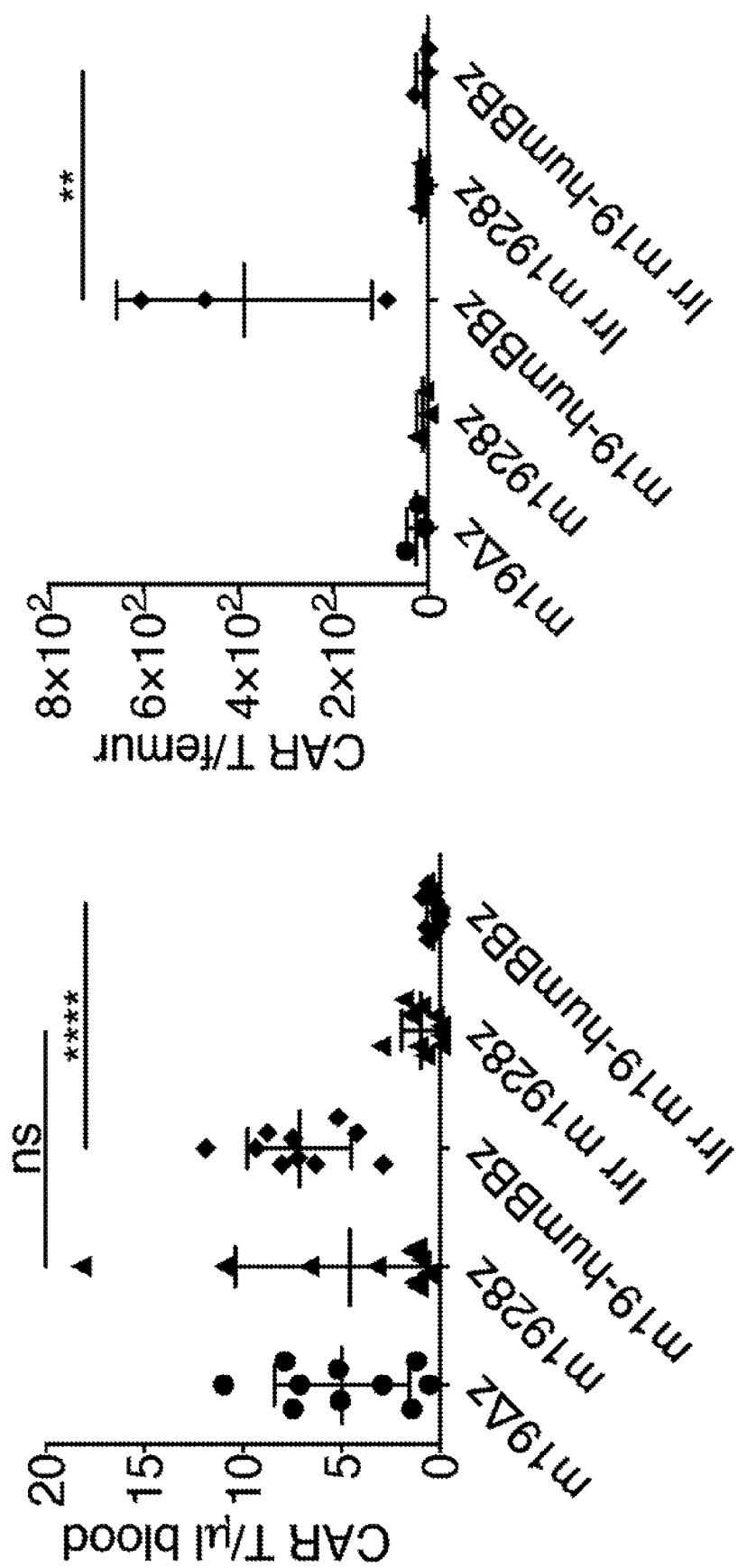
Figure 3C:
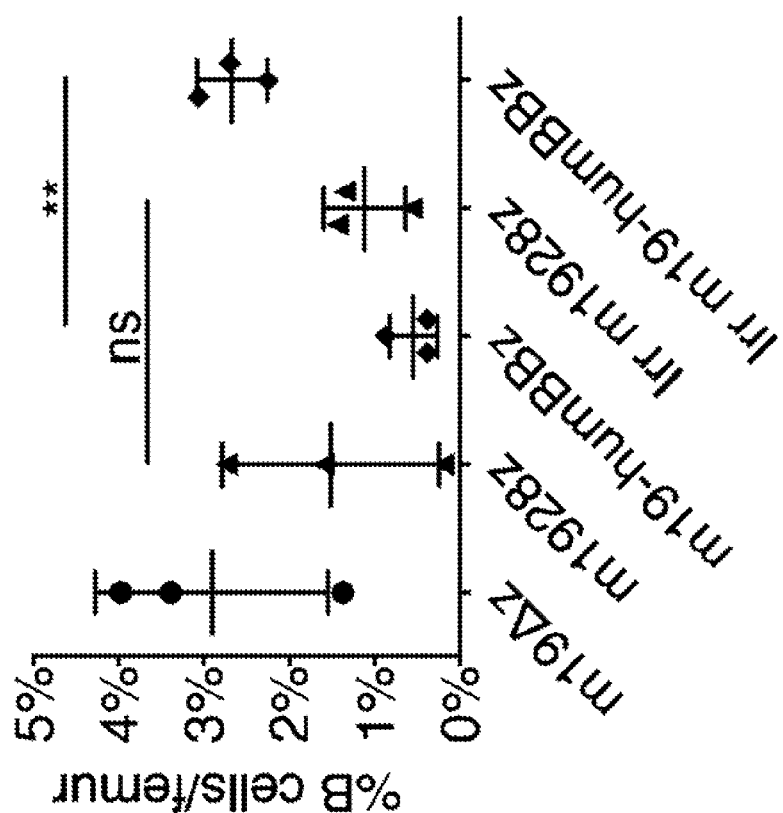
Figure 3C:
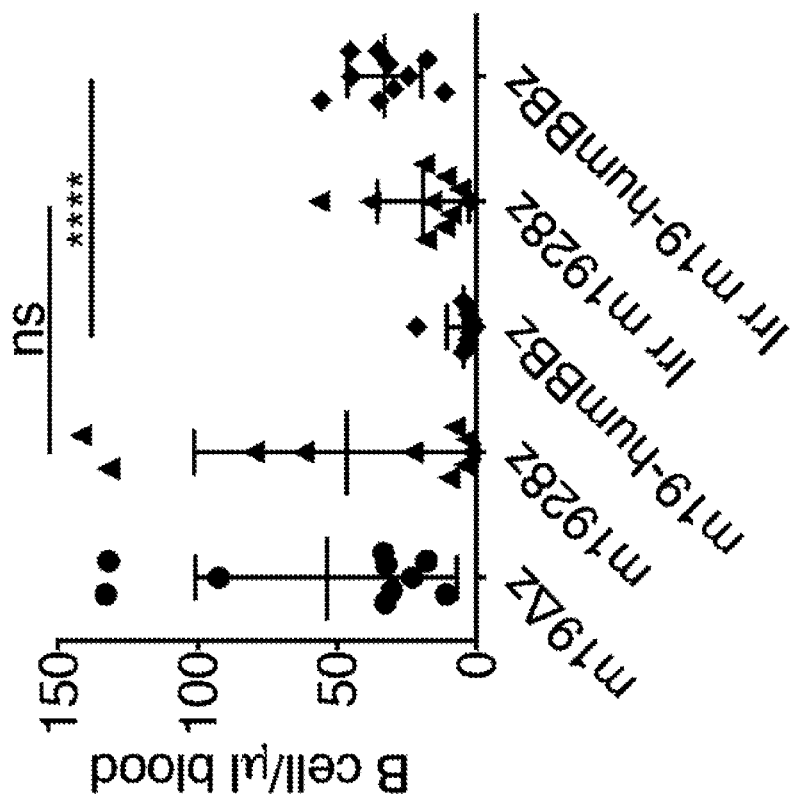
Figure 12:
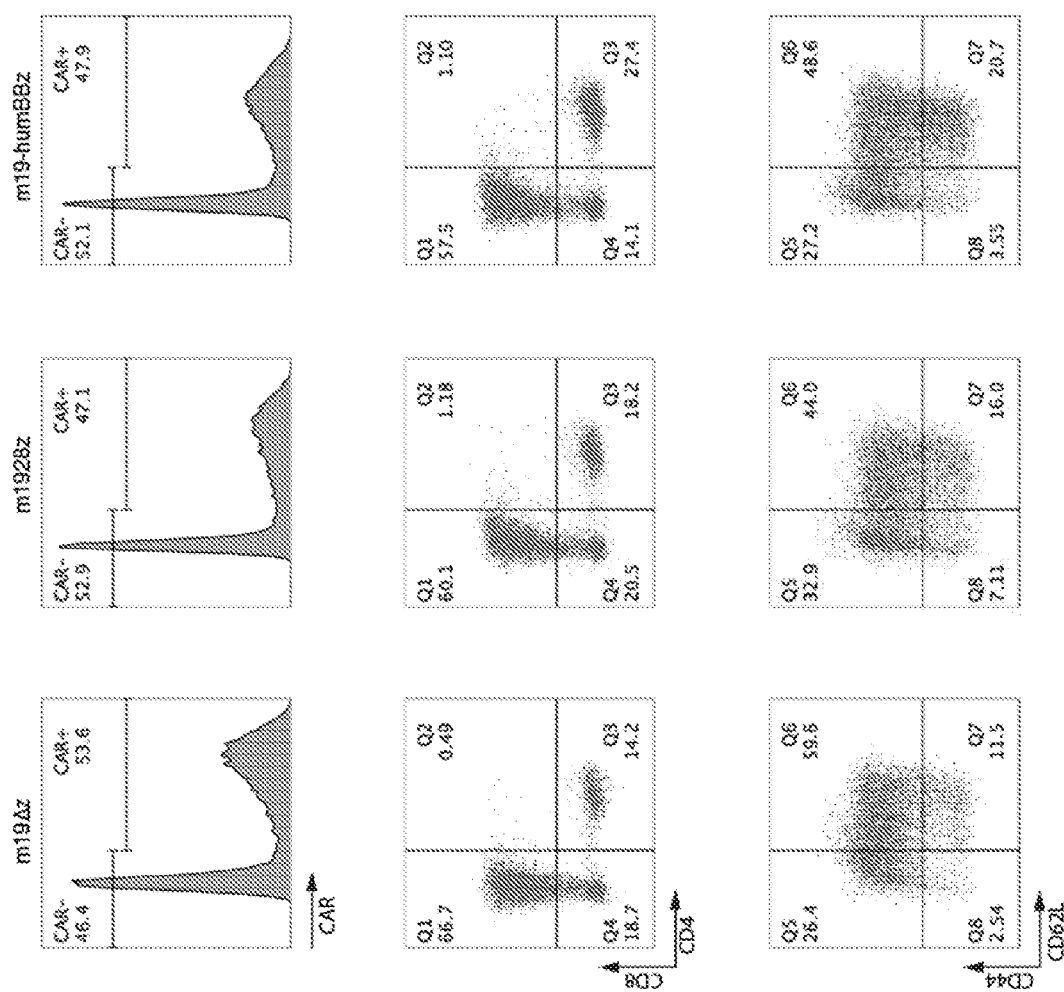

FIG. 12 shows transduction efficiency and immune phenotype of CAR T cells used in irradiated CAR T study (FIG. 3B-3C). Day 4 transduced cells were harvested, beads removed, stained with antibodies and subjected to flow cytometry. For transduction efficiency (Top panels), cells were pre-gated on single live cells. For immune phenotype (middle and bottom panels), cells were pre-gated on CD3+ CAR+ cells.

FIG. 13 shows differential gene expression of CD4+m19-humBBz CAR T cells. T cells with the m19z, m1928z, or m19-humBBz CAR were incubated with 3T3-mCD19 AAPC at 10:1 E:T ratio, FACS-sorted, and lysed to isolate RNA. Each group of CAR T cells was transduced, stimulated, and sorted independently in biologic triplicates. (A) PCA of mouse CD19-targeted CAR T cells stimulated with antigen. (B) Venn Diagram demonstrating the number of genes differentially expressed in m19-humBBz CAR T cells compared to m19z and m1928z CAR T cells. (C) GSEA demonstrates gene sets correlating to NF-κB regulatory pathways are differentially expressed in m19-humBBz CAR T cells versus m19z or m1928z CAR T cells.

Figure 5A:
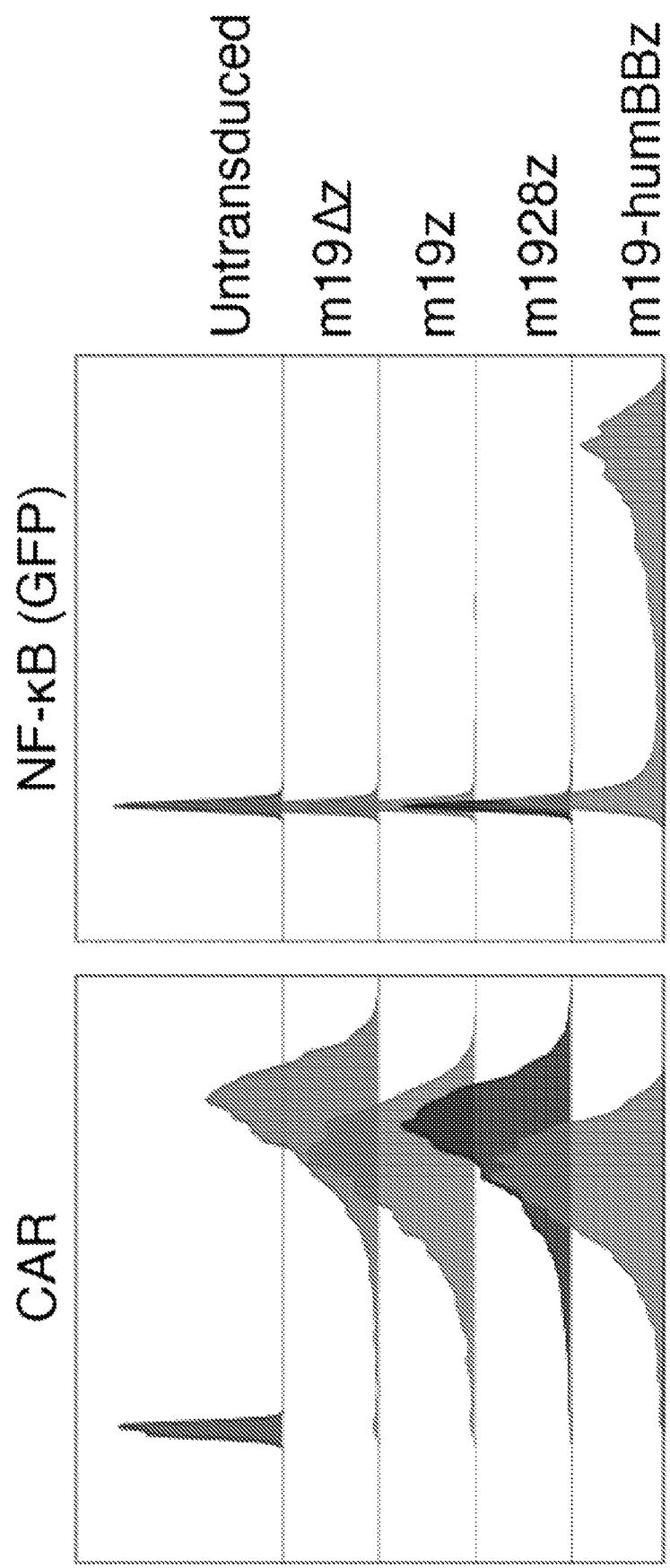
FIG. 5 shows NF-κB signaling regulates the viability and proliferation of 4-1BB-based CAR T cells. (A) CAR expression (mCherry) after transduction (left) and NF-κB upregulation (right) in NF-κB/293/GFP-Luc reporter cells. Reporter cells were transduced with mouse CD19-targeted CARs and NF-κB signaling was measured by flow cytometry for GFP. Data are representative of two independent experiments. (B) m19-humBBz CAR T cells have greater NF-κB signaling than m1928z CAR T cells after antigen stimulation. Three million CAR T cells derived from NF-κB-RE-luc transgenic mice were co-cultured with 3T3-mCD19 cells at a 10:1 ratio for 4 hr. Cell lysates were evaluated using a luciferase assay. Data are representative of 3 independent experiments in triplicate. (C) Amino acid sequences of human wild type (SEQ ID NO:1) and mutated (SEQ ID NOs:2-5) 4-1BB endodomains evaluated in hCD19-targeted CARs. Amino acid numbers of the 4-1BB endodomain are shown. (D) NF-κB signaling of hCD19 CAR transduced reporter cells. NF-κB/293/GFP-Luc reporter cells were retrovirally transduced with hCD19 targeted CARs. Percentages of GFP+ cells were measured by flow cytometry, which reflect NF-κB signaling. Data are from one experiment and done in triplicate. (E) Viability on day 16 and (F) proliferation of hCD19 targeted CAR T cells cultured in vitro. Human T cells were isolated from healthy donor PBMC at day 0. CAR T cells were harvested, beads removed and co-cultured with 3T3-hCD19 cells at 5:1 ratio for 2 weeks. Cell numbers were measured at indicated timepoints. (G) Cytotoxicity of hCD19 targeted CAR T cells. CAR T cells were co-cultured with 3T3-hCD19 cells at 10:1 ratio. Target cell killing was monitored by RTCA. For (E), (F) and (G), data are from one single experiment in triplicate. Data represent mean±SD for Figure B-F. Cytotoxicity curves show mean only. Cell expansion curves, two-way ANOVA; all other data, unpaired t test. *$p<0.05$; $p<0.01$; *$p<0.001$; ****$p<0.0001$; ns, not significant.
Figure 5B:
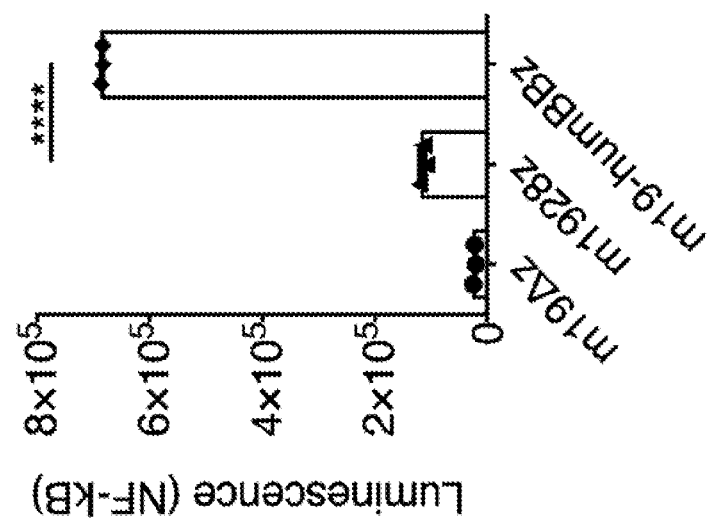
Figure 5E:
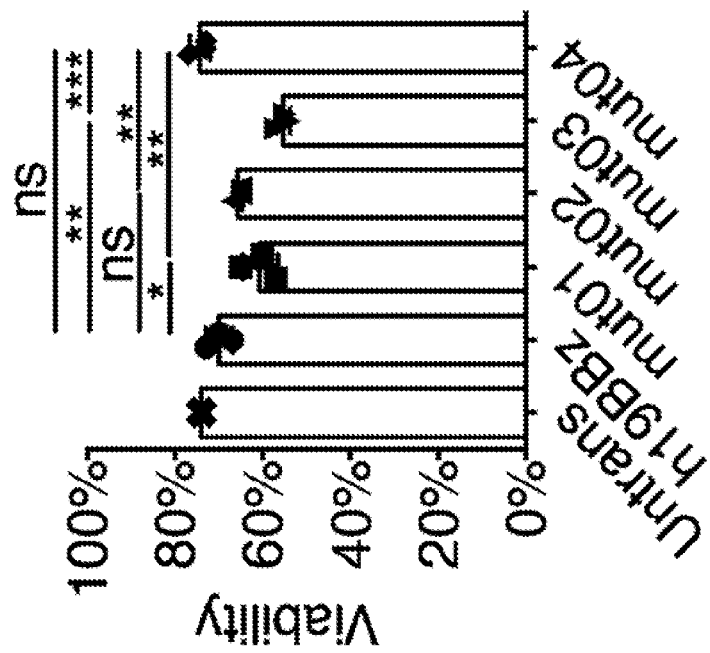
Figure 5D:
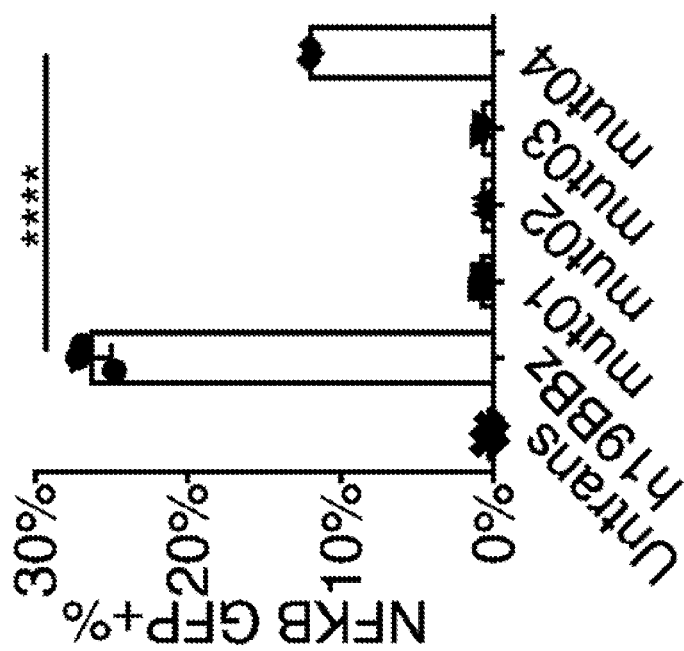
Figure 5G:
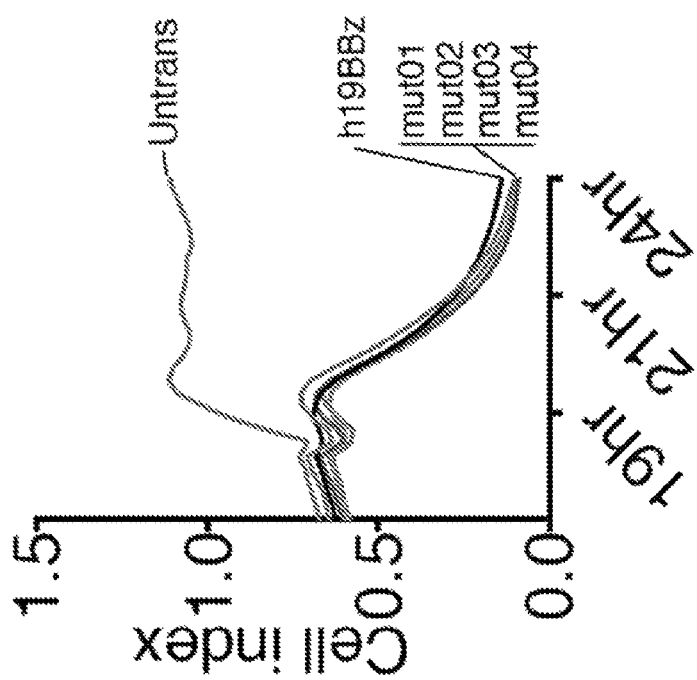
Figure 5F:
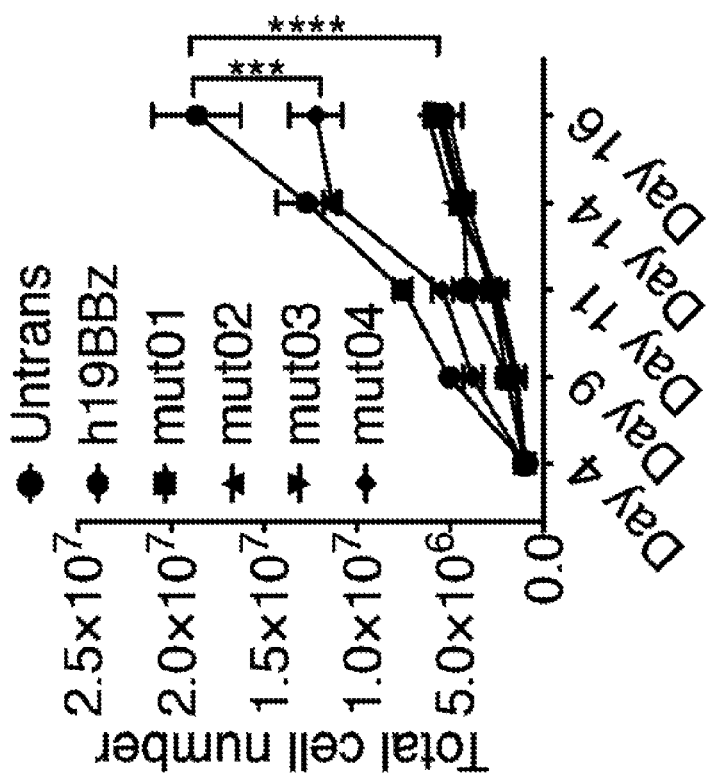
Figure 14:
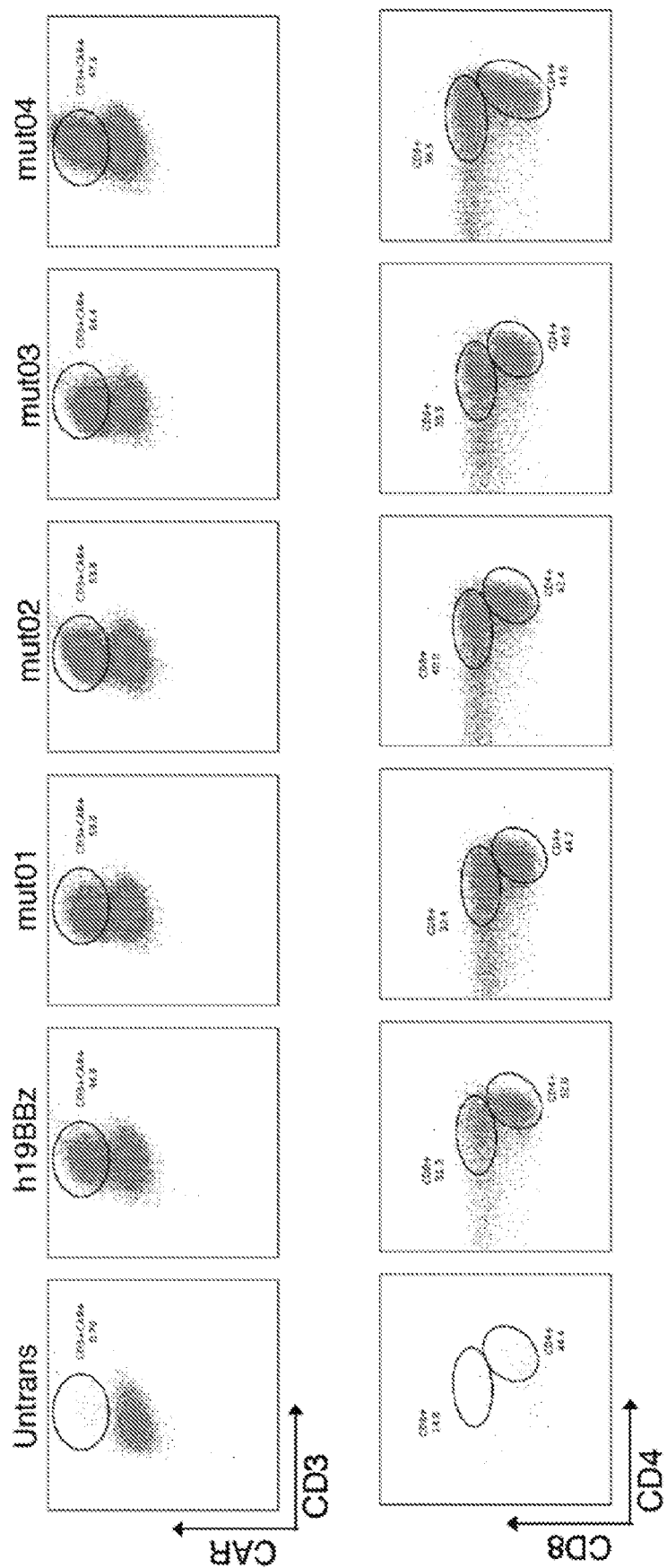

FIG. 14 shows CAR expression and CD4/CD8 subsets of human CD19 targeted CAR T cells for FIG. 5E-G. For CAR expression (top), cells were pre-gated on single live cells. For immune phenotype (bottom), cells were pre-gated on CD3+CAR+ cells.

Figure 6B:
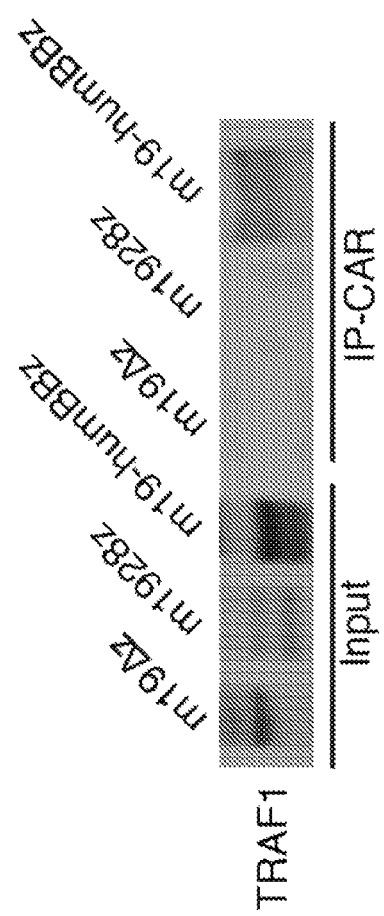
FIG. 6 shows TRAF1 inhibition negatively impacts NF-κB signaling and m19-humBBz CAR T cell function. (A) Effect of TRAF dominant negative (DN) proteins on m19-humBBz-induced NF-κB signaling in NF-κB/293/GFP-Luc reporter cells. Reporter cells were retrovirally transduced with cerulean-tagged TRAF1 DN, TRAF2 DN or TRAF3 DN constructs followed by transduction with m19-humBBz CAR. Cells were subjected to flow cytometry for NF-κB signaling, shown as GFP+ cells. Data are representative of two independent experiments. (B) Western blot of NF-κB/293 cell lysates before and after CAR immunoprecipitation. Cell lysates were prepared from CAR transduced NF-kB/293 cells, ligated to Protein L magnetic beads, enriched with a magnet, electrophoresed, and probed for TRAF1. Data are from one single experiment. (C) Viability and proliferation of wild type and Traf1$^{-/-}$ mCD19-targeted CAR T cells. CAR T cells were produced from wild type B6 mice or Traf1$^{-/-}$ mice and proliferation was evaluated by fold change from the initial cell number to final cell yield at Day 4. Cell viability was measured by trypan blue staining on an automated cell counter (BIO-RAD). Data are from a single experiment in triplicate. (D) In vivo B cell killing and CAR T persistence in the blood 2 weeks after CAR T transfer. CAR T cells prepared from wild type B6 or Traf1$^{-/-}$ mice were adoptively transferred at 3×10$^5$ dose into CTX pre-conditioned Thy1.1 mice. Blood was collected for flow cytometry. Counting beads were used to quantitate cell numbers. Each dot indicates one mouse. n=4 per group. All data, unpaired t test. *$p<0.05$; ***$p<0.001$; ns, not significant.
Figure 6C:
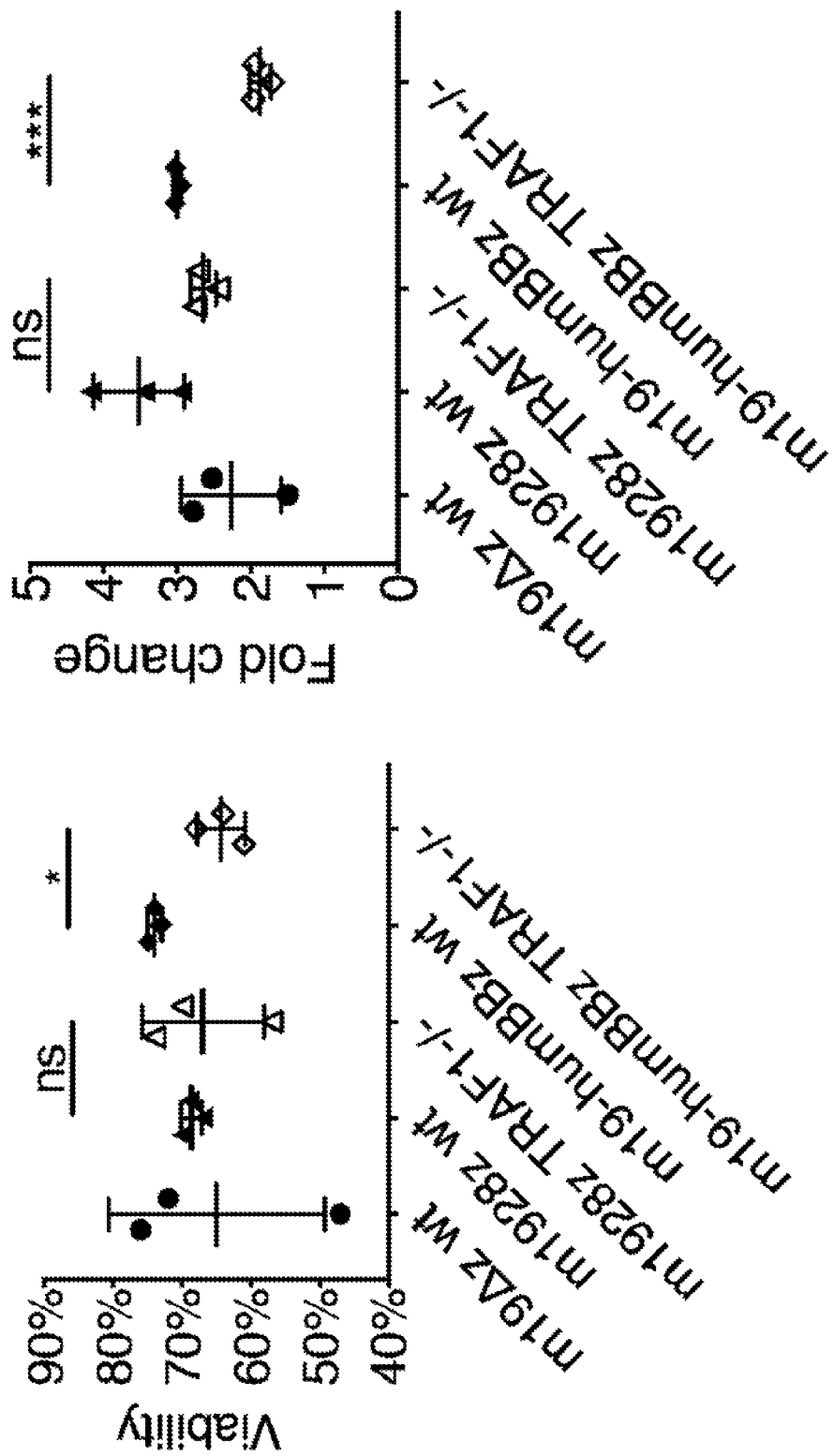
Figure 6D:
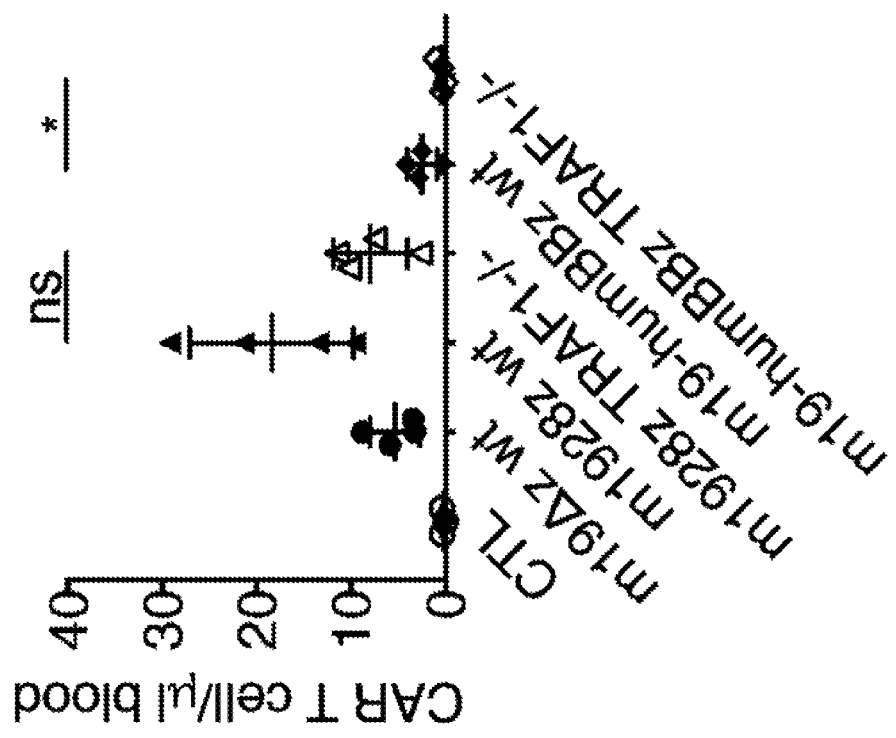
Figure 6D:
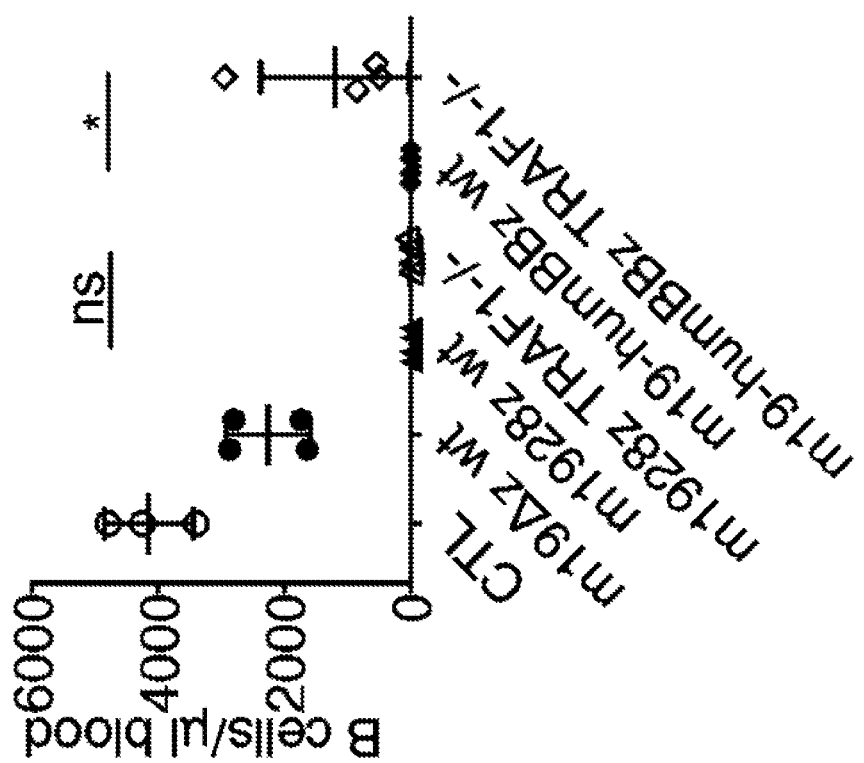
Figure 15:
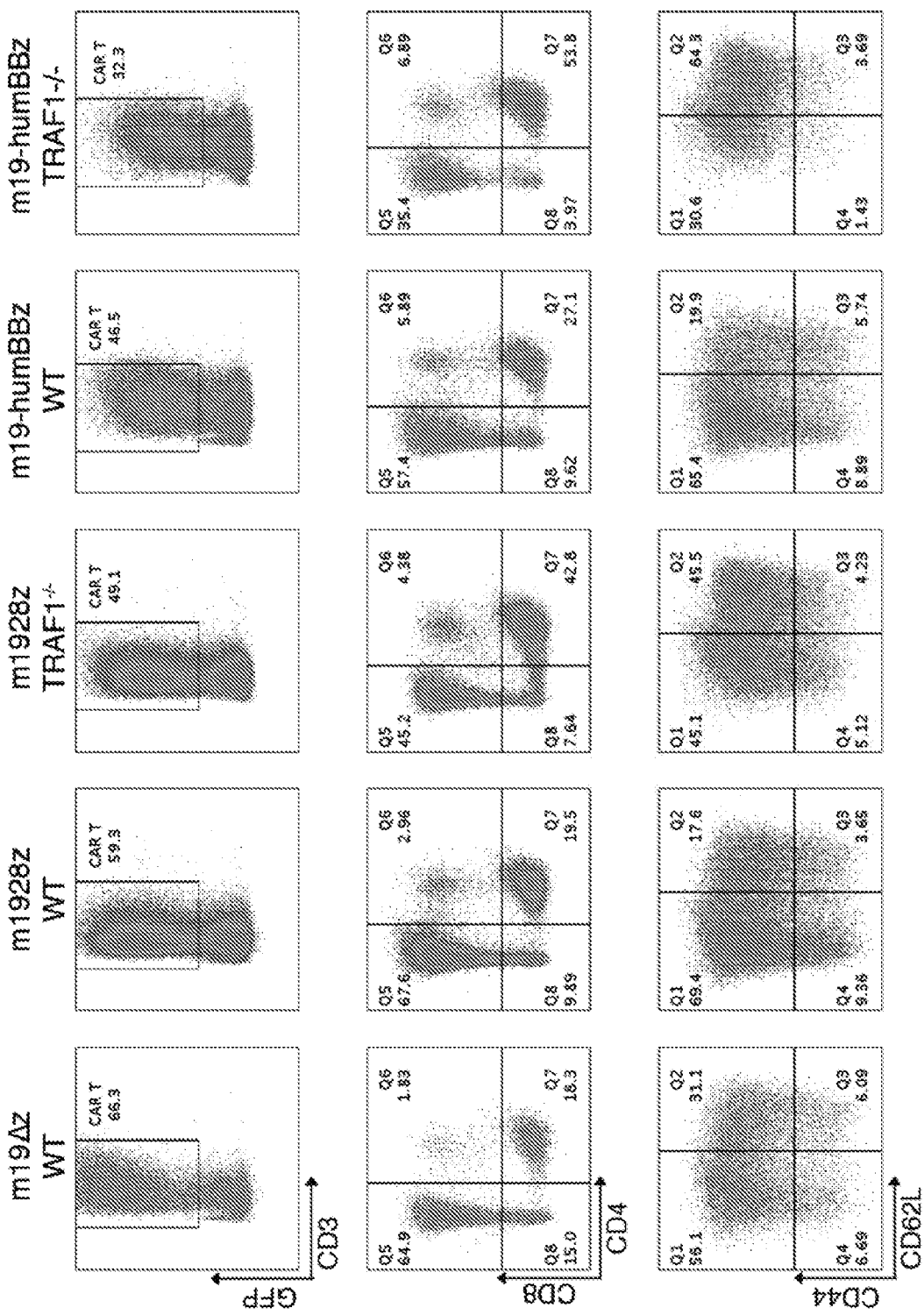

FIG. 15 shows transduction efficiency and immune phenotype of mCD19 targeted wild type (WT) and Traf1$^{-/-}$ CAR T cells used for in vivo study (FIG. 6D). Day 4 transduced cells were harvested, beads removed, stained with antibodies and subjected to flow cytometry. For transduction efficiency (top panel), cells were pre-gated on single live cells. For CD4/CD8 subsets (middle panel) and memory subsets (bottom panel) cells were pre-gated on single live CAR T (CD3+CAR+) cells.

FIG. 16 shows mutated m19-musBBz CAR T cells have increased NF-kB signaling, improved cytokine production, anti-apoptosis, and in vivo function. (A) NF-kB signaling in mCD19 targeted CAR T cells. CAR T cells derived from NF-k B-RE-luc transgenic mice were co-cultured with 3T3-mCD19 for 4 hr. Cell lysates were prepared and subjected to a luciferase assay. Bioluminescence was measured and correlates to NF-kB signaling. Data are representative of three independent experiments. (B) Intracellular IFNγ and (C) BCL-XL expression in CD8+ CAR T cells stimulated with 3T3-mCD19. Data are representative of two independent experiments done in triplicate. (D) CAR expression in T cells used for in vivo study below. Cells were pre-gated on single live cells. (E) B cells (CD19+B220+) in the blood 1 week after CAR T cells injection. (F) CAR T cells (CD3+ GFP+) in the blood 1 week after CAR T cells injection. (G) Donor T cells (CD3+Thy1.1+) in the blood 1 week after CAR T cells injection. (E-G) Each dot indicates one mouse (n=10 per group). Bar graph shown as mean±SD. All data, unpaired t test. *p<0.05; p<0.01; *p<0.001; ****p<0.0001; ns, not significant.

Figure 7A:
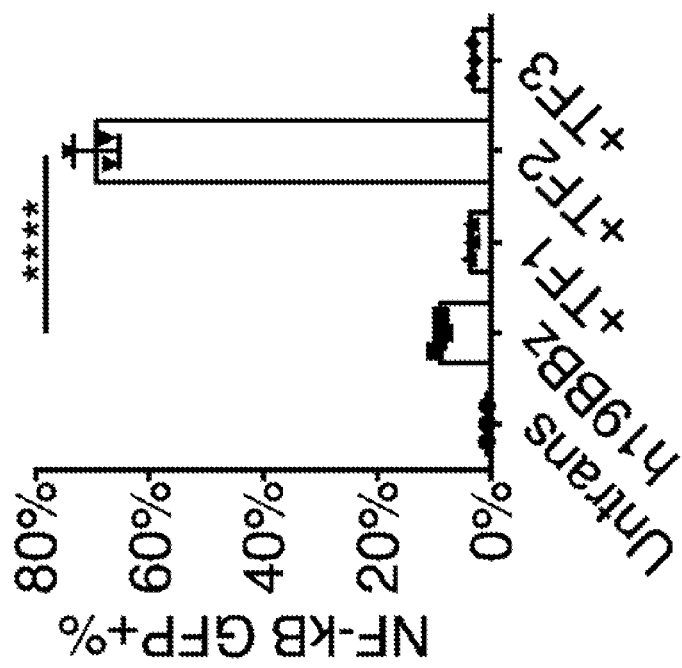
FIG. 7 shows TRAF2 over-expression modulates 4-1BB based human CAR T function. (A) NF-κB signaling in human CD19 CAR (h19BBz) transduced NF-κB293 reporter cells by increasing NF-κB. Cells were transduced with h19BBz CAR with or without TRAFs. NF-κB was measured by GFP. Data are from one experiment in triplicate. (B) Viability and (C) cell expansion of h19BBz CAR T cells with TRAF over-expression upon antigen stimulation. CAR T cells were co-cultured with 3T3-hCD19 at a 10:1 ratio and cell numbers and viability were measured daily for 3 days. (D) Cytotoxicity of h19BBz CAR T cells with TRAF over-expression. CAR T cells were co-cultured with 3T3-hCD19 at a 5:1 ratio. Target cell killing was monitored by RTCA. (E) Cytotoxicity of human CD33 targeted CAR (h33BBz) T cells with different scFvs. CAR T cells were co-cultured with CHO-hCD33 at a 10:1 ratio. Target cell killing was monitored by RTCA. (F) Fold change of h33BBz T cell production with or without TRAF2 co-transduction. CAR T cells were produced and proliferation was evaluated by fold change from the initial cell number to final cell yield. (G) h33BBz CAR T cell expansion in vitro upon antigen stimulation. CAR T cells were stained with proliferation dye and co-cultured with CHO-hCD33 at 10:1 E:T ratio for 4 days. Cell proliferation of CAR T cells was evaluated by flow cytometry (MFI of proliferation dye in CAR T population). All experiments other than (F) were done in triplicate. For (B), (C) and (D), data are one representative of 3 donors. For (F) and (G), data are from one single experiment. For (A) and (E), data are one representative of two independent experiments. Cytotoxicity data are shown as mean only, others shown as mean±SD. Untrans, untransduced; +TF1, CAR plus TRAF1; +TF2, CAR plus TRAF2; +TF3, CAR plus TRAF3. Bar graphs, unpaired t test; Viability and cell growth curves, two-way ANOVA; Cytotoxicity curves, Kolmogorov-Smirnov test. $p<0.01$; *$p<0.001$; ****$p<0.0001$; ns, not significant.
Figures 7B, 7C:
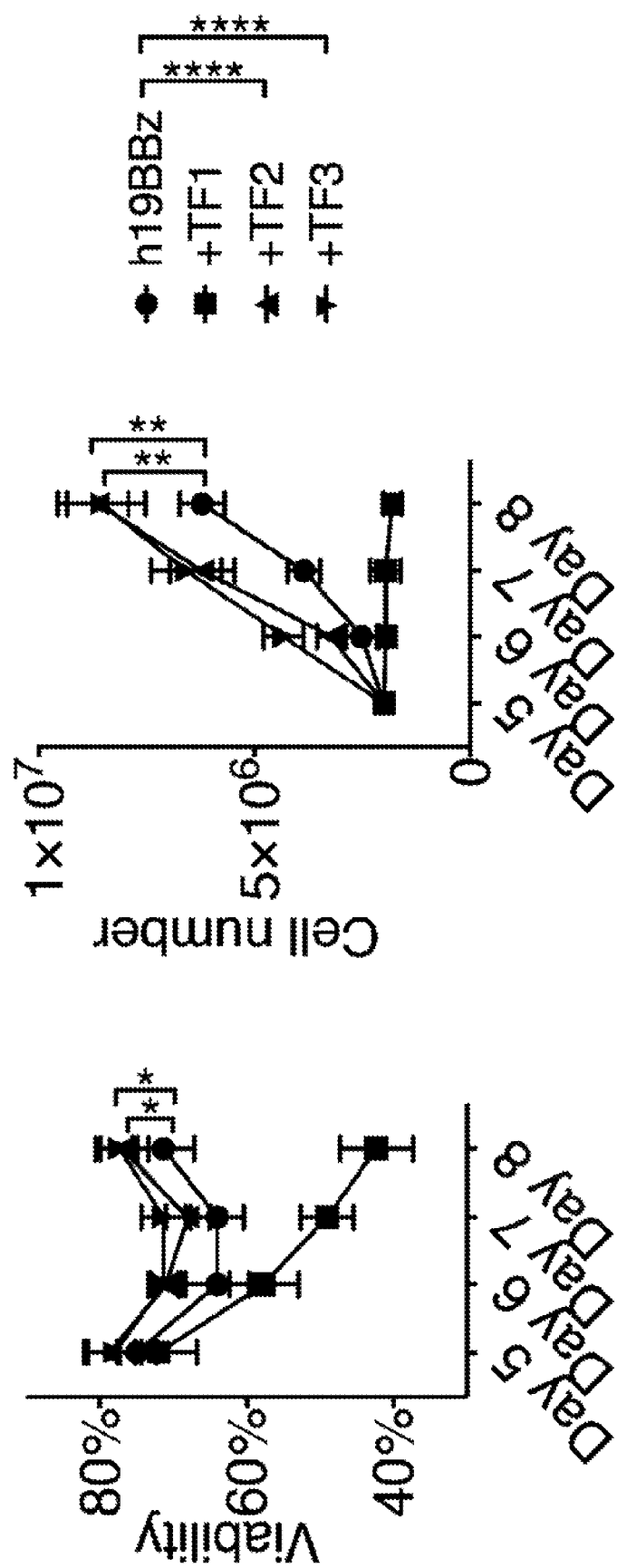
Figure 7D:
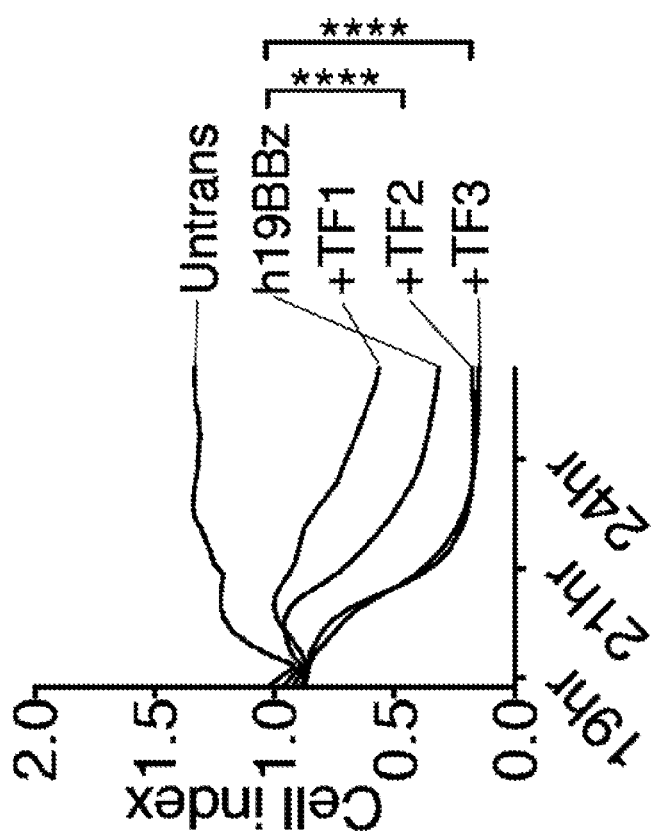

FIG. 17 shows TRAF and CAR co-expression in human CD19-targeted CAR T cells. (A) CAR and TRAF expression in hCD19 targeted CAR T cells before antigen stimulation for viability, proliferation, and cytotoxicity assays (FIG. 7B-D). Cells were pre-gated on single live cells. Data are one representative of 3 healthy donors. (B) CAR and TRAF expression in hCD19 CAR T cells 3 days after stimulation with 3T3-hCD19. Cells were pre-gated on single live cells. Data are from one experiment in triplicate. Numbers indicate percentages of gated cells. (C) Cytokine production. CAR T cells were activated on 3T3-hCD19 at 10:1 ratio. After 24 hr supernatant were harvested and cytokines were measured by ELLA. Bar graphs shown as mean±SD. Data are one representative of 3 different healthy donors in triplicate. All data, unpaired t test. ns, not significant.

FIG. 18 shows TRAF2 over-expressed h19BBz CAR T cells show similar in vivo efficacy to h19BBz CAR T cells in an aggressive leukemia model. NSG mice were implanted with leukemia by i.v. injecting $5 \times 10^5$ NALM6-GL cells. Four days later, mice were i.v. injected with $3 \times 10^5$-$1 \times 10^6$ CAR T cells. Blood samples were collected weekly. Leukemia burden was evaluated weekly using bioluminescence imaging. Survival was monitored. For (A-C), TRAF2 was co-transduced to make CAR T cells, n=15 total, and data are from one experiment. For (D-F), a bicistronic construct expressing CAR and TRAF2 was transduced to make CAR T cells. Survival data are pooled from two independent experiments (n=26), and counts are from one experiment. Each dot indicates a mouse. Survival curve, log rank test; all other data, unpaired t test. *p<0.05; **p<0.01; ns, not significant.

DETAILED DESCRIPTION

Disclosed herein are chimeric antigen receptor (CAR) polypeptides that have a costimulatory signaling region with one or more mutations in the cytoplasmic domains of CD28 and/or 4-1BB that enhance signaling that CAR-T cell function. Also disclosed are immune effector cells, such as T cells or Natural Killer (NK) cells, that are engineered to express these CARs. Therefore, also disclosed are methods for providing an anti-tumor immunity in a subject with TAA-expressing cancers that involves adoptive transfer of the disclosed immune effector cells engineered to express the disclosed CARs.

In some embodiments, the mutated costimulatory signaling region reduces CAR-T cell exhaustion. The CD28 domain includes 3 intracellular subdomains (YMNM (SEQ ID NO:26), PRRP (SEQ ID NO:27), and PYAP (SEQ ID NO:28)) that regulate signaling pathways post TCR-stimulation. In some embodiments, the disclosed CAR comprises mutation or deletion of one or more of these subdomains that enhances CAR-T cell function, e.g. reducing CAR-T cell exhaustion. In some embodiments, the disclosed CARs comprises altered phosphorylation at Y206 and/or Y218. In some embodiments, the disclosed CAR comprises an attenuating mutation at Y206, which will reduce the activity of the CAR. In some embodiments, the disclosed CAR comprises an attenuating mutation at Y218, which will reduce expression of the CAR. Any amino acid residue, such as alanine or phenylalanine, can be substituted for the tyrosine to achieve attenuation. In some embodiments, the tyrosine at Y206 and/or Y218 is substituted with a phosphomimetic residue. In some embodiments, the disclosed CAR substitution of Y206 with a phosphomimetic residue, which will increase the activity of the CAR. In some embodiments, the disclosed CAR comprises substitution of Y218 with a phosphomimetic residue, which will increase expression of the CAR. For example, the phosphomimetic residue can be phosphotyrosine. In some embodiments, a CAR may contain a combination of phosphomimetic amino acids and substitution(s) with non-phosphorylatable amino acids in different residues of the same CAR. For instance, a CAR may contain an alanine or phenylalanine substitution in Y209 and/or Y191 PLUS a phosphomimetic substitution in Y206 and/or Y218.

As disclosed herein, the level of nuclear factor kappaB (NFκB) signaling supported by chimeric antigen receptors (CARs) correlates with their function. Therefore, disclosed herein are chimeric antigen receptors (CARs) with enhanced NFκB signaling. As further disclosed herein, the co-stimulatory protein 41BB (CD137) activates NFκB signaling in T-cells through tumor necrosis factor receptor-associated factor (TRAF). Therefore, the disclosed CARs can comprise enhanced 41BB activation of TRAF.

In some cases, the disclosed CARs comprise two or more copies of 41BB. In some cases, the disclosed CARs comprise one or more 41BB domains with mutations that modulate binding to TRAF proteins, such as TRAF1, TRAF2, TRAF3, or any combination thereof. The TRAF proteins can have both positive and/or negative regulatory effects on NFκB. These bind directly to 41BB or bind to other proteins that are bound to 41BB. In some embodiments, the disclosed mutations enhance association of TRAFs that potentiate NFκB and reduce association of TRAFs the attenuate NFκB signaling.

The cytoplasmic domain of 41BB is responsible for binding to TRAF proteins. Therefore, in some embodiments, the disclosed CAR comprises two or more copies of the cytoplasmic domain of 41BB. Moreover, in order to provide finer control over TRAF activity, the cytoplasmic domain of 41BB can contain mutations that regulate TRAF association.

In some cases, the cytoplasmic domain of 41BB comprises the amino acid sequence KRGRKKLLY-IFKQPFMRPVQTTQEEDGCSCRFPEEEEGGCEL (SEQ ID NO:1). As disclosed herein, the regions of this domain responsible for TRAF binding are underlined in SEQ ID NO:1. Therefore, the disclosed CARs can comprise cytoplasmic domain(s) of 41BB having at least one mutation in these underlined sequences that enhance TRAF-binding and/or enhance NFκB signaling.

In some cases, the cytoplasmic domain of 41BB comprises the amino acid sequence KRGRKKLLY-IFKQPFMRPVQTTAAAAGCSCRFPEEEEGGCEL (SEQ ID NO:2, Mut01).

In some cases, the cytoplasmic domain of 41BB comprises the amino acid sequence KRGRKKLLY-IFKQPFMRPVQTTQEEDGCSCRFPAAAAGGCEL (SEQ ID NO:3, Mut02).

In some cases, the cytoplasmic domain of 41 BB comprises the amino acid sequence KRGRKKLLY-IFKQPFMRPVQTTAAAAGCSCRFPAAAAGGCEL (SEQ ID NO:4, Mut03).

In some cases, the cytoplasmic domain of 41 BB comprises the amino acid sequence

```
                                  (SEQ ID NO: 5, Mut04)
KRGRKKLLYIFKQPFMRPVQTTQEEDGCSCRFPEEEEGGCELKRGRKKLL

YIFKQPFMRPVQTTQEEDGCSCRFPEEEEGGCEL.
```

In some cases, the cytoplasmic domain of 41 BB comprises the amino acid sequence

```
                                  (SEQ ID NO: 6, Mut05)
KRGRKKLLYIFKQPFMRPVQTTAAAAGCSCRFPEEEEGGCELKRGRKKLL

YIFKQPFMRPVQTTQEEDGCSCRFPEEEEGGCEL.
```

In some cases, the cytoplasmic domain of 41 BB comprises the amino acid sequence

```
                                  (SEQ ID NO: 7, Mut06)
KRGRKKLLYIFKQPFMRPVQTTQEEDGCSCRFPAAAAGGCELKRGRKKLL

YIFKQPFMRPVQTTQEEDGCSCRFPEEEEGGCEL.
```

In some cases, the cytoplasmic domain of 41 BB comprises the amino acid sequence

```
                                  (SEQ ID NO: 8, Mut07)
KRGRKKLLYIFKQPFMRPVQTTQEEDGCSCRFPEEEEGGCELKRGRKKLL

YIFKQPFMRPVQTTAAAAGCSCRFPEEEEGGCEL.
```

In some cases, the cytoplasmic domain of 41 BB comprises the amino acid sequence

```
                                  (SEQ ID NO: 9, Mut08)
KRGRKKLLYIFKQPFMRPVQTTQEEDGCSCRFPEEEEGGCELKRGRKKLL

YIFKQPFMRPVQTTQEEDGCSCRFPAAAAGGCEL.
```

In some cases, the cytoplasmic domain of 41 BB comprises the amino acid sequence

```
                                  (SEQ ID NO: 10, Mut09)
KRGRKKLLYIFKQPFMRPVQTTAAAAGCSCRFPAAAAGGCELKRGRKK

LLYIFKQPFMRPVQTTQEEDGCSCRFPEEEEGGCEL.
```

In some cases, the cytoplasmic domain of 41 BB comprises the amino acid sequence (SEQ ID NO: 11, Mut10)
KRGRKKLLYIFKQPFMRPVQTT<u>AAAA</u>GCSCRFP<u>EEEE</u>GGCELKRGRKK LLYIFKQPFMRPVQTT<u>AAAA</u>GCSCRFP<u>EEEE</u>GGCEL.

In some cases, the cytoplasmic domain of 41 BB comprises the amino acid sequence (SEQ ID NO: 12, Mut11)
KRGRKKLLYIFKQPFMRPVQTT<u>AAAA</u>GCSCRFP<u>EEEE</u>GGCELKRGRKK LLYIFKQPFMRPVQTT<u>QEED</u>GCSCRFP<u>AAAA</u>GGCEL.

In some cases, the cytoplasmic domain of 41 BB comprises the amino acid sequence (SEQ ID NO: 13, Mut12)
KRGRKKLLYIFKQPFMRPVQTT<u>QEED</u>GCSCRFP<u>AAAA</u>GGCELKRGRKK LLYIFKQPFMRPVQTT<u>AAAA</u>GCSCRFP<u>EEEE</u>GGCEL.

In some cases, the cytoplasmic domain of 41 BB comprises the amino acid sequence (SEQ ID NO: 14, Mut13)
KRGRKKLLYIFKQPFMRPVQTT<u>QEED</u>GCSCRFP<u>AAAA</u>GGCELKRGRKK LLYIFKQPFMRPVQTT<u>QEED</u>GCSCRFP<u>AAAA</u>GGCEL.

In some cases, the cytoplasmic domain of 41 BB comprises the amino acid sequence (SEQ ID NO: 15, Mut14)
KRGRKKLLYIFKQPFMRPVQTT<u>QEED</u>GCSCRFP<u>EEEE</u>GGCELKRGRKK LLYIFKQPFMRPVQTT<u>AAAA</u>GCSCRFP<u>AAAA</u>GGCEL.

In some cases, the cytoplasmic domain of 41 BB comprises the amino acid sequence (SEQ ID NO: 16, Mut15)
KRGRKKLLYIFKQPFMRPVQTT<u>QEED</u>GCSCRFP<u>AAAA</u>GGCELKRGRKK LLYIFKQPFMRPVQTT<u>AAAA</u>GCSCRFP<u>AAAA</u>GGCEL.

In some cases, the cytoplasmic domain of 41 BB comprises the amino acid sequence (SEQ ID NO: 17, Mut16)
KRGRKKLLYIFKQPFMRPVQTT<u>AAAA</u>GCSCRFP<u>EEEE</u>GGCELKRGRKK LLYIFKQPFMRPVQTT<u>AAAA</u>GCSCRFP<u>AAAA</u>GGCEL.

In some cases, the cytoplasmic domain of 41 BB comprises the amino acid sequence (SEQ ID NO: 18, Mut17)
KRGRKKLLYIFKQPFMRPVQTT<u>AAAA</u>GCSCRFP<u>AAAA</u>GGCELKRGRKK LLYIFKQPFMRPVQTT<u>QEED</u>GCSCRFP<u>AAAA</u>GGCEL.

In some cases, the cytoplasmic domain of 41 BB comprises the amino acid sequence (SEQ ID NO: 19, Mut18)
KRGRKKLLYIFKQPFMRPVQTT<u>AAAA</u>GCSCRFP<u>AAAA</u>GGCELKRGRKK LLYIFKQPFMRPVQTT<u>AAAA</u>GCSCRFP<u>EEEE</u>GGCEL.

In some cases, the cytoplasmic domain of 41 BB comprises the amino acid sequence (SEQ ID NO: 20, Mut19)
KRGRKKLLYIFKQPFMRPVQTT<u>AAAA</u>GCSCRFP<u>AAAA</u>GGCELKRGRKK LLYIFKQPFMRPVQTT<u>AAAA</u>GCSCRFP<u>AAAA</u>GGCEL.

In some cases, the cytoplasmic domain of 41 BB comprises the amino acid sequence KRGRKKLLYIFKQPFMRPVQTT<u>QEED</u>GCSCRFP<u>EEEE</u>GGCEL (SEQ ID NO:1, but has at least 1, 2, 3, 4, 5, 6, or 7 amino acid substitutions of an underlined amino acid). In some cases, the amino acid substitution is a conservative substitution. In some embodiments, the amino acid is substituted for a non-acidic residue.

In some cases, the cytoplasmic domain of 41BB comprises the amino acid sequence

KRGRKKLLYIFKQPFMRPVQTT<u>$X_1X_2X_3X_4$</u>GCSCRFP<u>EEEE</u>GGCEL (SEQ ID NO:21, where $X_1$ is not Gln, wherein $X_2$ is not Glu, $X_3$ is not Glu, where $X_4$ is not Asp, or any combination thereof).

In some cases, the cytoplasmic domain of 41BB comprises the amino acid sequence

KRGRKKLLYIFKQPFMRPVQTT<u>QEED</u>GCSCRFP<u>$X_5X_6X_7X_8$</u>GGCEL (SEQ ID NO:22, wherein $X_5$ is not Glu, wherein $X_6$ is not Glu, wherein $X_7$ is not Glu, wherein $X_8$ is not Glu, or any combination thereof).

In some cases, the cytoplasmic domain of 41BB comprises the amino acid sequence

KRGRKKLLYIFKQPFMRPVQTT<u>$X_1X_2X_3X_4$</u>GCSCRFP<u>$X_5X_6X_7X_8$</u>GGCEL (SEQ ID NO:23, where $X_1$ is not Gln, wherein $X_2$ is not Glu, $X_3$ is not Glu, where $X_4$ is not Asp, wherein $X_5$ is not Glu, wherein $X_6$ is not Glu, wherein $X_7$ is not Glu, wherein $X_8$ is not Glu, or any combination thereof).

In some cases, the cytoplasmic domain of 41BB comprises the amino acid sequence

KRGRKKLLYIFKQPFMRPVQTT<u>$X_1X_2X_3X_4$</u>GCSCRFP<u>$X_5X_6X_7X_8$</u>

GGCELKRGRKKLLYIFKQPFMRPVQTT<u>$X_9X_{10}X_{11}X_{12}$</u>GCSCRFP

<u>$X_{13}X_{14}X_{15}X_{16}$</u>GGCEL (SEQ ID NO:24, where $X_1$ is not Gln, wherein $X_2$ is not Glu, $X_3$ is not Glu, where $X_4$ is not Asp, wherein $X_5$ is not Glu, wherein $X_6$ is not Glu, wherein $X_7$ is not Glu, wherein $X_8$ is not Glu, where $X_9$ is not Gln, wherein $X_{10}$ is not Glu, $X_{11}$ is not Glu, where $X_{12}$ is not Asp, wherein $X_{13}$ is not Glu, wherein $X_{14}$ is not Glu, wherein $X_{15}$ is not Glu, wherein $X_{16}$ is not Glu, or any combination thereof). In some cases, the cytoplasmic domain of 41BB comprises the amino acid sequence SEQ ID NO:24 having at least 2, 3, 4, 5, 6, 7, 8, 9, 10, 11, 12, 13, 14, or 15 amino acid substitutions, such as conservative amino acid substitutions.

CARs generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45). Disclosed herein is a chimeric antigen receptor (CAR) that can be that can be expressed in immune effector cells to enhance antitumor activity against cancers.

The disclosed CAR is generally made up of three domains: an ectodomain, a transmembrane domain, and an endodomain. The ectodomain comprises the TAA-binding region and is responsible for antigen recognition. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain an intracellular signaling domain (ISD) and a co-stimulatory signaling region (CSR). The disclosed CARs have a CSR comprising a mutated form of 41BB that enhances NFκB signaling.

In some embodiments, the disclosed CAR is defined by the formula:

SP-TAA-HG-TM-CSR-ISD;

wherein "SP" represents an optional signal peptide,
wherein "TAA" represents a TAA-binding region,
wherein "HG" represents an optional hinge domain,
wherein "TM" represents a transmembrane domain,
wherein "CSR" represents the co-stimulatory signaling region,
wherein "ISD" represents an intracellular signaling domain, and
wherein "-" represents a peptide bond or linker.

Additional CAR constructs are described, for example, in Fresnak A D, et al. Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

TRUCKs (T cells redirected for universal cytokine killing) co-express a chimeric antigen receptor (CAR) and an antitumor cytokine. Cytokine expression may be constitutive or induced by T cell activation. Targeted by CAR specificity, localized production of pro-inflammatory cytokines recruits endogenous immune cells to tumor sites and may potentiate an antitumor response.

Universal, allogeneic CAR T cells are engineered to no longer express endogenous T cell receptor (TCR) and/or major histocompatibility complex (MHC) molecules, thereby preventing graft-versus-host disease (GVHD) or rejection, respectively.

Self-driving CARs co-express a CAR and a chemokine receptor, which binds to a tumor ligand, thereby enhancing tumor homing.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

Marked CAR T cells express a CAR plus a tumor epitope to which an existing monoclonal antibody agent binds. In the setting of intolerable adverse effects, administration of the monoclonal antibody clears the CAR T cells and alleviates symptoms with no additional off-tumor effects.

A tandem CAR (TanCAR) T cell expresses a single CAR consisting of two linked single-chain variable fragments (scFvs) that have different affinities fused to intracellular co-stimulatory domain(s) and a CD3ζ domain. TanCAR T cell activation is achieved only when target cells co-express both targets.

A dual CAR T cell expresses two separate CARs with different ligand binding targets; one CAR includes only the CD3ζ domain and the other CAR includes only the co-stimulatory domain(s). Dual CAR T cell activation requires co-expression of both targets on the tumor.

A safety CAR (sCAR) consists of an extracellular scFv fused to an intracellular inhibitory domain. sCAR T cells co-expressing a standard CAR become activated only when encountering target cells that possess the standard CAR target but lack the sCAR target.

The antigen recognition domain of the disclosed CAR is usually an scFv. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ, CD3δ, CD3γ, CD3ε, CD32 (Fc gamma RIIa), DAP10, DAP12, CD79a, CD79b, FcγRIγ, FcγRIIIγ, FcεRIβ (FCERIB), and FcεRIγ (FCERIG).

In particular embodiments, the intracellular signaling domain is derived from CD3 zeta (CD3ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s) useful in the context of the CAR of the invention. For example, the cytoplasmic domain of the CAR can comprise a CD3ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 41BB (CD137), OX40, CD30, CD40, ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, and NKG2D. Thus, while the CAR is exemplified primarily with a mutated 41 BB as the co-stimulatory signaling element, other costimulatory elements can be used in combination.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

Tables 1 and 2 below provide some example combinations of TAA-binding region, co-stimulatory signaling regions, and intracellular signaling domain that can occur in the disclosed CARs.

TABLE 1

Second Generation CARs

| ScFv | Co-stimulatory Signal | Signal Domain |
|---|---|---|
| TAA | 41BB/CD28* | CD8 |
| TAA | 41BB/CD28* | CD3ζ |
| TAA | 41BB/CD28* | CD3δ |
| TAA | 41BB/CD28* | CD3γ |
| TAA | 41BB/CD28* | CD3ε |
| TAA | 41BB/CD28* | FcγRI-γ |
| TAA | 41BB/CD28* | FcγRIII-γ |
| TAA | 41BB/CD28* | FcεRIβ |
| TAA | 41BB/CD28* | FcεRIγ |
| TAA | 41BB/CD28* | DAP10 |
| TAA | 41BB/CD28* | DAP12 |
| TAA | 41BB/CD28* | CD32 |
| TAA | 41BB/CD28* | CD79a |
| TAA | 41BB/CD28* | CD79b |

41BB/CD28* = mutated 41BB alone or mutated 41BB in combination with mutated CD28 co-stimulatory domain

TABLE 2

Third Generation CARs

| ScFv | Co-stimulatory Signal | Co-stimulatory Signal | Signal Domain |
|---|---|---|---|
| TAA | 41BB/CD28* | 41BB/CD28* | CD8 |
| TAA | 41BB/CD28* | 41BB/CD28* | CD3ζ |

TABLE 2-continued

Third Generation CARs

| ScFv | Co-stimulatory Signal | Co-stimulatory Signal | Signal Domain |
|---|---|---|---|
| TAA | 41BB/CD28* | 41BB/CD28* | CD3δ |
| TAA | 41BB/CD28* | 41BB/CD28* | CD3γ |
| TAA | 41BB/CD28* | 41BB/CD28* | CD3ε |
| TAA | 41BB/CD28* | 41BB/CD28* | FcγRI-γ |
| TAA | 41BB/CD28* | 41BB/CD28* | FcγRIII-γ |
| TAA | 41BB/CD28* | 41BB/CD28* | FcεRIβ |
| TAA | 41BB/CD28* | 41BB/CD28* | FcεRIγ |
| TAA | 41BB/CD28* | 41BB/CD28* | DAP10 |
| TAA | 41BB/CD28* | 41BB/CD28* | DAP12 |
| TAA | 41BB/CD28* | 41BB/CD28* | CD32 |
| TAA | 41BB/CD28* | 41BB/CD28* | CD79a |
| TAA | 41BB/CD28* | 41BB/CD28* | CD79b |
| TAA | 41BB/CD28* | CD28 | CD8 |
| TAA | 41BB/CD28* | CD28 | CD3ζ |
| TAA | 41BB/CD28* | CD28 | CD3δ |
| TAA | 41BB/CD28* | CD28 | CD3γ |
| TAA | 41BB/CD28* | CD28 | CD3ε |
| TAA | 41BB/CD28* | CD28 | FcγRI-γ |
| TAA | 41BB/CD28* | CD28 | FcγRIII-γ |
| TAA | 41BB/CD28* | CD28 | FcεRIβ |
| TAA | 41BB/CD28* | CD28 | FcεRIγ |
| TAA | 41BB/CD28* | CD28 | DAP10 |
| TAA | 41BB/CD28* | CD28 | DAP12 |
| TAA | 41BB/CD28* | CD28 | CD32 |
| TAA | 41BB/CD28* | CD28 | CD79a |
| TAA | 41BB/CD28* | CD28 | CD79b |
| TAA | 41BB/CD28* | CD8 | CD8 |
| TAA | 41BB/CD28* | CD8 | CD3ζ |
| TAA | 41BB/CD28* | CD8 | CD3δ |
| TAA | 41BB/CD28* | CD8 | CD3γ |
| TAA | 41BB/CD28* | CD8 | CD3ε |
| TAA | 41BB/CD28* | CD8 | FcγRI-γ |
| TAA | 41BB/CD28* | CD8 | FcγRIII-γ |
| TAA | 41BB/CD28* | CD8 | FcεRIβ |
| TAA | 41BB/CD28* | CD8 | FcεRIγ |
| TAA | 41BB/CD28* | CD8 | DAP10 |
| TAA | 41BB/CD28* | CD8 | DAP12 |
| TAA | 41BB/CD28* | CD8 | CD32 |
| TAA | 41BB/CD28* | CD8 | CD79a |
| TAA | 41BB/CD28* | CD8 | CD79b |
| TAA | 41BB/CD28* | CD4 | CD8 |
| TAA | 41BB/CD28* | CD4 | CD3ζ |
| TAA | 41BB/CD28* | CD4 | CD3δ |
| TAA | 41BB/CD28* | CD4 | CD3γ |
| TAA | 41BB/CD28* | CD4 | CD3ε |
| TAA | 41BB/CD28* | CD4 | FcγRI-γ |
| TAA | 41BB/CD28* | CD4 | FcγRIII-γ |
| TAA | 41BB/CD28* | CD4 | FcεRIβ |
| TAA | 41BB/CD28* | CD4 | FcεRIγ |
| TAA | 41BB/CD28* | CD4 | DAP10 |
| TAA | 41BB/CD28* | CD4 | DAP12 |
| TAA | 41BB/CD28* | CD4 | CD32 |
| TAA | 41BB/CD28* | CD4 | CD79a |
| TAA | 41BB/CD28* | CD4 | CD79b |
| TAA | 41BB/CD28* | b2c | CD8 |
| TAA | 41BB/CD28* | b2c | CD3ζ |
| TAA | 41BB/CD28* | b2c | CD3δ |
| TAA | 41BB/CD28* | b2c | CD3γ |
| TAA | 41BB/CD28* | b2c | CD3ε |
| TAA | 41BB/CD28* | b2c | FcγRI-γ |
| TAA | 41BB/CD28* | b2c | FcγRIII-γ |
| TAA | 41BB/CD28* | b2c | FcεRIβ |
| TAA | 41BB/CD28* | b2c | FcεRIγ |
| TAA | 41BB/CD28* | b2c | DAP10 |
| TAA | 41BB/CD28* | b2c | DAP12 |
| TAA | 41BB/CD28* | b2c | CD32 |
| TAA | 41BB/CD28* | b2c | CD79a |
| TAA | 41BB/CD28* | b2c | CD79b |
| TAA | 41BB/CD28* | CD137/41BB | CD8 |
| TAA | 41BB/CD28* | CD137/41BB | CD3ζ |
| TAA | 41BB/CD28* | CD137/41BB | CD3δ |
| TAA | 41BB/CD28* | CD137/41BB | CD3γ |
| TAA | 41BB/CD28* | CD137/41BB | CD3ε |
| TAA | 41BB/CD28* | CD137/41BB | FcγRI-γ |
| TAA | 41BB/CD28* | CD137/41BB | FcγRIII-γ |
| TAA | 41BB/CD28* | CD137/41BB | FcεRIβ |
| TAA | 41BB/CD28* | CD137/41BB | FcεRIγ |
| TAA | 41BB/CD28* | CD137/41BB | DAP10 |
| TAA | 41BB/CD28* | CD137/41BB | DAP12 |
| TAA | 41BB/CD28* | CD137/41BB | CD32 |
| TAA | 41BB/CD28* | CD137/41BB | CD79a |
| TAA | 41BB/CD28* | CD137/41BB | CD79b |
| TAA | 41BB/CD28* | ICOS | CD8 |
| TAA | 41BB/CD28* | ICOS | CD3ζ |
| TAA | 41BB/CD28* | ICOS | CD3δ |
| TAA | 41BB/CD28* | ICOS | CD3γ |
| TAA | 41BB/CD28* | ICOS | CD3ε |
| TAA | 41BB/CD28* | ICOS | FcγRI-γ |
| TAA | 41BB/CD28* | ICOS | FcγRIII-γ |
| TAA | 41BB/CD28* | ICOS | FcεRIβ |
| TAA | 41BB/CD28* | ICOS | FcεRIγ |
| TAA | 41BB/CD28* | ICOS | DAP10 |
| TAA | 41BB/CD28* | ICOS | DAP12 |
| TAA | 41BB/CD28* | ICOS | CD32 |
| TAA | 41BB/CD28* | ICOS | CD79a |
| TAA | 41BB/CD28* | ICOS | CD79b |
| TAA | 41BB/CD28* | CD27 | CD8 |
| TAA | 41BB/CD28* | CD27 | CD3ζ |
| TAA | 41BB/CD28* | CD27 | CD3δ |
| TAA | 41BB/CD28* | CD27 | CD3γ |
| TAA | 41BB/CD28* | CD27 | CD3ε |
| TAA | 41BB/CD28* | CD27 | FcγRI-γ |
| TAA | 41BB/CD28* | CD27 | FcγRIII-γ |
| TAA | 41BB/CD28* | CD27 | FcεRIβ |
| TAA | 41BB/CD28* | CD27 | FcεRIγ |
| TAA | 41BB/CD28* | CD27 | DAP10 |
| TAA | 41BB/CD28* | CD27 | DAP12 |
| TAA | 41BB/CD28* | CD27 | CD32 |
| TAA | 41BB/CD28* | CD27 | CD79a |
| TAA | 41BB/CD28* | CD27 | CD79b |
| TAA | 41BB/CD28* | CD28δ | CD8 |
| TAA | 41BB/CD28* | CD28δ | CD3ζ |
| TAA | 41BB/CD28* | CD28δ | CD3δ |
| TAA | 41BB/CD28* | CD28δ | CD3γ |
| TAA | 41BB/CD28* | CD28δ | CD3ε |
| TAA | 41BB/CD28* | CD28δ | FcγRI-γ |
| TAA | 41BB/CD28* | CD28δ | FcγRIII-γ |
| TAA | 41BB/CD28* | CD28δ | FcεRIβ |
| TAA | 41BB/CD28* | CD28δ | FcεRIγ |
| TAA | 41BB/CD28* | CD28δ | DAP10 |
| TAA | 41BB/CD28* | CD28δ | DAP12 |
| TAA | 41BB/CD28* | CD28δ | CD32 |
| TAA | 41BB/CD28* | CD28δ | CD79a |
| TAA | 41BB/CD28* | CD28δ | CD79b |
| TAA | 41BB/CD28* | CD80 | CD8 |
| TAA | 41BB/CD28* | CD80 | CD3ζ |
| TAA | 41BB/CD28* | CD80 | CD3δ |
| TAA | 41BB/CD28* | CD80 | CD3γ |
| TAA | 41BB/CD28* | CD80 | CD3ε |
| TAA | 41BB/CD28* | CD80 | FcγRI-γ |
| TAA | 41BB/CD28* | CD80 | FcγRIII-γ |
| TAA | 41BB/CD28* | CD80 | FcεRIβ |
| TAA | 41BB/CD28* | CD80 | FcεRIγ |
| TAA | 41BB/CD28* | CD80 | DAP10 |
| TAA | 41BB/CD28* | CD80 | DAP12 |
| TAA | 41BB/CD28* | CD80 | CD32 |
| TAA | 41BB/CD28* | CD80 | CD79a |
| TAA | 41BB/CD28* | CD80 | CD79b |
| TAA | 41BB/CD28* | CD86 | CD8 |
| TAA | 41BB/CD28* | CD86 | CD3ζ |
| TAA | 41BB/CD28* | CD86 | CD3δ |
| TAA | 41BB/CD28* | CD86 | CD3γ |
| TAA | 41BB/CD28* | CD86 | CD3ε |
| TAA | 41BB/CD28* | CD86 | FcγRI-γ |
| TAA | 41BB/CD28* | CD86 | FcγRIII-γ |
| TAA | 41BB/CD28* | CD86 | FcεRIβ |
| TAA | 41BB/CD28* | CD86 | FcεRIγ |
| TAA | 41BB/CD28* | CD86 | DAP10 |
| TAA | 41BB/CD28* | CD86 | DAP12 |
| TAA | 41BB/CD28* | CD86 | CD32 |

TABLE 2-continued

Third Generation CARs

| ScFv | Co-stimulatory Signal | Co-stimulatory Signal | Signal Domain |
|---|---|---|---|
| TAA | 41BB/CD28* | CD86 | CD79a |
| TAA | 41BB/CD28* | CD86 | CD79b |
| TAA | 41BB/CD28* | OX40 | CD8 |
| TAA | 41BB/CD28* | OX40 | CD3ζ |
| TAA | 41BB/CD28* | OX40 | CD3δ |
| TAA | 41BB/CD28* | OX40 | CD3γ |
| TAA | 41BB/CD28* | OX40 | CD3ε |
| TAA | 41BB/CD28* | OX40 | FcγRI-γ |
| TAA | 41BB/CD28* | OX40 | FcγRIII-γ |
| TAA | 41BB/CD28* | OX40 | FcεRIβ |
| TAA | 41BB/CD28* | OX40 | FcεRIγ |
| TAA | 41BB/CD28* | OX40 | DAP10 |
| TAA | 41BB/CD28* | OX40 | DAP12 |
| TAA | 41BB/CD28* | OX40 | CD32 |
| TAA | 41BB/CD28* | OX40 | CD79a |
| TAA | 41BB/CD28* | OX40 | CD79b |
| TAA | 41BB/CD28* | DAP10 | CD8 |
| TAA | 41BB/CD28* | DAP10 | CD3ζ |
| TAA | 41BB/CD28* | DAP10 | CD3δ |
| TAA | 41BB/CD28* | DAP10 | CD3γ |
| TAA | 41BB/CD28* | DAP10 | CD3ε |
| TAA | 41BB/CD28* | DAP10 | FcγRI-γ |
| TAA | 41BB/CD28* | DAP10 | FcγRIII-γ |
| TAA | 41BB/CD28* | DAP10 | FcεRIβ |
| TAA | 41BB/CD28* | DAP10 | FcεRIγ |
| TAA | 41BB/CD28* | DAP10 | DAP10 |
| TAA | 41BB/CD28* | DAP10 | DAP12 |
| TAA | 41BB/CD28* | DAP10 | CD32 |
| TAA | 41BB/CD28* | DAP10 | CD79a |
| TAA | 41BB/CD28* | DAP10 | CD79b |
| TAA | 41BB/CD28* | DAP12 | CD8 |
| TAA | 41BB/CD28* | DAP12 | CD3ζ |
| TAA | 41BB/CD28* | DAP12 | CD3δ |
| TAA | 41BB/CD28* | DAP12 | CD3γ |
| TAA | 41BB/CD28* | DAP12 | CD3ε |
| TAA | 41BB/CD28* | DAP12 | FcγRI-γ |
| TAA | 41BB/CD28* | DAP12 | FcγRIII-γ |
| TAA | 41BB/CD28* | DAP12 | FcεRIβ |
| TAA | 41BB/CD28* | DAP12 | FcεRIγ |
| TAA | 41BB/CD28* | DAP12 | DAP10 |
| TAA | 41BB/CD28* | DAP12 | DAP12 |
| TAA | 41BB/CD28* | DAP12 | CD32 |
| TAA | 41BB/CD28* | DAP12 | CD79a |
| TAA | 41BB/CD28* | DAP12 | CD79b |
| TAA | 41BB/CD28* | MyD88 | CD8 |
| TAA | 41BB/CD28* | MyD88 | CD3ζ |
| TAA | 41BB/CD28* | MyD88 | CD3δ |
| TAA | 41BB/CD28* | MyD88 | CD3γ |
| TAA | 41BB/CD28* | MyD88 | CD3ε |
| TAA | 41BB/CD28* | MyD88 | FcγRI-γ |
| TAA | 41BB/CD28* | MyD88 | FcγRIII-γ |
| TAA | 41BB/CD28* | MyD88 | FcεRIβ |
| TAA | 41BB/CD28* | MyD88 | FcεRIγ |
| TAA | 41BB/CD28* | MyD88 | DAP10 |
| TAA | 41BB/CD28* | MyD88 | DAP12 |
| TAA | 41BB/CD28* | MyD88 | CD32 |
| TAA | 41BB/CD28* | MyD88 | CD79a |
| TAA | 41BB/CD28* | MyD88 | CD79b |
| TAA | 41BB/CD28* | CD7 | CD8 |
| TAA | 41BB/CD28* | CD7 | CD3ζ |
| TAA | 41BB/CD28* | CD7 | CD3δ |
| TAA | 41BB/CD28* | CD7 | CD3γ |
| TAA | 41BB/CD28* | CD7 | CD3ε |
| TAA | 41BB/CD28* | CD7 | FcγRI-γ |
| TAA | 41BB/CD28* | CD7 | FcγRIII-γ |
| TAA | 41BB/CD28* | CD7 | FcεRIβ |
| TAA | 41BB/CD28* | CD7 | FcεRIγ |
| TAA | 41BB/CD28* | CD7 | DAP10 |
| TAA | 41BB/CD28* | CD7 | DAP12 |
| TAA | 41BB/CD28* | CD7 | CD32 |
| TAA | 41BB/CD28* | CD7 | CD79a |
| TAA | 41BB/CD28* | CD7 | CD79b |
| TAA | 41BB/CD28* | BTNL3 | CD8 |
| TAA | 41BB/CD28* | BTNL3 | CD3ζ |
| TAA | 41BB/CD28* | BTNL3 | CD3δ |
| TAA | 41BB/CD28* | BTNL3 | CD3γ |
| TAA | 41BB/CD28* | BTNL3 | CD3ε |
| TAA | 41BB/CD28* | BTNL3 | FcγRI-γ |
| TAA | 41BB/CD28* | BTNL3 | FcγRIII-γ |
| TAA | 41BB/CD28* | BTNL3 | FcεRIβ |
| TAA | 41BB/CD28* | BTNL3 | FcεRIγ |
| TAA | 41BB/CD28* | BTNL3 | DAP10 |
| TAA | 41BB/CD28* | BTNL3 | DAP12 |
| TAA | 41BB/CD28* | BTNL3 | CD32 |
| TAA | 41BB/CD28* | BTNL3 | CD79a |
| TAA | 41BB/CD28* | BTNL3 | CD79b |
| TAA | 41BB/CD28* | NKG2D | CD8 |
| TAA | 41BB/CD28* | NKG2D | CD3ζ |
| TAA | 41BB/CD28* | NKG2D | CD3δ |
| TAA | 41BB/CD28* | NKG2D | CD3γ |
| TAA | 41BB/CD28* | NKG2D | CD3ε |
| TAA | 41BB/CD28* | NKG2D | FcγRI-γ |
| TAA | 41BB/CD28* | NKG2D | FcγRIII-γ |
| TAA | 41BB/CD28* | NKG2D | FcεRIβ |
| TAA | 41BB/CD28* | NKG2D | FcεRIγ |
| TAA | 41BB/CD28* | NKG2D | DAP10 |
| TAA | 41BB/CD28* | NKG2D | DAP12 |
| TAA | 41BB/CD28* | NKG2D | CD32 |
| TAA | 41BB/CD28* | NKG2D | CD79a |
| TAA | 41BB/CD28* | NKG2D | CD79b |
| TAA | CD8 | 41BB/CD28* | CD8 |
| TAA | CD8 | 41BB/CD28* | CD3ζ |
| TAA | CD8 | 41BB/CD28* | CD3δ |
| TAA | CD8 | 41BB/CD28* | CD3γ |
| TAA | CD8 | 41BB/CD28* | CD3ε |
| TAA | CD8 | 41BB/CD28* | FcγRI-γ |
| TAA | CD8 | 41BB/CD28* | FcγRIII-γ |
| TAA | CD8 | 41BB/CD28* | FcεRIβ |
| TAA | CD8 | 41BB/CD28* | FcεRIγ |
| TAA | CD8 | 41BB/CD28* | DAP10 |
| TAA | CD8 | 41BB/CD28* | DAP12 |
| TAA | CD8 | 41BB/CD28* | CD32 |
| TAA | CD8 | 41BB/CD28* | CD79a |
| TAA | CD8 | 41BB/CD28* | CD79b |
| TAA | CD4 | 41BB/CD28* | CD8 |
| TAA | CD4 | 41BB/CD28* | CD3ζ |
| TAA | CD4 | 41BB/CD28* | CD3δ |
| TAA | CD4 | 41BB/CD28* | CD3γ |
| TAA | CD4 | 41BB/CD28* | CD3ε |
| TAA | CD4 | 41BB/CD28* | FcγRI-γ |
| TAA | CD4 | 41BB/CD28* | FcγRIII-γ |
| TAA | CD4 | 41BB/CD28* | FcεRIβ |
| TAA | CD4 | 41BB/CD28* | FcεRIγ |
| TAA | CD4 | 41BB/CD28* | DAP10 |
| TAA | CD4 | 41BB/CD28* | DAP12 |
| TAA | CD4 | 41BB/CD28* | CD32 |
| TAA | CD4 | 41BB/CD28* | CD79a |
| TAA | CD4 | 41BB/CD28* | CD79b |
| TAA | b2c | 41BB/CD28* | CD8 |
| TAA | b2c | 41BB/CD28* | CD3ζ |
| TAA | b2c | 41BB/CD28* | CD3δ |
| TAA | b2c | 41BB/CD28* | CD3γ |
| TAA | b2c | 41BB/CD28* | CD3ε |
| TAA | b2c | 41BB/CD28* | FcγRI-γ |
| TAA | b2c | 41BB/CD28* | FcγRIII-γ |
| TAA | b2c | 41BB/CD28* | FcεRIβ |
| TAA | b2c | 41BB/CD28* | FcεRIγ |
| TAA | b2c | 41BB/CD28* | DAP10 |
| TAA | b2c | 41BB/CD28* | DAP12 |
| TAA | b2c | 41BB/CD28* | CD32 |
| TAA | b2c | 41BB/CD28* | CD79a |
| TAA | b2c | 41BB/CD28* | CD79b |
| TAA | CD137/41BB | 41BB/CD28* | CD8 |
| TAA | CD137/41BB | 41BB/CD28* | CD3ζ |
| TAA | CD137/41BB | 41BB/CD28* | CD3δ |
| TAA | CD137/41BB | 41BB/CD28* | CD3γ |
| TAA | CD137/41BB | 41BB/CD28* | CD3ε |
| TAA | CD137/41BB | 41BB/CD28* | FcγRI-γ |
| TAA | CD137/41BB | 41BB/CD28* | FcγRIII-γ |
| TAA | CD137/41BB | 41BB/CD28* | FcεRIβ |

TABLE 2-continued

Third Generation CARs

| ScFv | Co-stimulatory Signal | Co-stimulatory Signal | Signal Domain |
|------|----------------------|----------------------|---------------|
| TAA | CD137/41BB | 41BB/CD28* | FcεRIγ |
| TAA | CD137/41BB | 41BB/CD28* | DAP10 |
| TAA | CD137/41BB | 41BB/CD28* | DAP12 |
| TAA | CD137/41BB | 41BB/CD28* | CD32 |
| TAA | CD137/41BB | 41BB/CD28* | CD79a |
| TAA | CD137/41BB | 41BB/CD28* | CD79b |
| TAA | ICOS | 41BB/CD28* | CD8 |
| TAA | ICOS | 41BB/CD28* | CD3ζ |
| TAA | ICOS | 41BB/CD28* | CD3δ |
| TAA | ICOS | 41BB/CD28* | CD3γ |
| TAA | ICOS | 41BB/CD28* | CD3ε |
| TAA | ICOS | 41BB/CD28* | FcγRI-γ |
| TAA | ICOS | 41BB/CD28* | FcγRIII-γ |
| TAA | ICOS | 41BB/CD28* | FcεRIβ |
| TAA | ICOS | 41BB/CD28* | FcεRIγ |
| TAA | ICOS | 41BB/CD28* | DAP10 |
| TAA | ICOS | 41BB/CD28* | DAP12 |
| TAA | ICOS | 41BB/CD28* | CD32 |
| TAA | ICOS | 41BB/CD28* | CD79a |
| TAA | ICOS | 41BB/CD28* | CD79b |
| TAA | CD27 | 41BB/CD28* | CD8 |
| TAA | CD27 | 41BB/CD28* | CD3ζ |
| TAA | CD27 | 41BB/CD28* | CD3δ |
| TAA | CD27 | 41BB/CD28* | CD3γ |
| TAA | CD27 | 41BB/CD28* | CD3ε |
| TAA | CD27 | 41BB/CD28* | FcγRI-γ |
| TAA | CD27 | 41BB/CD28* | FcγRIII-γ |
| TAA | CD27 | 41BB/CD28* | FcεRIβ |
| TAA | CD27 | 41BB/CD28* | FcεRIγ |
| TAA | CD27 | 41BB/CD28* | DAP10 |
| TAA | CD27 | 41BB/CD28* | DAP12 |
| TAA | CD27 | 41BB/CD28* | CD32 |
| TAA | CD27 | 41BB/CD28* | CD79a |
| TAA | CD27 | 41BB/CD28* | CD79b |
| TAA | CD28δ | 41BB/CD28* | CD8 |
| TAA | CD28δ | 41BB/CD28* | CD3ζ |
| TAA | CD28δ | 41BB/CD28* | CD3δ |
| TAA | CD28δ | 41BB/CD28* | CD3γ |
| TAA | CD28δ | 41BB/CD28* | CD3ε |
| TAA | CD28δ | 41BB/CD28* | FcγRI-γ |
| TAA | CD28δ | 41BB/CD28* | FcγRIII-γ |
| TAA | CD28δ | 41BB/CD28* | FcεRIβ |
| TAA | CD28δ | 41BB/CD28* | FcεRIγ |
| TAA | CD28δ | 41BB/CD28* | DAP10 |
| TAA | CD28δ | 41BB/CD28* | DAP12 |
| TAA | CD28δ | 41BB/CD28* | CD32 |
| TAA | CD28δ | 41BB/CD28* | CD79a |
| TAA | CD28δ | 41BB/CD28* | CD79b |
| TAA | CD80 | 41BB/CD28* | CD8 |
| TAA | CD80 | 41BB/CD28* | CD3ζ |
| TAA | CD80 | 41BB/CD28* | CD3δ |
| TAA | CD80 | 41BB/CD28* | CD3γ |
| TAA | CD80 | 41BB/CD28* | CD3ε |
| TAA | CD80 | 41BB/CD28* | FcγRI-γ |
| TAA | CD80 | 41BB/CD28* | FcγRIII-γ |
| TAA | CD80 | 41BB/CD28* | FcεRIβ |
| TAA | CD80 | 41BB/CD28* | FcεRIγ |
| TAA | CD80 | 41BB/CD28* | DAP10 |
| TAA | CD80 | 41BB/CD28* | DAP12 |
| TAA | CD80 | 41BB/CD28* | CD32 |
| TAA | CD80 | 41BB/CD28* | CD79a |
| TAA | CD80 | 41BB/CD28* | CD79b |
| TAA | CD86 | 41BB/CD28* | CD8 |
| TAA | CD86 | 41BB/CD28* | CD3ζ |
| TAA | CD86 | 41BB/CD28* | CD3δ |
| TAA | CD86 | 41BB/CD28* | CD3γ |
| TAA | CD86 | 41BB/CD28* | CD3ε |
| TAA | CD86 | 41BB/CD28* | FcγRI-γ |
| TAA | CD86 | 41BB/CD28* | FcγRIII-γ |
| TAA | CD86 | 41BB/CD28* | FcεRIβ |
| TAA | CD86 | 41BB/CD28* | FcεRIγ |
| TAA | CD86 | 41BB/CD28* | DAP10 |
| TAA | CD86 | 41BB/CD28* | DAP12 |
| TAA | CD86 | 41BB/CD28* | CD32 |
| TAA | CD86 | 41BB/CD28* | CD79a |
| TAA | CD86 | 41BB/CD28* | CD79b |
| TAA | OX40 | 41BB/CD28* | CD8 |
| TAA | OX40 | 41BB/CD28* | CD3ζ |
| TAA | OX40 | 41BB/CD28* | CD3δ |
| TAA | OX40 | 41BB/CD28* | CD3γ |
| TAA | OX40 | 41BB/CD28* | CD3ε |
| TAA | OX40 | 41BB/CD28* | FcγRI-γ |
| TAA | OX40 | 41BB/CD28* | FcγRIII-γ |
| TAA | OX40 | 41BB/CD28* | FcεRIβ |
| TAA | OX40 | 41BB/CD28* | FcεRIγ |
| TAA | OX40 | 41BB/CD28* | DAP10 |
| TAA | OX40 | 41BB/CD28* | DAP12 |
| TAA | OX40 | 41BB/CD28* | CD32 |
| TAA | OX40 | 41BB/CD28* | CD79a |
| TAA | OX40 | 41BB/CD28* | CD79b |
| TAA | DAP10 | 41BB/CD28* | CD8 |
| TAA | DAP10 | 41BB/CD28* | CD3ζ |
| TAA | DAP10 | 41BB/CD28* | CD3δ |
| TAA | DAP10 | 41BB/CD28* | CD3γ |
| TAA | DAP10 | 41BB/CD28* | CD3ε |
| TAA | DAP10 | 41BB/CD28* | FcγRI-γ |
| TAA | DAP10 | 41BB/CD28* | FcγRIII-γ |
| TAA | DAP10 | 41BB/CD28* | FcεRIβ |
| TAA | DAP10 | 41BB/CD28* | FcεRIγ |
| TAA | DAP10 | 41BB/CD28* | DAP10 |
| TAA | DAP10 | 41BB/CD28* | DAP12 |
| TAA | DAP10 | 41BB/CD28* | CD32 |
| TAA | DAP10 | 41BB/CD28* | CD79a |
| TAA | DAP10 | 41BB/CD28* | CD79b |
| TAA | DAP12 | 41BB/CD28* | CD8 |
| TAA | DAP12 | 41BB/CD28* | CD3ζ |
| TAA | DAP12 | 41BB/CD28* | CD3δ |
| TAA | DAP12 | 41BB/CD28* | CD3γ |
| TAA | DAP12 | 41BB/CD28* | CD3ε |
| TAA | DAP12 | 41BB/CD28* | FcγRI-γ |
| TAA | DAP12 | 41BB/CD28* | FcγRIII-γ |
| TAA | DAP12 | 41BB/CD28* | FcεRIβ |
| TAA | DAP12 | 41BB/CD28* | FcεRIγ |
| TAA | DAP12 | 41BB/CD28* | DAP10 |
| TAA | DAP12 | 41BB/CD28* | DAP12 |
| TAA | DAP12 | 41BB/CD28* | CD32 |
| TAA | DAP12 | 41BB/CD28* | CD79a |
| TAA | DAP12 | 41BB/CD28* | CD79b |
| TAA | MyD88 | 41BB/CD28* | CD8 |
| TAA | MyD88 | 41BB/CD28* | CD3ζ |
| TAA | MyD88 | 41BB/CD28* | CD3δ |
| TAA | MyD88 | 41BB/CD28* | CD3γ |
| TAA | MyD88 | 41BB/CD28* | CD3ε |
| TAA | MyD88 | 41BB/CD28* | FcγRI-γ |
| TAA | MyD88 | 41BB/CD28* | FcγRIII-γ |
| TAA | MyD88 | 41BB/CD28* | FcεRIβ |
| TAA | MyD88 | 41BB/CD28* | FcεRIγ |
| TAA | MyD88 | 41BB/CD28* | DAP10 |
| TAA | MyD88 | 41BB/CD28* | DAP12 |
| TAA | MyD88 | 41BB/CD28* | CD32 |
| TAA | MyD88 | 41BB/CD28* | CD79a |
| TAA | MyD88 | 41BB/CD28* | CD79b |
| TAA | CD7 | 41BB/CD28* | CD8 |
| TAA | CD7 | 41BB/CD28* | CD3ζ |
| TAA | CD7 | 41BB/CD28* | CD3δ |
| TAA | CD7 | 41BB/CD28* | CD3γ |
| TAA | CD7 | 41BB/CD28* | CD3ε |
| TAA | CD7 | 41BB/CD28* | FcγRI-γ |
| TAA | CD7 | 41BB/CD28* | FcγRIII-γ |
| TAA | CD7 | 41BB/CD28* | FcεRIβ |
| TAA | CD7 | 41BB/CD28* | FcεRIγ |
| TAA | CD7 | 41BB/CD28* | DAP10 |
| TAA | CD7 | 41BB/CD28* | DAP12 |
| TAA | CD7 | 41BB/CD28* | CD32 |
| TAA | CD7 | 41BB/CD28* | CD79a |
| TAA | CD7 | 41BB/CD28* | CD79b |
| TAA | BTNL3 | 41BB/CD28* | CD8 |
| TAA | BTNL3 | 41BB/CD28* | CD3ζ |
| TAA | BTNL3 | 41BB/CD28* | CD3δ |
| TAA | BTNL3 | 41BB/CD28* | CD3γ |

TABLE 2-continued

Third Generation CARs

| ScFv | Co-stimulatory Signal | Co-stimulatory Signal | Signal Domain |
|------|----------------------|----------------------|---------------|
| TAA | BTNL3 | 41BB/CD28* | CD3ε |
| TAA | BTNL3 | 41BB/CD28* | FcγRI-γ |
| TAA | BTNL3 | 41BB/CD28* | FcγRIII-γ |
| TAA | BTNL3 | 41BB/CD28* | FcεRIβ |
| TAA | BTNL3 | 41BB/CD28* | FcεRIγ |
| TAA | BTNL3 | 41BB/CD28* | DAP10 |
| TAA | BTNL3 | 41BB/CD28* | DAP12 |
| TAA | BTNL3 | 41BB/CD28* | CD32 |
| TAA | BTNL3 | 41BB/CD28* | CD79a |
| TAA | BTNL3 | 41BB/CD28* | CD79b |
| TAA | NKG2D | 41BB/CD28* | CD8 |
| TAA | NKG2D | 41BB/CD28* | CD3ζ |
| TAA | NKG2D | 41BB/CD28* | CD3δ |
| TAA | NKG2D | 41BB/CD28* | CD3γ |
| TAA | NKG2D | 41BB/CD28* | CD3ε |
| TAA | NKG2D | 41BB/CD28* | FcγRI-γ |
| TAA | NKG2D | 41BB/CD28* | FcγRIII-γ |
| TAA | NKG2D | 41BB/CD28* | FcεRIβ |
| TAA | NKG2D | 41BB/CD28* | FcεRIγ |
| TAA | NKG2D | 41BB/CD28* | DAP10 |
| TAA | NKG2D | 41BB/CD28* | DAP12 |
| TAA | NKG2D | 41BB/CD28* | CD32 |
| TAA | NKG2D | 41BB/CD28* | CD79a |
| TAA | NKG2D | 41BB/CD28* | CD79b |

41BB/CD28* = mutated 41BB alone or mutated 41BB in combination with mutated CD28 co-stimulatory domain In some embodiments, the anti-TAA binding agent is single chain variable fragment (scFv) antibody. The affinity/specificity of an anti-TAA scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some cases, the anti-TAA binding agent is an affinity maturated scFv. In some cases, the anti-TAA has a dissociation constant ($K_D$) for the TAA that is less than 50 nM, 40 nM, 30 nM, 25 nM, 20 nM, 15 nM, or 10 nM.

In some embodiments, the anti-TAA binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Tumor antigens are proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated.

In some embodiments, the tumor antigen is selected from the group CD19, TAG-72, CD99, CLEC12A, TIM3, CD83, CD123, TIM3, CD33, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pI85erbB2, pI80erbB-3, c-met, nm-23H1, PSA, CA 19-9, CA 72-4, CAM 17.1, NuMa, K-ras, beta-Catenin, CDK4, Mum-1, p 15, p 16, 43-9F, 5T4, 791Tgp72, alphafetoprotein, beta-HCG, BCA225, BTAA, CA 125, CA 15-3CA 27.29BCAA, CA 195, CA 242, CA-50, CAM43, CD68P1, CO-029, FGF-5, G250, Ga733EpCAM, HTgp-175, M344, MA-50, MG7-Ag, MOV18, NB/70K, NY-CO-1, RCAS1, SDCCAG1 6, TA-90\Mac-2 binding protein\cyclophilm C-associated protein, TAAL6, TAG72, TLP, TPS, GPC3, MUC16, LMP1, EBMA-1, BARF-1, CS1, CD319, HER1, B7H6, L1CAM, IL6, and MET. Tumor antigens include, for example, a glioma-associated antigen, carcinoembryonic antigen (CEA), EGFRvIII, IL-IIRa, IL-13Ra, EGFR, FAP, B7H3, Kit, CALX, CS-1, MUC1, BCMA, bcr-abl, HER2, β-human chorionic gonadotropin, alphafetoprotein (AFP), ALK, CD19, cyclin BI, lectin-reactive AFP, Fos-related antigen 1, ADRB3, thyroglobulin, EphA2, RAGE-1, RUI, RU2, SSX2, AKAP-4, LCK, OY-TESI, PAX5, SART3, CLL-1, fucosyl GM1, GloboH, MN-CA IX, EPCAM, EVT6-AML, TGS5, human telomerase reverse transcriptase, plysialic acid, PLAC1, RUI, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LAGE-Ia, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-beta, survivin and telomerase, legumain, HPV E6, E7, sperm protein 17, SSEA-4, tyrosinase, TARP, WT1, prostate-carcinoma tumor antigen-1 (PCTA-1), ML-IAP, MAGE, MAGE-A1, MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, CD33, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRC5D, GPR20, CXORF61, folate receptor (FRa), folate receptor beta, ROR1, FIt3, TAG72, TN Ag, Tie 2, TEM1, TEM7R, CLDN6, TSHR, UPK2, mesothelin, and any combination thereof.

Nucleic Acids and Vectors

Also disclosed are polynucleotides and polynucleotide vectors encoding the disclosed CARs that allow expression of the CARs in the disclosed immune effector cells.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs (also referred to herein as "CAR-T cells." These cells are preferably obtained from the subject to be treated (i.e. are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as FICOLL™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells (Tc cells, or CTLs) destroy virally infected cells and tumor cells, and are also implicated in transplant rejection. These cells are also known as CD8+ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either CD4+ or CD8+. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of CD4+ $T_{reg}$ cells have been described—naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic CD8+ T lymphocytes. In some embodiments, the T cells comprise γδ T cells, which possess a distinct T-cell receptor (TCR) having one γ chain and one δ chain instead of a and β chains.

Natural-killer (NK) cells are CD56+CD3− large granular lymphocytes that can kill virally infected and transformed cells, and constitute a critical cellular subset of the innate immune system (Godfrey J, et al. Leuk Lymphoma 2012 53:1666-1676). Unlike cytotoxic CD8+ T lymphocytes, NK cells launch cytotoxicity against tumor cells without the requirement for prior sensitization, and can also eradicate MHC-1-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects. Although NK cells have a well-known role as killers of cancer cells, and NK cell impairment has been extensively documented as crucial for progression of MM (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

Therapeutic Methods

Immune effector cells expressing the disclosed CARs can elicit an anti-tumor immune response against TAA-expressing cancer cells. The anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to TAA.

Adoptive transfer of immune effector cells expressing chimeric antigen receptors is a promising anti-cancer therapeutic. Following the collection of a patient's immune effector cells, the cells may be genetically engineered to express the disclosed CARs, then infused back into the patient.

The disclosed CAR-modified immune effector cells may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The cancer of the disclosed methods can be any TAA-expressing cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed CARs can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed CARs can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHlgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed CARs can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec STI571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with a CARs for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, FIt3 ligand, stem cell factor, ancestim, and TNFα. Suitable chemokines may include Glu-Leu-Arg (ELR)- negative chemokines such as IP-10, MCP-3, MIG, and SDF-Ia from the human CXC and C-C chemokine families. Suitable cytokines include cytokine derivatives, cytokine variants, cytokine fragments, and cytokine fusion proteins.

In some embodiments, a therapeutic agent for use in combination with a CARs for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a CARs for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with an CARs for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed CARs is administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed CARs is administered in combination with surgery.

CAR-T cells may be designed in several ways that enhance tumor cytotoxicity and specificity, evade tumor immunosuppression, avoid host rejection, and prolong their therapeutic half-life. TRUCK (T-cells Redirected for Universal Cytokine Killing) T cells for example, possess a CAR but are also engineered to release cytokines such as IL-12 that promote tumor killing. Because these cells are designed to release a molecular payload upon activation of the CAR once localized to the tumor environment, these CAR-T cells are sometimes also referred to as 'armored CARs'. Several cytokines as cancer therapies are being investigated both pre-clinically and clinically, and may also prove useful when similarly incorporated into a TRUCK form of CAR-T therapy. Among these include IL-2, IL-3. IL-4, IL-5, IL-6, IL-7, IL-10, IL-12, IL-13, IL-15, IL-18, M-CSF, GM-CSF, IFN-α, IFN-γ, TNF-α, TRAIL, FLT3 ligand, Lymphotactin, and TGF-β (Dranoff 2004). "Self-driving" or "homing" CAR-T cells are engineered to express a chemokine receptor in addition to their CAR. As certain chemokines can be upregulated in tumors, incorporation of a chemokine receptor aids in tumor trafficking to and infiltration by the adoptive T-cell, thereby enhancing both specificity and functionality of the CAR-T (Moon 2011). Universal CAR-T cells also possess a CAR, but are engineered such that they do not express endogenous TCR (T-cell receptor) or MHC (major histocompatibility complex) proteins. Removal of these two proteins from the signaling repertoire of the adoptive T-cell therapy prevents graft-versus-host-disease and rejection, respectively. Armored CAR-T cells are additionally so named for their ability to evade tumor immunosuppression and tumor-induced CAR-T hypofunction. These particular CAR-Ts possess a CAR, and may be engineered to not express checkpoint inhibitors. Alternatively, these CAR-Ts can be co-administered with a monoclonal antibody (mAb) that blocks checkpoint signaling. Administration of an anti-PDL1 antibody significantly restored the killing ability of CAR TILs (tumor infiltrating lymphocytes). While PD1-PDL1 and CTLA-4-CD80/CD86 signaling pathways have been investigated, it is possible to target other immune checkpoint signaling molecules in the design of an armored CAR-T including LAG-3, Tim-3, IDO-1, 2B4, and KIR. Other intracellular inhibitors of TILs include phosphatases (SHP1), ubiquitin-ligases (i.e., cbl-b), and kinases (i.e., diacylglycerol kinase). Armored CAR-Ts may also be engineered to express proteins or receptors that protect them against or make them resistant to the effects of tumor-secreted cytokines. For example, CTLs (cytotoxic T lymphocytes) transduced with the double negative form of the TGF-β receptor are resistant to the immunosuppression by lymphoma secreted TGF-β. These transduced cells showed notably increased antitumor activity in vivo when compared to their control counterparts.

Tandem and dual CAR-T cells are unique in that they possess two distinct antigen binding domains. A tandem CAR contains two sequential antigen binding domains facing the extracellular environment connected to the intracellular costimulatory and stimulatory domains. A dual CAR is engineered such that one extracellular antigen binding domain is connected to the intracellular costimulatory domain and a second, distinct extracellular antigen binding domain is connected to the intracellular stimulatory domain. Because the stimulatory and costimulatory domains are split between two separate antigen binding domains, dual CARs are also referred to as "split CARs". In both tandem and dual CAR designs, binding of both antigen binding domains is necessary to allow signaling of the CAR circuit in the T-cell. Because these two CAR designs have binding affinities for different, distinct antigens, they are also referred to as "bi-specific" CARs.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC tag, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule AP1903, leading to caspase 9 dimerization and apoptosis. A marked/tagged CAR-T cell however, is one that possesses a CAR but also is engineered to express a selection marker. Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these extracellular domains is directed against a tumor related antigen and bound to an intracellular costimulatory and stimulatory domain. The second extracellular antigen binding domain however is specific for normal tissue and bound to an intracellular checkpoint domain such as CTLA4, PD1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFβ-R. In the presence of normal tissue, stimulation of this second antigen binding domain will work to inhibit the CAR. It should be noted that due to this dual antigen specificity, iCARs are also a form of bi-specific CAR-T cells. The safety CAR-T engineering enhances specificity of the CAR-T cell for tumor tissue, and is advantageous in situations where certain normal tissues may express very low levels of a tumor associated antigen that would lead to off target effects with a standard CAR (Morgan 2010). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason these too are also referred to as a "split CAR".

In some embodiments, two or more of these engineered features may be combined to create an enhanced, multifunctional CAR-T. For example, it is possible to create a CAR-T cell with either dual- or conditional-CAR design that also releases cytokines like a TRUCK. In some embodiments, a dual-conditional CAR-T cell could be made such that it expresses two CARs with two separate antigen binding domains against two distinct cancer antigens, each bound to their respective costimulatory domains. The costimulatory domain would only become functional with the stimulatory domain after the activating molecule is administered. For this CAR-T cell to be effective the cancer must express both cancer antigens and the activating molecule must be administered to the patient; this design thereby incorporating features of both dual and conditional CAR-T cells.

Typically, CAR-T cells are created using α-β T cells, however γ-δ T cells may also be used. In some embodiments, the described CAR constructs, domains, and engineered features used to generate CAR-T cells could similarly be employed in the generation of other types of CAR-expressing immune cells including NK (natural killer) cells, B cells, mast cells, myeloid-derived phagocytes, and NKT cells. Alternatively, a CAR-expressing cell may be created to have properties of both T-cell and NK cells. In an additional embodiment, the transduced with CARs may be autologous or allogeneic.

Several different methods for CAR expression may be used including retroviral transduction (including γ-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

Definitions

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "protein domain" refers to a portion of a protein, portions of a protein, or an entire protein showing structural integrity; this determination may be based on amino acid composition of a portion of a protein, portions of a protein, or the entire protein.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $107$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

A number of embodiments of the invention have been described. Nevertheless, it will be understood that various modifications may be made without departing from the spirit and scope of the invention. Accordingly, other embodiments are within the scope of the following claims.

EXAMPLES

Example 1: 4-1BB Enhancement of CAR T Function Requires NF-κB and TRAFs

Methods

Mice

C57BL/6, Thy1.1(B6.PL-Thy1a/CyJ), and Rag1−/− (B6.129S7-Rag1tm1 Mom/J) mice were purchased from the Jackson Laboratory (Bar Harbor, Me.) and NF-κB-RE-luc (BALB/c-Tg(Rela-luc)31Xen) transgenic mice were purchased from Taconic (Hudson, N.Y.). Traf1−/− mice were gifts from Dr. Tania Watts of University of Toronto and were maintained and bred in the animal facility of Moffitt. NSG mice (NOD.Cg-Prkdcscid Il2rgtm1Wjl/SzJ) were purchased from Jackson Laboratory and bred in the animal facility of Moffitt. Female and/or male mice at 8-12 weeks of age were used for the study. For survival studies, mice were injected i.v. with Ep-ALL ($1 \times 10^6$ cells/mouse, day 0), followed by i.p. cyclophosphamide (250-300 mg/kg, day 6-7) and mCD19-targeted CAR T cells (0.15-5×$10^6$ CAR T cells/mouse, day 7-10). Mice were monitored for illness and sacrificed when there was evidence of leukemia progression, such as decreased activity, hunched posture, and ruffled coat. At certain time points blood and/or bone marrow were collected for analyses. For Rag1−/− mice studies, mice were i.v. injected with $1 \times 10^6$ mCD19-targeted CAR T cells. Blood and BM were collected for flow cytometry.

Cells

The Ep-ALL cell line has been described (Davila M L, et al. PLoS One. 2013 8(4):e61338). The cells were cultured with irradiated (30 Gy) NIH/3T3 fibroblasts as feeders. The culture medium consists of equal volume of 1) IMDM supplemented with 2 mM L-glutamine, 55 µM β-Mercaptoethanol, 100 U/ml Penicillin, 100 µg/ml Streptomycin and 10% FBS and 2) DMEM supplemented with 2 mM L-glutamine, 100 U/ml Penicillin, 100 µg/ml Streptomycin and 10% calf serum. EL4-mCD19 cells were used as target cells and have been described (Davila M L, et al. PLoS One. 2013 8(4):e61338). 3T3-mCD19 and 3T3-hCD19 cells are NIH/3T3 cells retrovirally transduced with mouse or human CD19 and were used as target cells. CHO-hCD33 cells are Chinese hamster ovary (CHO) cells retrovirally transduced with human CD33 and were used as target cells for human CD33 targeted CAR T cells. NIH/3T3 and CHO cells were purchased from ATCC (Manassas, Va.). Mouse T cell complete medium consists of RPM11640 medium, 10% FBS, 1 mM sodium pyruvate, 1×NEAA (Non-essential Amino Acids), 10 mM HEPES, 55 µM β-Mercaptoethanol, 2 mM L-glutamine, 100 U/ml Penicillin and 100 µg/ml Streptomycin. Human PBMCs from healthy donors were purchased from ReachBio (Seattle, Wash.). Human T cell complete medium consists of RPM11640 medium, 10% FBS, 2 mM L-glutamine, 100 U/ml Penicillin and 100 µg/ml Streptomycin. All medium and supplements were from ThermoFisher Scientific (Waltham, Mass.). NF-κB/293/GFP-Luc™ Transcriptional Reporter Cells were purchased from System Biosciences (Palo Alto, Calif.), maintained and used according to the manufacturer's instructions. FFLuc-GFP NALM6 (NALM6-GL) cells have been described (Zhao Z, et al. Cancer Cell. 2015 28(4):415-28).

Genetic Constructs and CAR T Cell Production

Figure 9A:
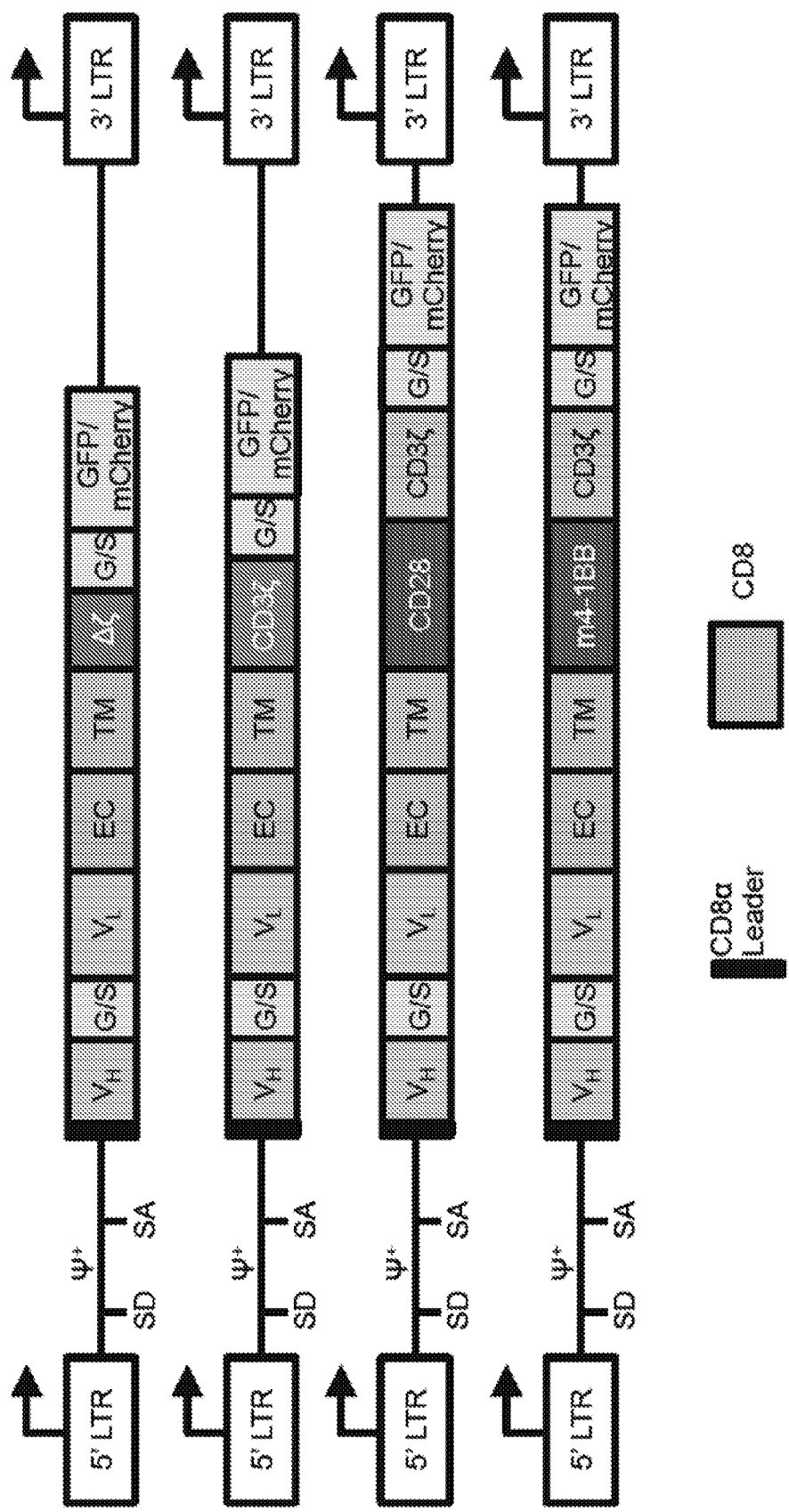
FIG. 9 shows gene expression of fluorescent-protein tagged CAR T cells. (A) Schematic of genetic constructs for mCD19 targeted CARs. Shown are the long terminal repeats (LTR), packaging signal ψ, splice donor (SD), splice acceptor (SA), VH and VL regions of the scFv (single-chain variable fragment), the extracellular hinge (EC), transmembrane (TM), and intracellular regions of the retroviral construct. G/S, (Gly4Ser1)3 linker sequence. (B) Comparison of fluorescence protein and Protein L as a method to evaluate CAR expression. One million T cells transduced with mCherry-tagged CARs were incubated with 1 µg Biotin-Protein L and then fluochrome-conjugated streptavidin. Cells were subjected to flow cytometry. Data are representative of 4 independent experiments. (C) Principal component analysis (PCA) of mCD19-targeted CAR T cells stimulated with antigen. (D) Venn Diagram demonstrating the number of genes differentially expressed (n=205) in m19-musBBz CAR T cells compared to both m19z and m1928z CAR T cells. (E) A heatmap of the 205 differentially expressed genes. The list of 205 genes is included in Supplemental Tables 1-4. For (C)-(E), CAR T cells with the m19z, m1928z, or m19-musBBz CAR tagged to the fluorescent protein GFP were incubated with 3T3-mCD19

The SFG retroviral construct was used for all constructs and m19Δz, m19z, m1928z, and m19-musBBz CAR have been described (Davila M L, et al. PLoS One. 2013 8(4): e61338; Ghosh A, et al. Nat Med. 2017 23(2):242-9). We modified these constructs to replace the mouse 4-1BB endodomain with human 4-1BB endodomain or mutated mouse 4-1BB domain (FIGS. 2A and 9A). A human CD19-targeted CAR was synthesized by Genewiz (South Plainfield, N.J.) to include the FMC63 scFv combined with human counterparts to the mouse 4-1BB endodomain listed in FIG. 9A. TRAF and TRAF DN (dominant negative) constructs include the coding sequences, glycine serine linker, cerulean, and stop codon, which were synthesized and subcloned into the SFG retroviral vector. TRAF DN coding sequences have been described (Duckett C S, et al. Mol Cell Biol. 1997 17(3):1535-42). TRAF1 DN (184-417aa) consists only of the TRAF domain, TRAF2 DN (87-501aa) lacks the ring finger domain, and TRAF3 DN (382-568aa) also lacks the ring finger domain. All SFG constructs were calcium phosphate transfected into H29 cells. Retroviral supernatants of transfected H29 cells were harvested and used to transduce Phoenix E cells for mouse T cell transduction or RD114 cells for human T cell transduction. Retroviral supernatant of Phoenix E or RD114 producer cells were harvested, 0.45 µM filtered and used to transduce mouse or human T cells as described (Davila M L, et al. PLoS One. 2013 8(4):e61338; Li G, et al. Methods Mol Biol. 2017 1514:111-8). For TRAF overexpressed CAR T cells, T cells were co-transduced with retrovirus containing CAR or TRAF at day 1 and day 2. At day 3 or day 4 CAR T cells were collected, beads removed, and subjected to counting and viability evaluation before downstream experimental use. Viability was measured by staining cells with trypan blue and enumerated on an automated cell counter (Bio-Rad, Hercules, Calif.). Transduction efficiency was estimated as percentage of GFP+ or Cherry+ live cells as detected by flow cytometry. In some experiments, CAR expression was evaluated by staining T cells with 1 µg Biotin-Protein L (GenScript, Piscataway, N.J.) followed by fluorochrome-conjugated streptavidin (eBioscience) and flow cytometry as described (Zheng Z, et al. Journal of translational medicine. 2012 10:29). For downstream experiments CAR T cell doses were normalized based on CAR gene-transfer but not sorted to exclude CAR-negative T cells so the total T cell dose varied. For the irradiation study, CAR T cells were irradiated at 10 Gy. Development of the CD33-targeted CARs are described in Supplementary Methods.

Flow Cytometry

These anti-mouse or anti-human antibodies with clones listed were obtained from eBioscience (San Diego, Calif.): anti-mCD16/CD32 (93), anti-mB220 (RA3-6B2), anti-mCD19 (eBio1D3), anti-mCD3 (145-2C11), anti-mCD4 (GK1.5), anti-mCD8 (53-6.7), anti-mThy1.1 (HIS51), anti-mCD44 (1M7), antimCD62L (MEL-14), anti-mTER119 (TER-119), anti-mCD11b (M1/70), anti-mGr1 (RB6-8C5), antimNK1.1 (PK136), anti-mIFNy (XMG1.2), anti-mTNFα (MP6-XT22), and anti-mBcl2 (10C4). These were from Biolegend (San Diego, Calif.): anti-mCD3 (17A2), anti-mCD4 (RM4-5), anti-mCD8 (53-6.7). These were from BD Bioscience (San Jose, Calif.): anti-hCD3 (UCHT1), anti-hCD4 (SK3), anti-hCD8 (RAP-T8). Anti-BCL-XL (54H6) was from Cell Signaling Technology (Danvers, Mass.).

Cells were first washed twice with PBS and stained with fixable viability dye (eBioscience). Surface staining was performed at 4° C. with Fc block (eBioscience) and antibody mix in MACS buffer with 0.5% BSA (Miltenyi Biotec, San Diego, Calif.). For intracellular staining, one million CAR T cells were co-cultured with $1\times10^5$ irradiated 3T3-mCD19 for 4 hr in the presence of protein transport inhibitor (eBioscience). T cells were harvested, fixed and permeabilized with Intracellular Fixation and Permeabilization Buffer Set (eBioscience) followed by antibody staining. The manufacturer's instruction was followed. Peripheral blood samples were stained with antibodies and lysed afterwards using BD FACS lysing solution (Davila M L, et al. PLoS One. 2013 8(4):e61338). For some experiments, Countbright beads (Thermo Fisher Scientific, Waltham, Mass.) were used for cell quantitation. All samples were analyzed with a 5-laser BD LSRII (BD Biosciences) and data were analyzed using FlowJo software (Tree Star, Ashland, Oreg.).

Cytokine Immunoassay

One million mouse CAR T cells were co-cultured with 1×105 3T3-mCD19 cells for 24 hr. Supernatants were harvested and analyzed using a mouse luminex kit (R&D Systems, Minneapolis, Minn.). Data were collected on a Luminex 100 system (Luminex, Austin, Tex.). The manufacturer's instructions were followed. For human CAR T cell study, CAR T cells were co-cultured with 3T3-hCD19 cells at 10:1 for 24 hr. Supernatants were harvested and analyzed using a Simple Plex Assay Kit (R&D systems) on an Ella machine (ProteinSimple, San Jose, Calif.). Manufacturer's instructions were followed.

Cytotoxicity Assay

A 4-hour chromium release assay was performed with EL4-mCD19 as target cells and mouse CD19-targeted CAR T cells as effectors. Our methods have been described (Davila M L, et al. PLoS One. 2013 8(4):e61338). Cytotoxicity assays were also run on an xCELLigence RTCA (real time cell analysis) instrument (ACEA Biosciences, San Diego, Calif.) according to the manufacturer's instructions. Briefly, 3T3-mCD19 or 3T3-hCD19 cells were seeded at 10,000 cells per well in an E-Plate 96. On the next day mouse or human CAR T cells were resuspended in fresh complete medium without IL2 and added onto target cells at different E:T ratios and cell growth was monitored.

Western Blot and Immune Precipitation

CAR T cells were stimulated with 3T3-mCD19 at a 10:1 ratio for 4 hr. Cell lysates were prepared using 240 µl of cell lysis buffer (Cell Signaling Technology, Danvers, Mass.) for 6×106 CAR T cells. 30 µl of reduced and denatured cell lysates were electrophoresed through a 10% Mini-PROTEAN TGX Precast gel (Bio-Rad, Hercules, Calif.), transferred to nitrocellulose blot membranes, blocked, and the membranes were cut based on molecular weight to probe different proteins. The membranes were incubated with primary antibody at 1:1000 overnight at 4 degrees. Blots were washed and incubated with HRP-linked anti-rabbit IgG (Cell Signaling Technology) at 1:10,000 for 1 hr at room temperature. Blots were washed again and incubated with SuperSignal west femto maximum sensitivity substrate (ThermoFisher, Waltham, Mass.). Images were acquired on an Odyssey Fc imaging system (LI-COR Biotechnology, Lincoln, Nebr.). Protein semi-quantitation was done by using ImageJ software. Anti-BCLXL (54H6), anti-BCL2 (D17C4) and anti-β-ACTIN rabbit mAb (13E5) were from Cell Signaling Technology.

For immunoprecipitation (IP) experiments, 30×106 CAR-expressing NF-κB/293/GFP-Luc reporter cells were lysed using RIPA buffer (Cell Biolabs, Inc) supplemented with cOmplete™ Protease Inhibitor Cocktail (Sigma-Aldrich), following the manufacturer's recommendations. Protein extracts were incubated with Protein-L magnetic beads (ThermoScientific™ Pierce™) overnight at 4° C. Immune complexes were recovered using a DynaMag™-2 magnet (LifeTechnologies), and prepared for SDSPAGE.

NF-κB Assays

NF-κB/293/GFP-Luc cells (System Biosciences, Palo Alto, Calif.) were retrovirally transduced with TRAF or TRAF-DN constructs and CD19-targeted CARs. NF-κB signaling was evaluated by measuring GFP expression with flow cytometry. CAR T cells were generated from NF-κB-RE-luc transgenic splenocytes. CAR T cells were co-cultured with irradiated (30 Gy) 3T3-mCD19 cells in 6-well plates for 4 hr. For each group, T cells, normalized to 3×106 mCD19-targeted CAR T cells per well, were incubated with $3 \times 10^5$ 3T3-mCD19 cells per well. After stimulation, cell lysates were prepared using Cell Culture Lysis Reagent (Promega, Madison, Wis.). Luciferase assay was performed using a luciferase assay kit (Promega) according to the manufacturer's instructions. Cell lysates were added at 20 µl per well in a 96-well white plate (Corning, Corning, N.Y.), followed by 100 µl of Luciferase Assay Reagent per well, and bioluminescence was immediately measured on a SpectraMax L microplate luminometer (Molecular Devices, Sunnyvale, Calif.). Each sample was done in triplicate.

Human CD19 Targeted CAR T Cell In Vitro Proliferation

Normalized numbers (1 or $2 \times 10^6$) of human CAR T cells were co-cultured with $2 \times 10^5$ 3T3-hCD19 AAPC per well in non-tissue culture treated 6-well plates in triplicate. Cells were grown in human T cell complete medium supplemented with 60 IU/ml IL2 and split every 2-3 days or whenever the medium turned yellow. Cell viability and total cell numbers in each well were measured daily or every 2-4 days (T isolation as day 0) on a cell counter (Bio-Rad) with trypan blue staining. For flow cytometry analysis of in vitro proliferation, CAR T cells were stained with eFluor670 proliferation dye (eBioscience) and then co-cultured with target cells at 5:1 ratio for 4 days.

Statistics

Means were compared using two-sided unpaired parametric t test. Cytotoxicity curves were compared using Kolmogorov-Smirnov test. Human CAR T cell in vitro proliferation were compared using two-way ANOVA. Survival was compared using log rank test. Statistical analyses were conducted using GraphPad Prism software 7 (Graphpad, La Jolla, Calif.) and the R software package. *P<0.05 is considered significant. P<0.01; *P<0.001; ****P<0.0001; ns, not significant.

Gene Expression

Microarray. For m19z, m1928z and m19-musBBz comparison, three million CAR T cells were incubated with $3 \times 10^5$ 3T3-mCD19 cells overnight. The next day live CAR T cells were sorted into Trizol (Thermo Fisher Scientific, Waltham, Mass.). RNA was isolated according to manufacturer's instructions and run on a MOE 430A 2.0 array Mouse Genechip (Affymetrix, Santa Clara, Calif.) at the Genomics Core Facility. Gene expression analyses and graphic representations were performed with the Partek Genomics Suite Software. RMA normalization was performed and values generated for each probeset for all samples. Differentially expressed genes were detected by ANOVA and probesets of statistical significance were defined by a-fold change >2 and a FDR £0.05.

RNA-SEQ. For m19z, m1928z and m19-humBBz comparison, three million CAR T cells were incubated with $1 \times 10^6$ 3T3-mCD19 cells for 48 hr. Live CD4+ CAR T cells were sorted into Trizol. RNA was isolated according to manufacturer's instructions and evaluated for quality. The Genomic Core performed mRNA enrichment and cDNA library preparation using the Illumina Tru-seq stranded mRNA sample prep kit. Final RNA-seq libraries were reviewed for size and quality on the Agilent TapeStation, followed by quantitative PCR-based quantitation with the Kapa Library Quantification Kit. The libraries sequenced on two NextSeq high-output 2×75 paired-end sequencing runs in order to generate approximately 40 million pairs of reads per sample. Sequence reads were aligned to the human reference genome in a splice-aware fashion using Tophat2 (Trapnell C, et al. Bioinformatics. 2009 25(9):1105-11), allowing for accurate alignments of sequences across introns. Aligned reads were quantitated at the gene level using HTseq (Anders S, et al. Bioinformatics. 2015 31(2): 166-9). Normalization, expression modeling, and difference testing were performed using DESeq (Anders S, et al. Genome Biol. 2010 11(10):R106). Quality control measures included custom scripts and RSeqC (Wang L, et al. Bioinformatics. 2012 28(16):2184-5) to examine read count metrics, alignment fraction, chromosomal alignment counts, expression distribution measures, and principle components analysis and hierarchical clustering.

Differentially expressed genes were detected by ANOVA and probesets of statistical significance were defined by a-fold change >4 and a FDR £0.01. Gene set enrichment analysis was performed (on the gene expression values) to analyze the enrichment of the gene sets using GSEA software. C5 collection version v6.0 from the Molecular Signature Database (MSigDB v6.0 C5), which contains the expert-curated gene ontology (GO) gene sets, were used in the analysis. We used vertebrate homology resource to convert between homologues human and mouse genes. For all comparisons, data was collapsed to gene symbols. 1000 permutations based on gene sets were performed. Gene sets were ranked according to false discovery rate (FDR) q-value. At the default FDR q-value cut-off within GSEA of 0.25, we identified 3 gene sets that are upregulated in m19z and 68 gene sets upregulated in m1928z.

Microarray and RNA-SEQ data have been submitted to GEO (Gene Expression Omnibus) with the accession number GSE112567.

CD33-Targeted CARs

Anti-CD33 antibodies were developed at the Vanderbilt Antibody and Protein Resource using standard methods (Markham N O, et al. Hybridoma (Larchmt). 2012 31(4): 246-54). Briefly, after completing a series of immunizations splenocytes of immunized mice were isolated and fused to a non-Ig secreting myeloma cell line and grown in a semi-solid plate. Antibody-secreting clusters were identified in semi-solid plates and selected for clonal expansion in 96 well plates. During expansion supernatant was collected and assayed for CD33 binding by ELISA as well as flow cytometry. Based on this screening hybridomas were selected for expansion and isolation of RNA, which was used to amplify IgH and IgL rearrangements. Based on the IgH and IgL rearrangements scFv were designed and cloned into the NcoI/NotI sites of our human CD19-targeted CAR in the SFG retroviral cassette. This allowed replacement of the anti-human CD19 scFv with anti-human CD33 scFv. These constructs were then used to produce gammaretroviral supernatant as described in Methods.

In Vivo NALM6 Animal Model of CD19-Targeted CAR T Cells

The NALM6 leukemia mouse model has been described (Zhao Z, et al. Cancer Cell. 2015 28(4):415-28). Briefly, NALM6-GL cells were i.v. injected to NSG mice at $5 \times 10^5$ dose. Four days later, mice were treated with $3 \times 10^5$-$1 \times 10^6$ human CD19 targeted CAR T cells. Human CD19 targeted CAR T cells with excess TRAF2 were made by CAR and mouse TRAF2 co-transduction or transduction with a bicistronic construct combining CAR and human TRAF2. Blood samples were collected weekly for flow cytometry. Leukemia burden was evaluated weekly using bioluminescence imaging on an IVIS system. Survival was monitored. Mice were sacrificed when they develop signs of progressive leukemia.

Results

At stress dose levels CD19 targeted CAR T cells with a mouse 4-1BB endodomain (m19-musBBz) eradicate leukemia less efficaciously than T cells with a CAR containing a CD28 endodomain (m1928z).

Figure 1A:
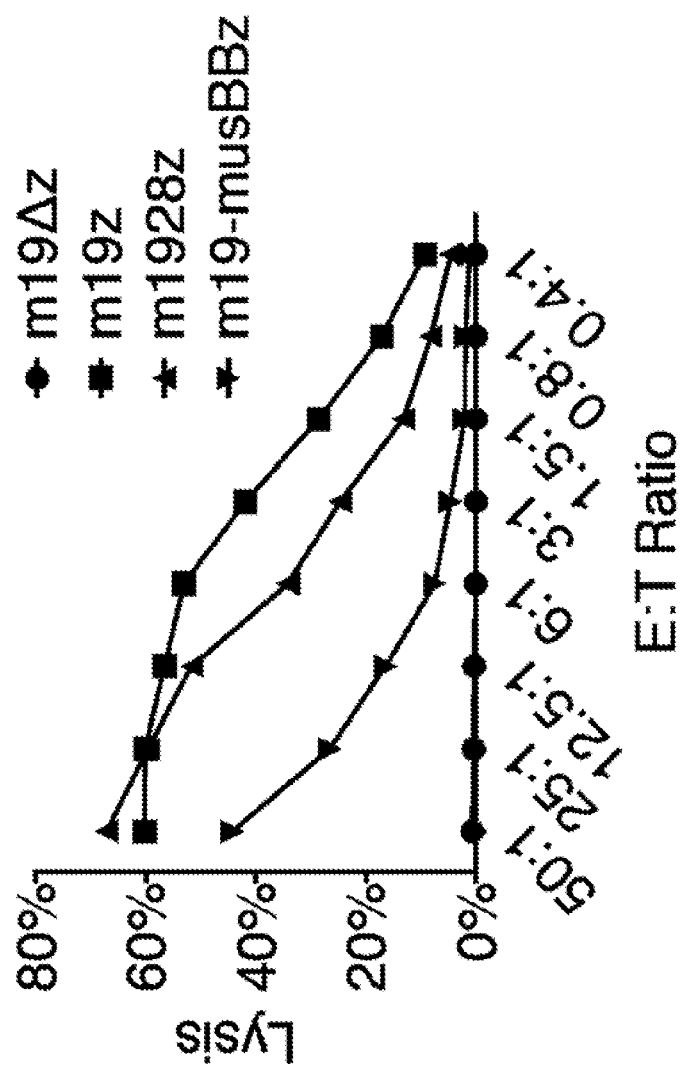
FIG. 1 is a comparison of mouse T cells with mCD19 targeted CARs having different intracellular domains. (A) Cytotoxicity assay. CAR T cells were co-cultured with EL4-mCD19 cells at indicated E:T ratios. Cytotoxicity was evaluated with a Chromium release assay. Data are representative of three independent experiments in triplicate. (B) Cytokine production. CAR T cells were co-cultured with 3T3-mCD19 cells for 24 hr. Supernatant were collected for Luminex assay. Data are representative of two independent experiments in triplicate. (C) Survival, (D) in vivo B cell killing and T cell persistence 3 weeks after CAR T injection at 5×106 dose. Six days after injection with Ep-ALL cells mice were i.p. injected with cyclophosphamide (CTX) followed 1 day later with an i.v. injection of 5×10$^6$ T cells. Survival data are pooled from two independent experiments (n=45 total). Negative control groups are cyclophosphamide alone or with m19Δz CAR T cells (CTX±m19Δz). (E) Survival, (F) in vivo B cell killing and T cell persistence 4 weeks after CAR T injection at 3×105 T cell dose. Seven days after injection with Ep-ALL mice were i.p. injected with CTX followed 1 day later with an i.v. injection of CAR T cells. Survival data are from one experiment (n=39 total). B (B220+CD19+) and donor T (CD3+ Thy1.1+) cells in the blood were quantitated using CountBright counting beads. For (D) and (F), each dot represents one mouse. Survival curve, log rank test; all other data, unpaired t test. *p<0.05; p<0.01; *p<0.001; ns, not significant.
Figure 1B:
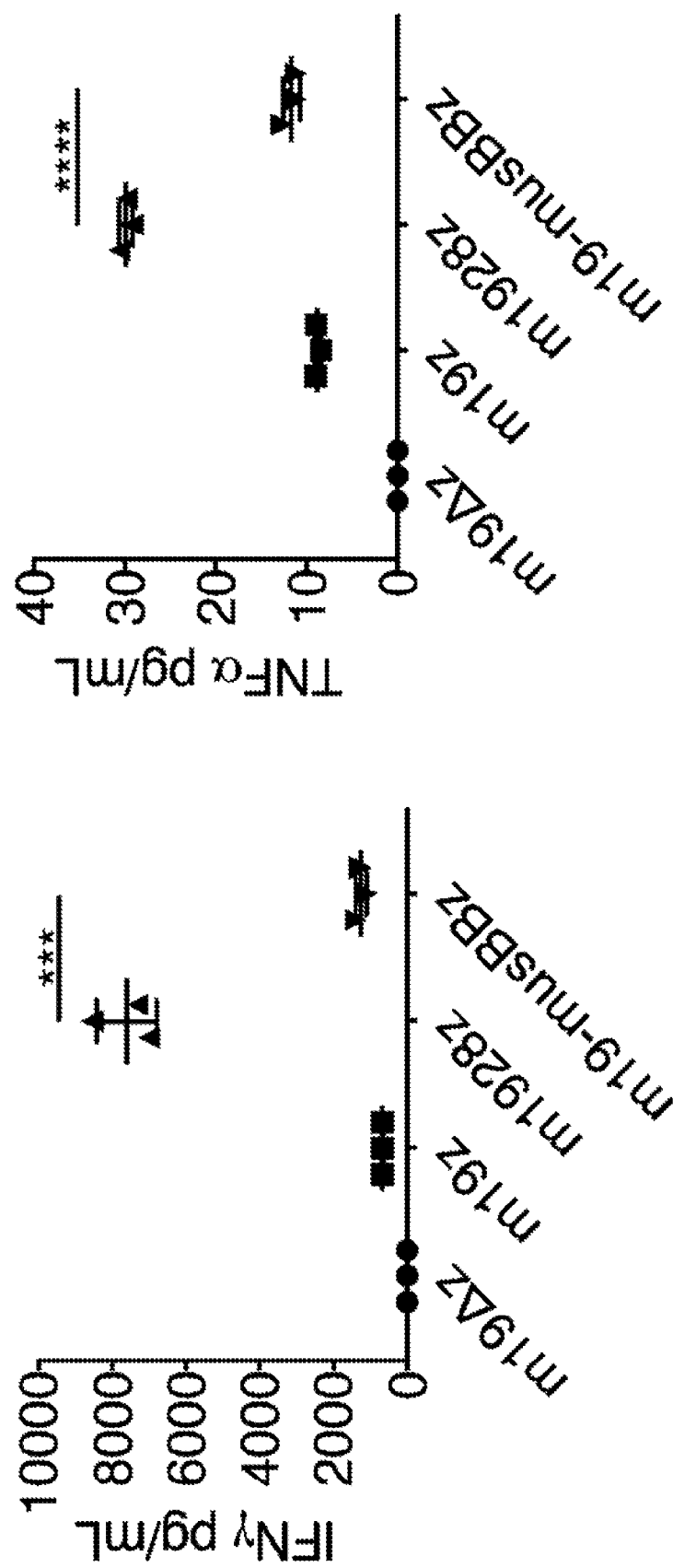

We evaluated four mCD19-targeted CARs, which are all murine-derived with the same extracellular rat-origin anti-mCD19 scFv paired to mouse CD8a hinge and transmembrane domains. They differ only in their intracellular activation and co-stimulatory domains by including no domains (m19Δz), CD3ζ alone (m19z), or CD3z paired with the CD28 (m1928z) or the 4-1BB co-stimulatory domain (m19-musBBz). We performed a comparison of mouse CD19 (mCD19) targeted CAR T cells in an immune competent mouse model (Davila M L, et al. PLoS One. 2013 8(4): e61338) with the rationale that this will allow us to identify biologic differences in adoptively transferred CAR T cells mediated by co-stimulation, which could be further investigated to identify signaling mechanisms driving these differences. We evaluated antigen-specific cytotoxicity of these mouse CAR T cells in a 4-hour chromium-release assay, which demonstrated m1928z or m19z CAR T cells lysed CD19+ target cells at similar levels while m19-musBBz CAR T cells were less efficacious (FIG. 1A). After overnight stimulation with 3T3-mCD19 artificial antigen-presenting cells (AAPC), m1928z CAR T cells released greater IFNg and TNFα than m19-musBBz CAR T cells (FIG. 1B).

Figure 1C:
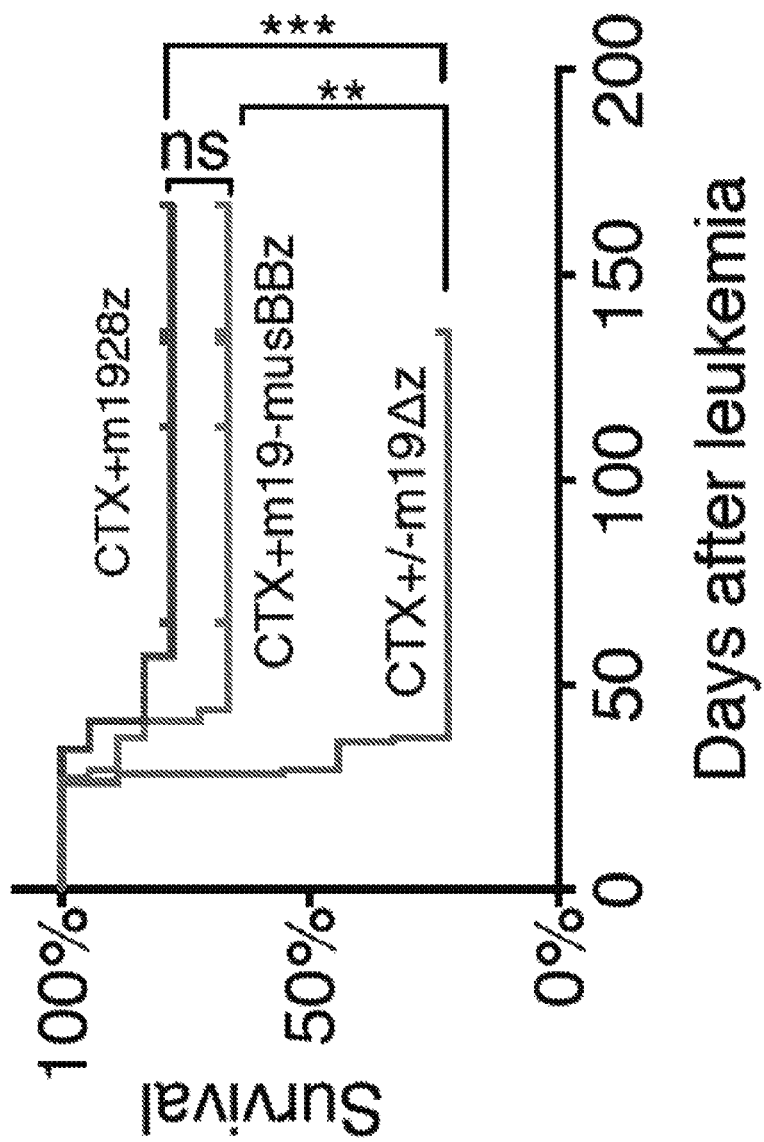
Figure 1D:
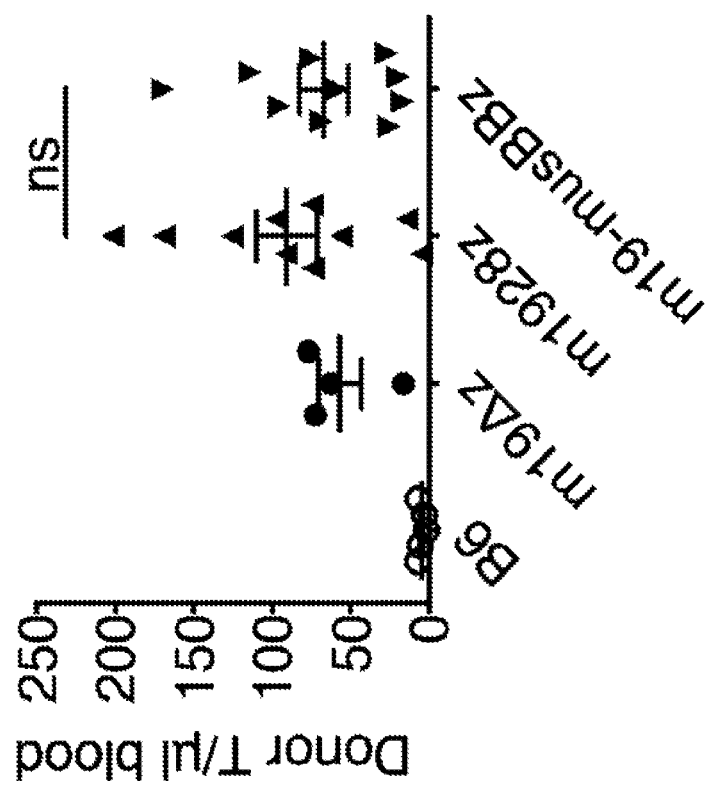
Figure 1D:
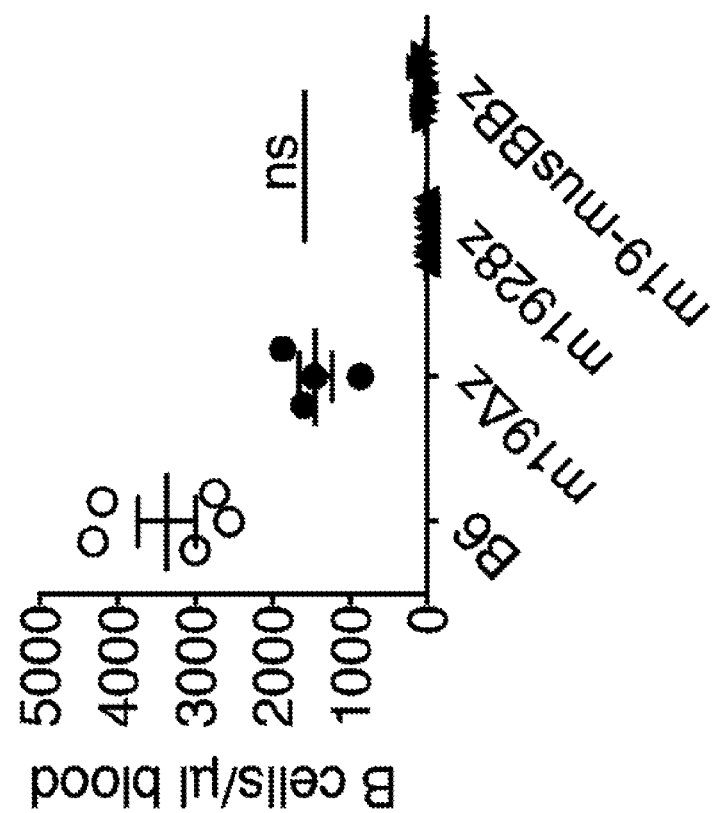
Figure 1E:
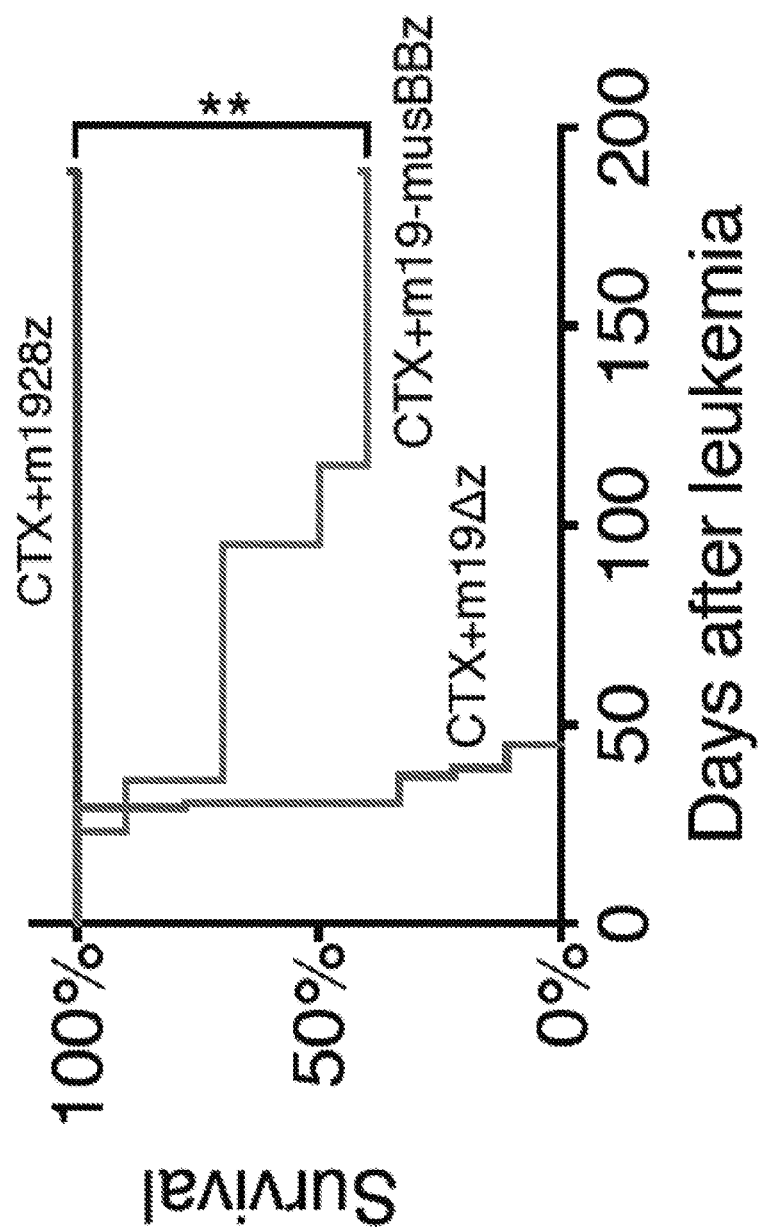
Figure 1F:
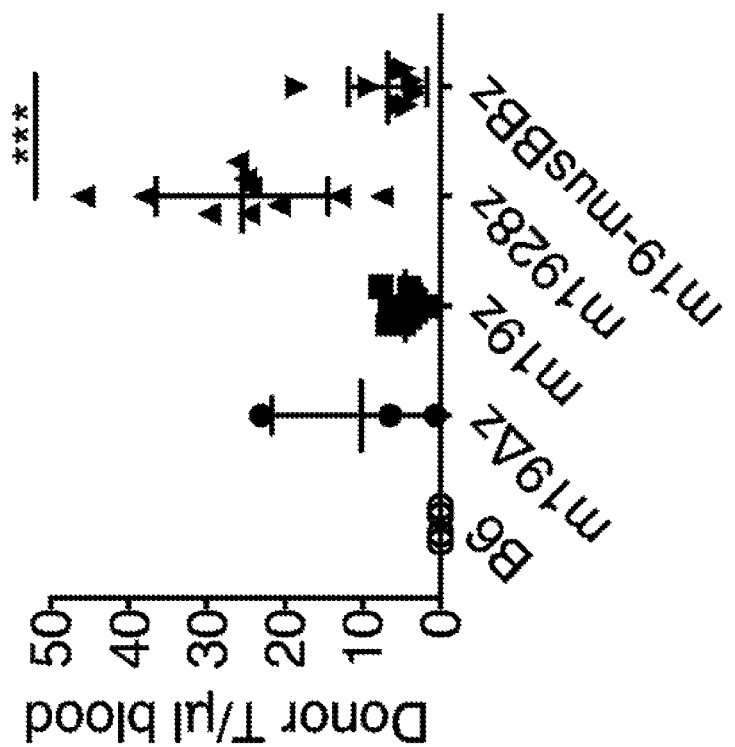
Figure 1F:
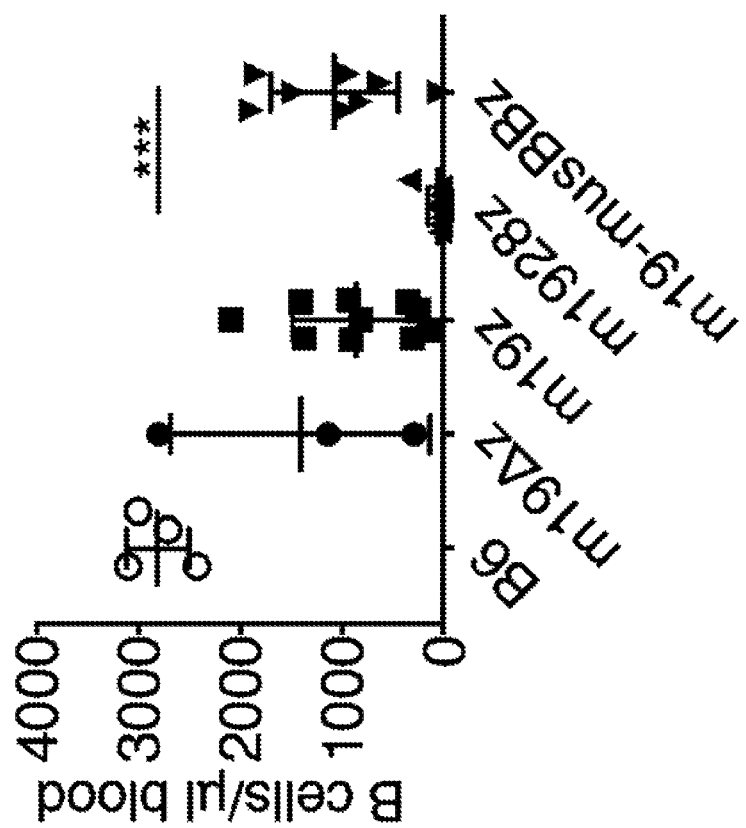
Figure 8A:
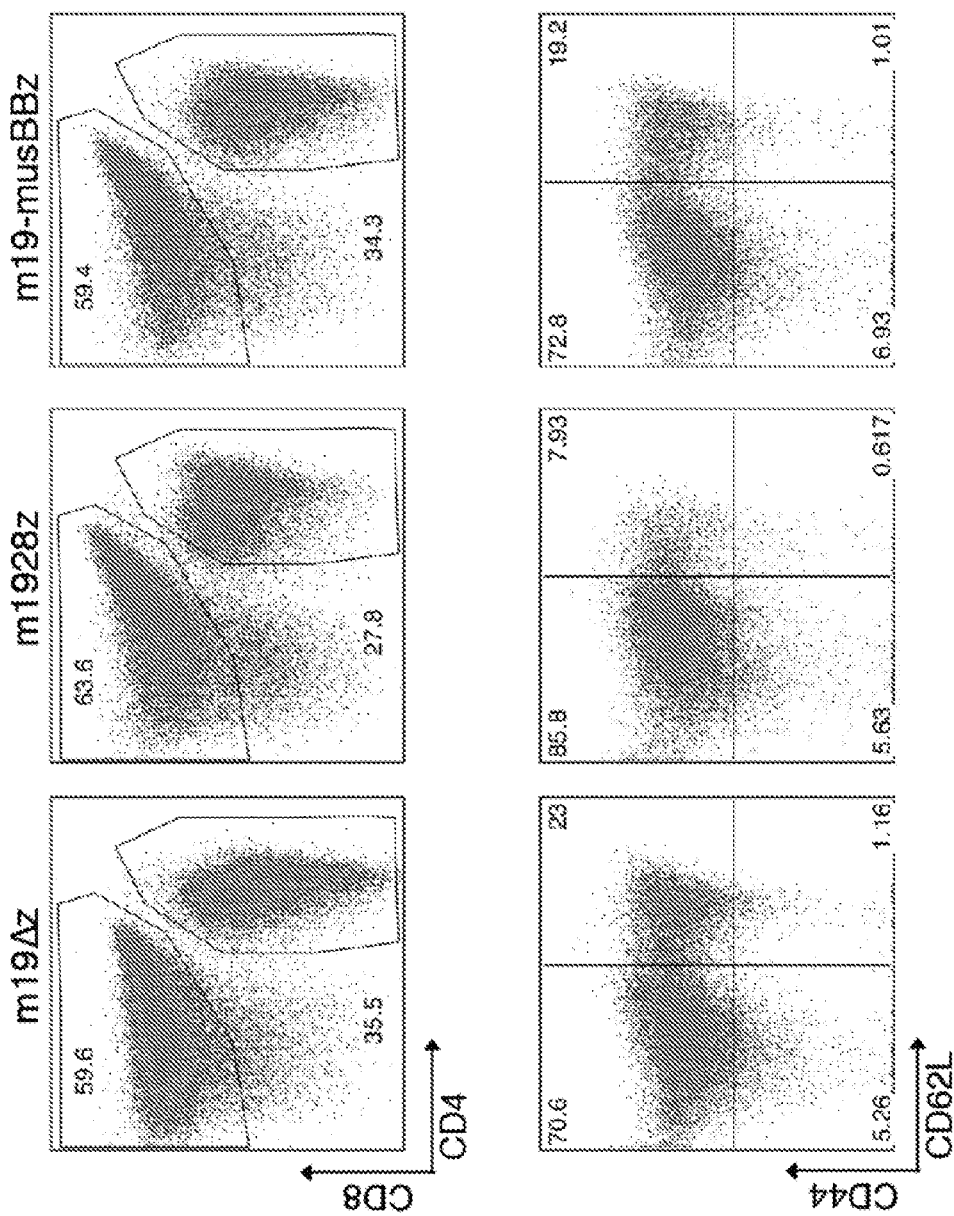
FIG. 8 shows immune phenotype of mCD19 targeted CAR T and dose titration of in vivo efficacy. (A) Immune phenotype of transduced T cells used in 5×10$^6$ dose in vivo study (FIGS. 1C&D). Cells were pre-gated on single live cells. (B) In vivo B cell killing and T cell persistence with T cell dose titration. After Ep-ALL injection, different doses of T cells were given to 300 mg/kg CTX preconditioned mice. B (B220+CD19+) and T (CD3+Thy1.1+) cells in peripheral blood were quantitated 3 weeks after CAR T injection. Each dot indicates one mouse. Data are from one single experiment (n=34 total).
Figure 8B:
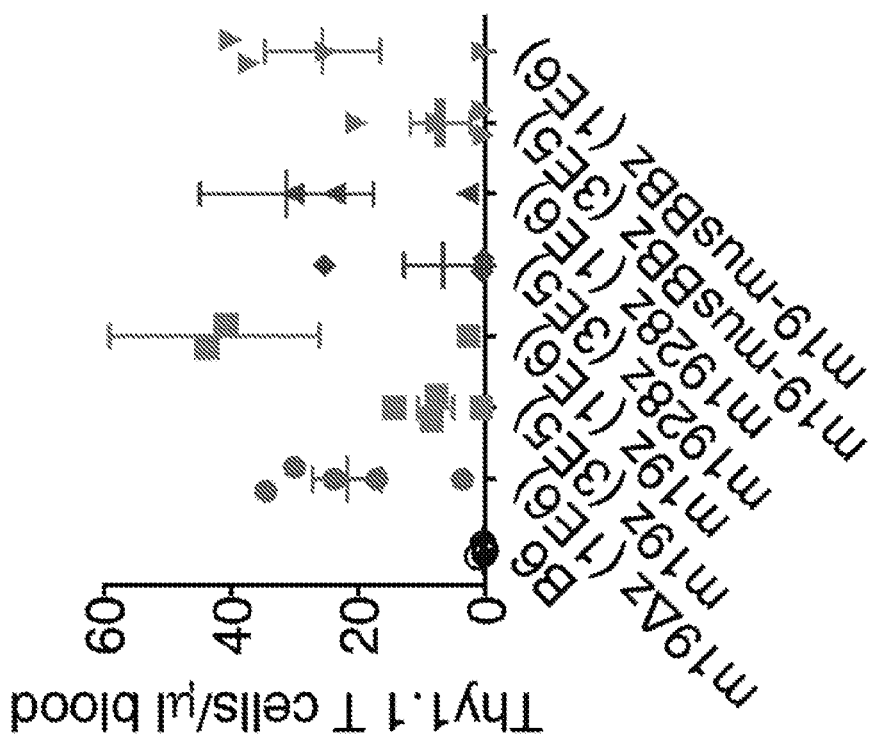
Figure 8B:
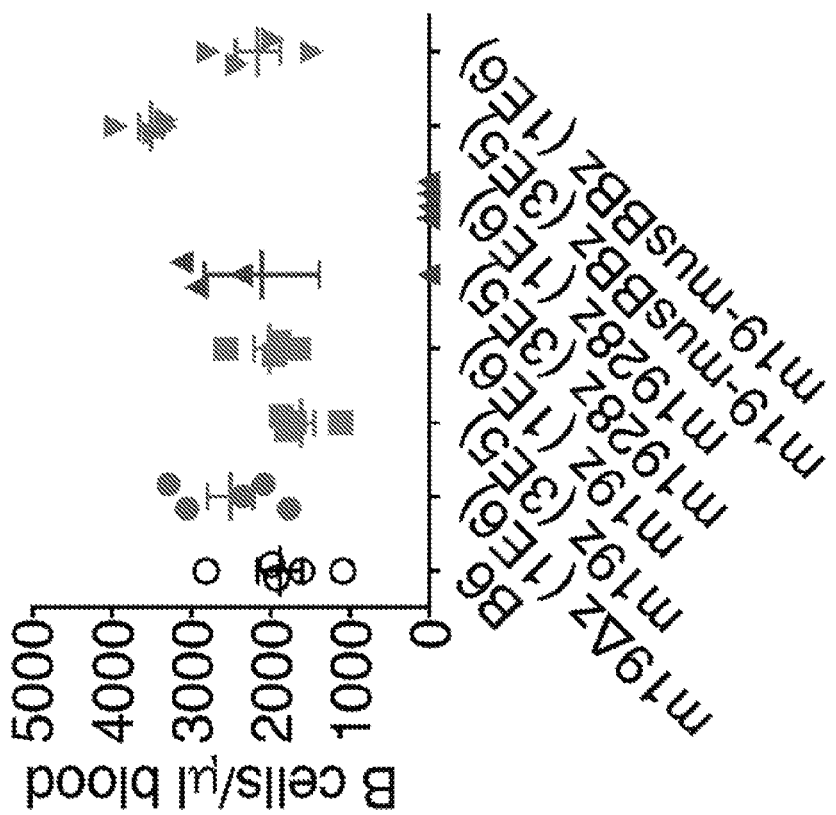

We next compared the in vivo function of mCD19 targeted CAR T cells using our B-ALL mouse model (Davila M L, et al. PLoS One. 2013 8(4):e61338). C57BL/6 mice were intravenously (i.v.) injected with Ep-ALL cells and one week later mice were treated with intraperitoneal (i.p.) cyclophosphamide followed by mCD19-targeted CAR T cells. Despite less efficacious in vitro function, at a dose of 5×106 cells (FIGS. 1C and 8A) m19-musBBz CAR T cells supported similar survival to m1928z CAR T cells. Both m1928z and m19-musBBz CAR T cells maintained B cell aplasia and had comparable persistence in the peripheral blood three weeks after infusion (FIG. 1D). To increase our ability to detect small differences of efficacy between CARs we performed a "stress test" as described (Zhao Z, et al. Cancer Cell. 2015 28(4):415-28) and titrated T cell doses down to levels that had difficulty sustaining B cell aplasia and CAR T cell persistence (FIG. 8B). At the 3×105 dose only 1 out of 4 mice treated with m1928z CAR T cells maintained B cell aplasia 3 weeks after injection (FIG. 8B). Therefore, we chose this, or lower doses, to compare in vivo CAR T cell function. At this lower "stress test" dose m1928z CAR T cells provided superior protection against leukemia compared to m19-musBBz or m19z CAR T cells (FIG. 1E). Also, m1928z CAR T cells had enhanced in vivo B cell aplasia and donor T cell persistence compared to m19-musBBz (FIG. 1F).

Figure 9B:
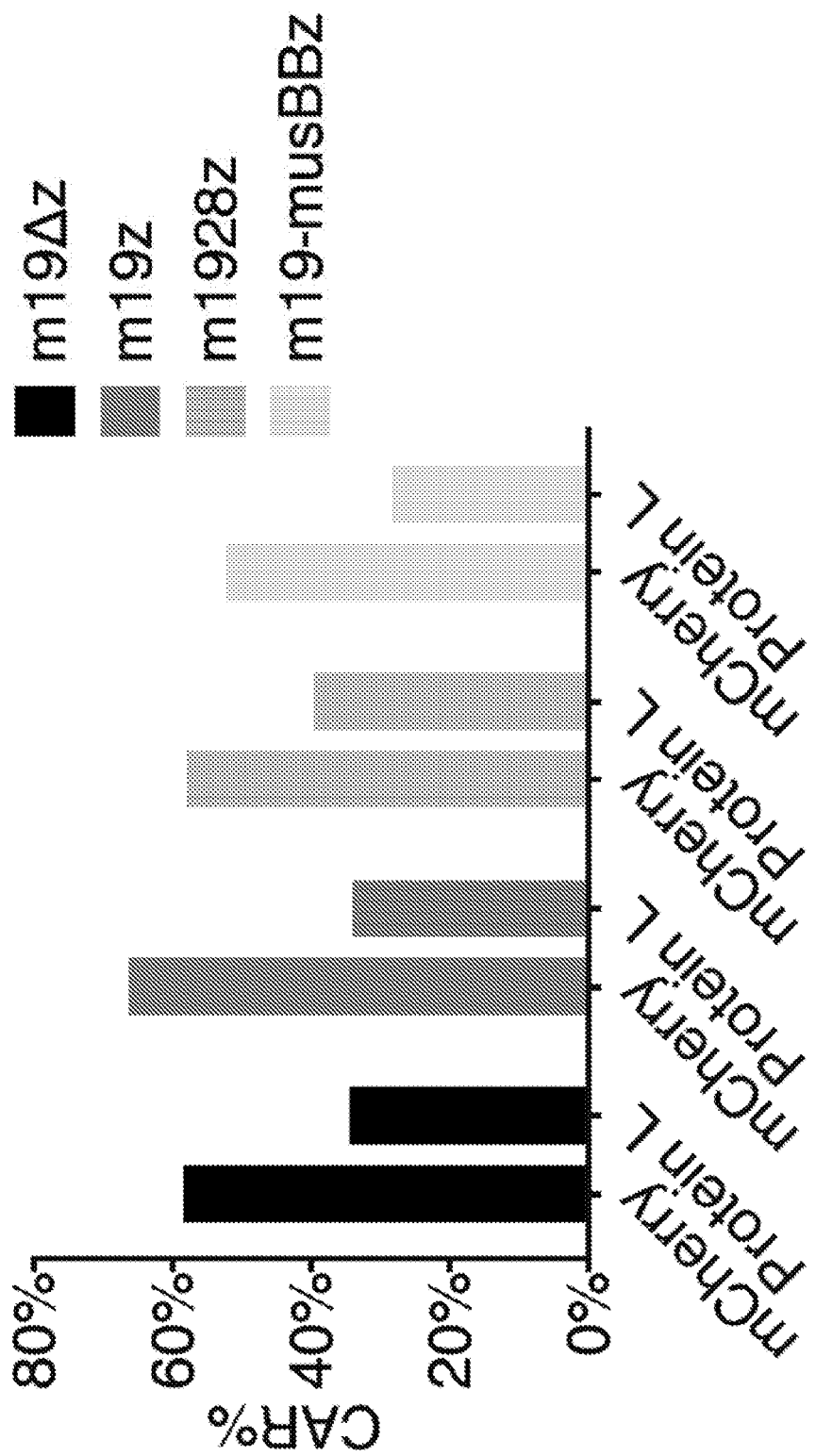
Figure 9C:
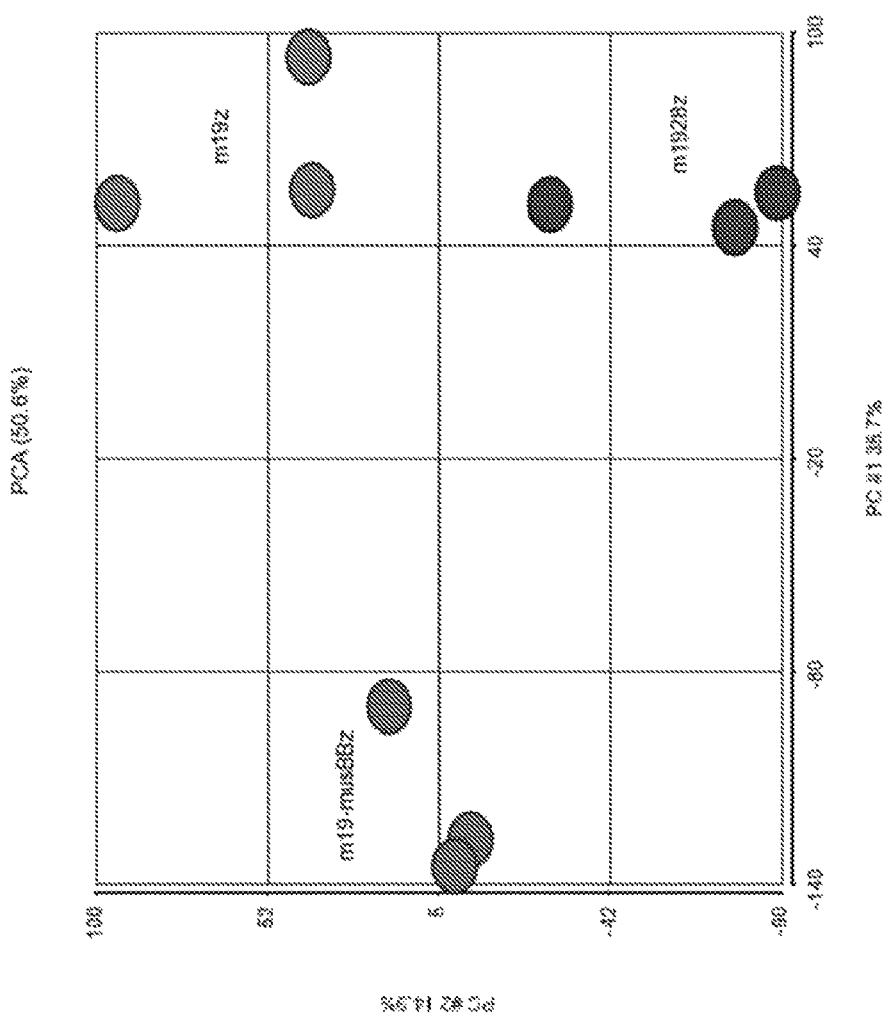
Figure 9D:
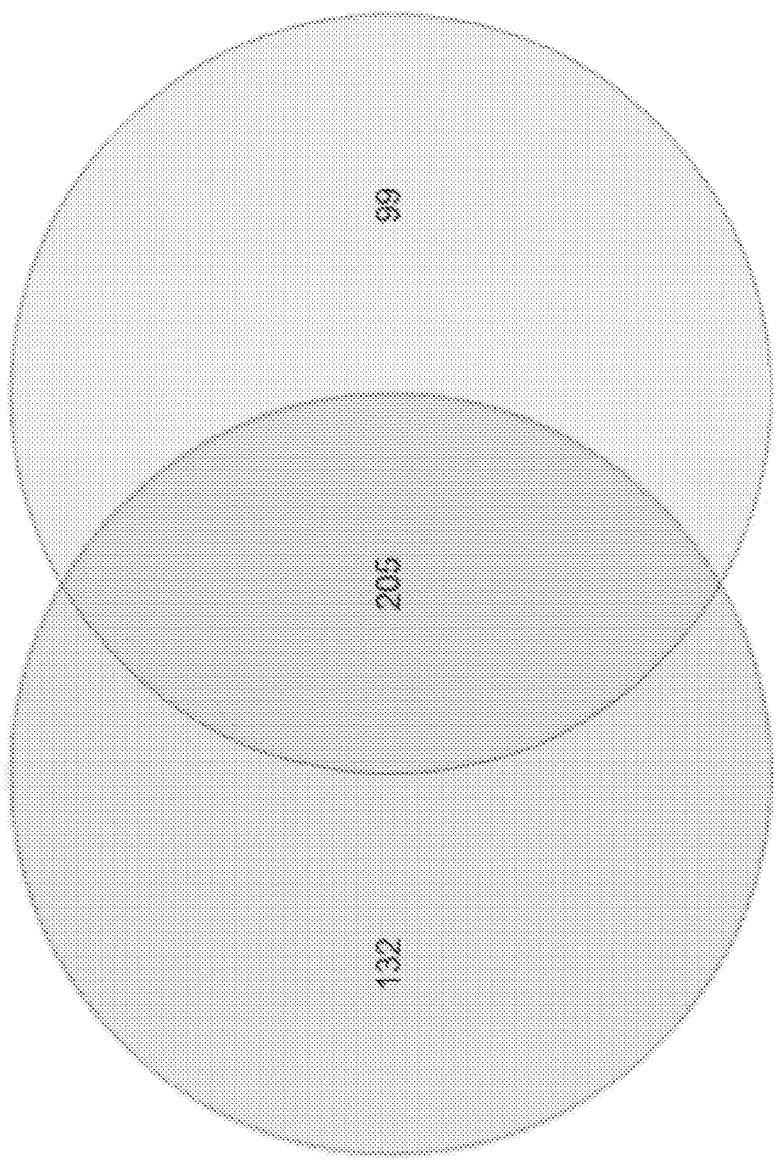
Figure 9E:
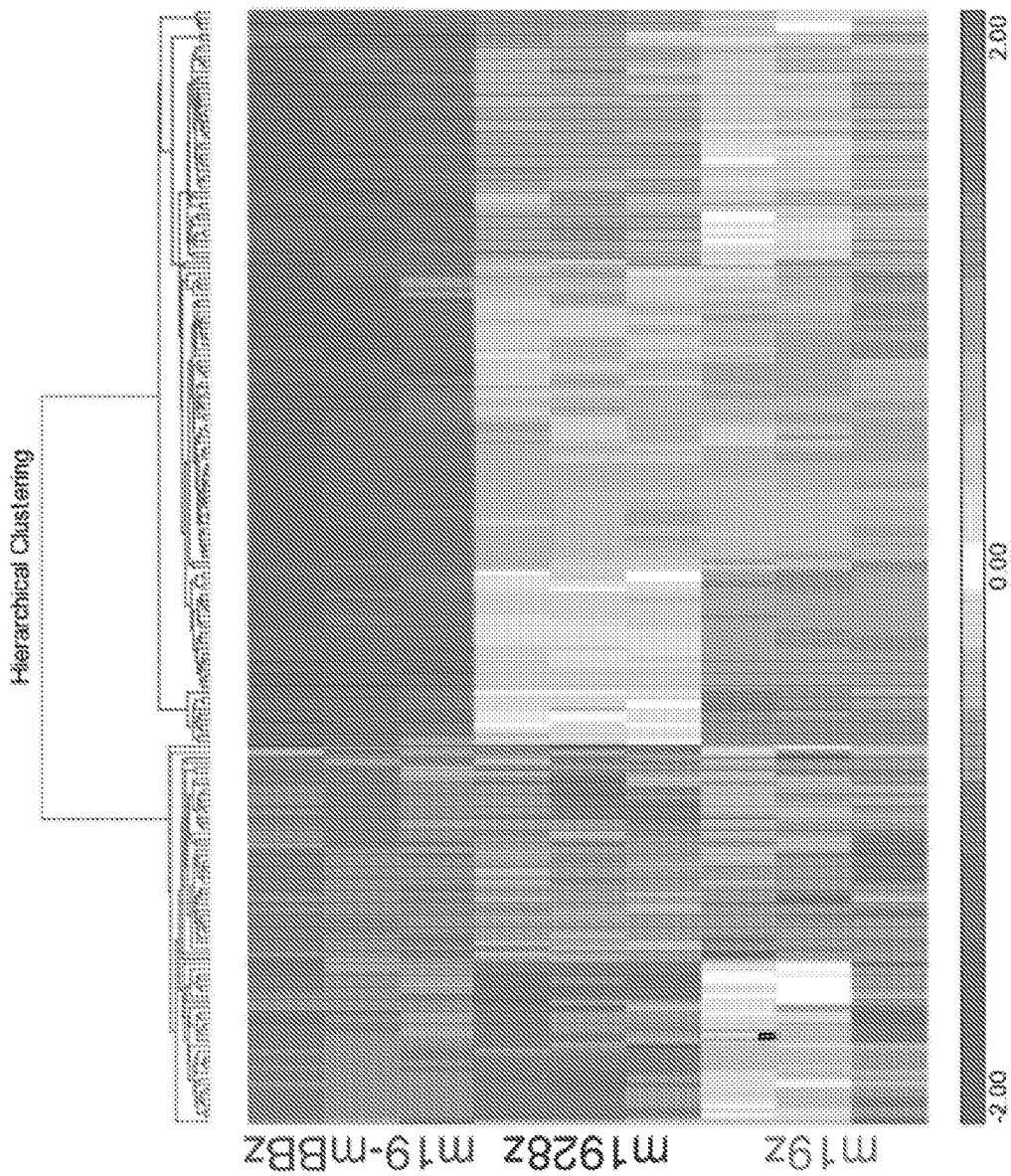
Figure 10A:
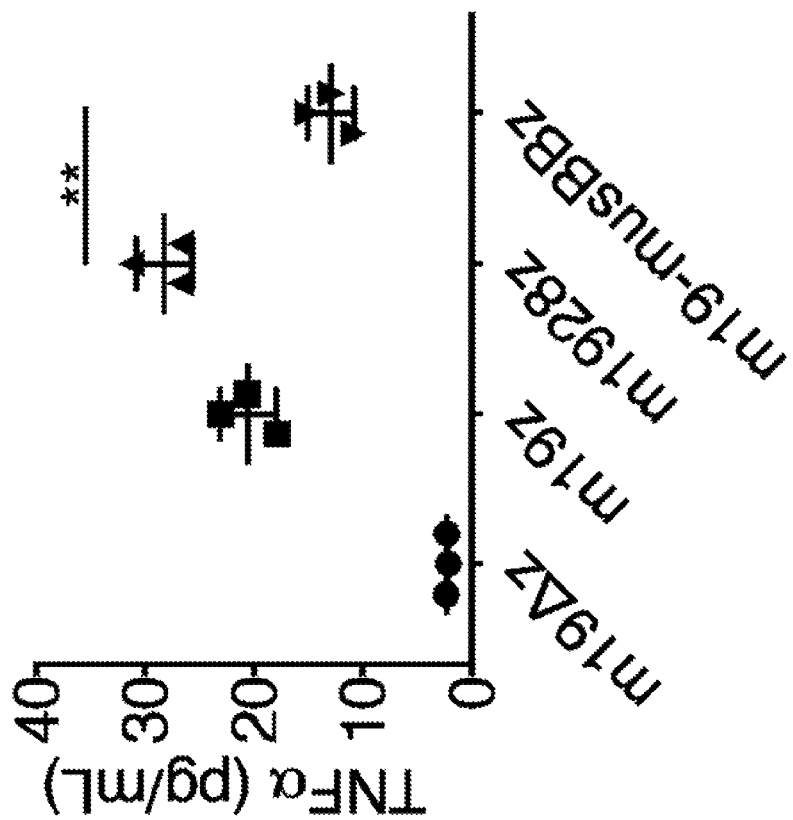
Figure 10A:
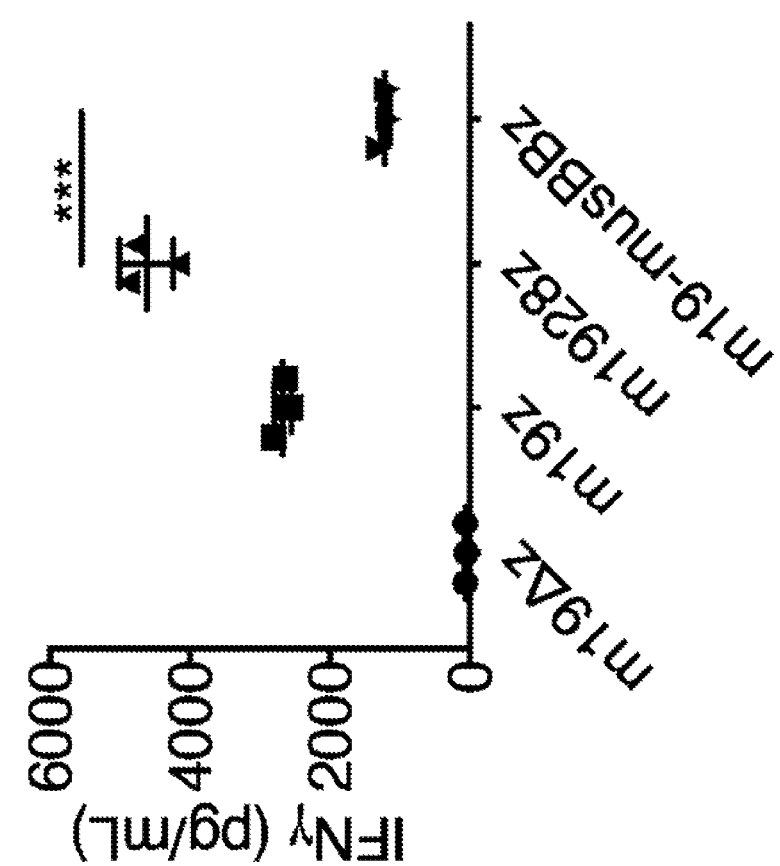
Figure 10B:
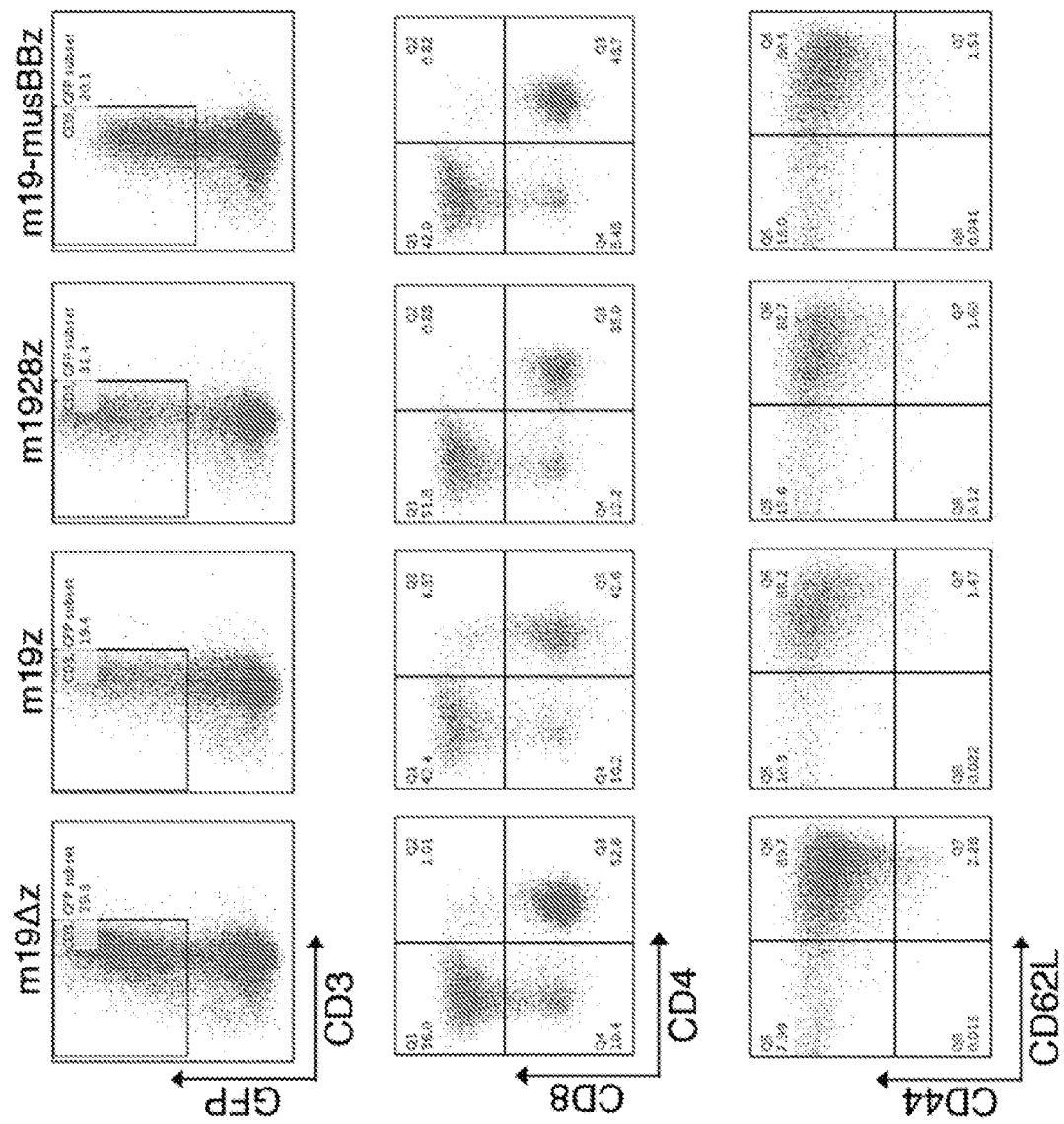
Figure 10C:
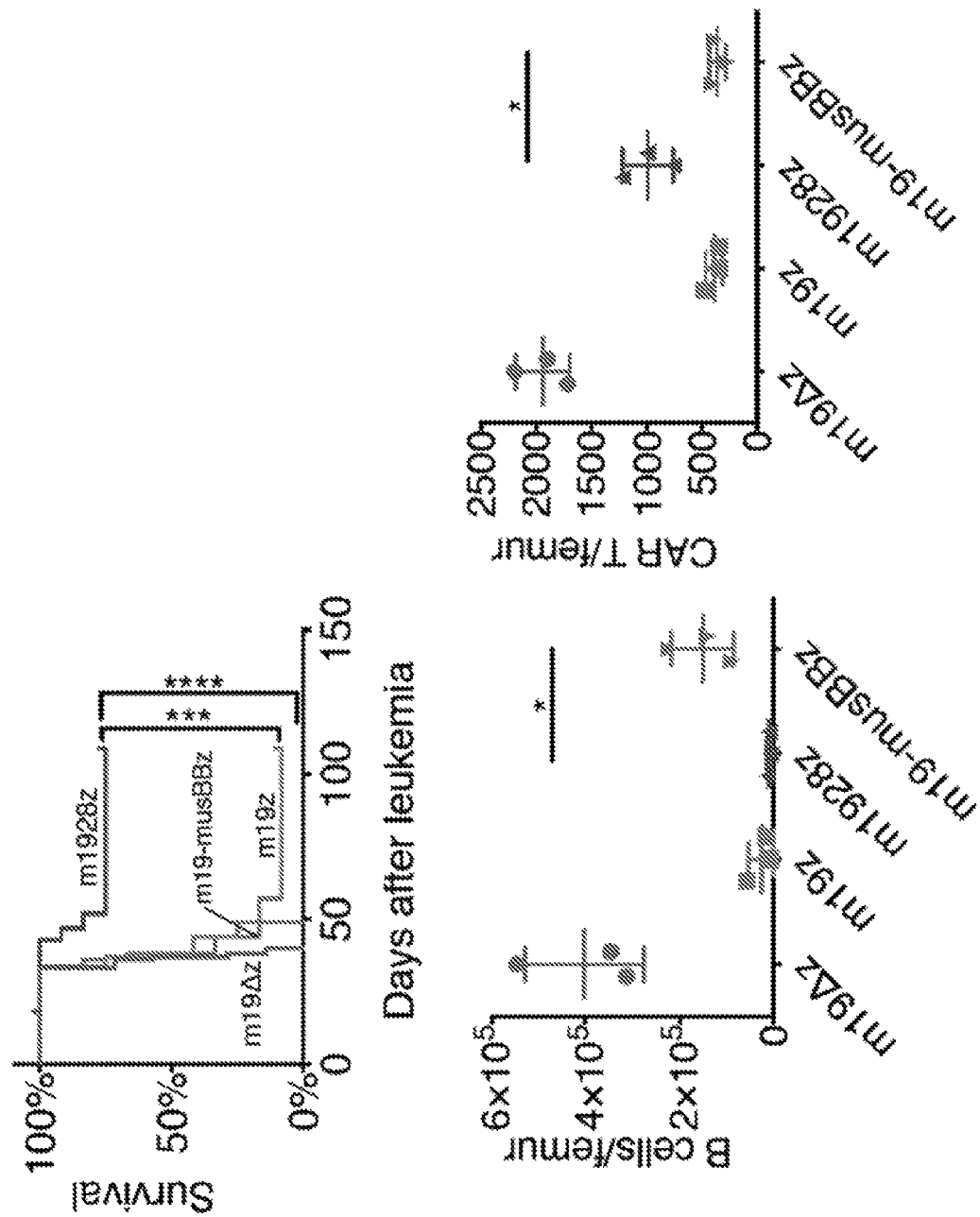
Figure 10D:
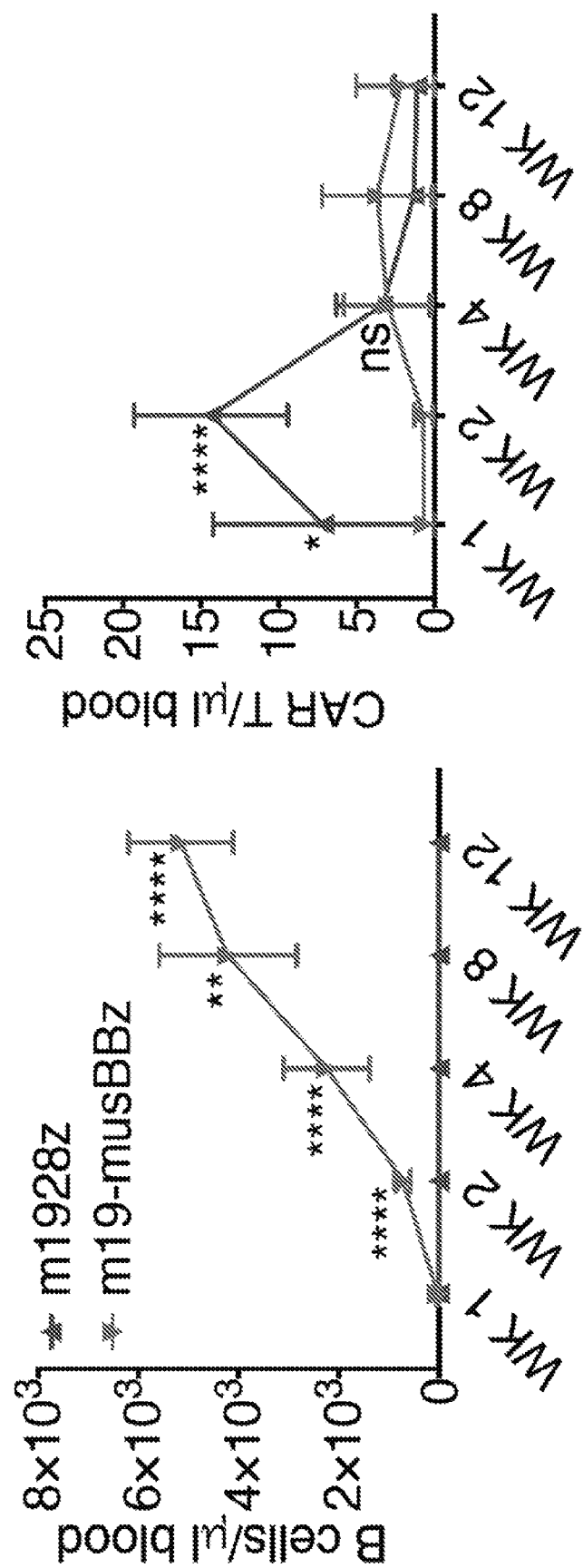

We evaluated the gene expression by microarray of sorted mCD19-targeted CAR T cells after stimulation with 3T3-mCD19 AAPC to determine how gene-expression, and signaling pathways, were impacted by co-stimulation in mouse CAR T cells. Since CAR T cells can downregulate the CAR after ligation (Walker A J, et al. Mol Ther. 2017 25(9):2189-201) we modified the CARs to be directly conjugated to a fluorescent protein using a glycine-serine linker after CD3z in lieu of a reporter not directly associated with the CAR to exclude sorting and analysis of CAR-negative T cells (FIG. 9A). Mouse CD19 targeted CAR T cells with a fluorescent protein tag showed reproducible patterns of CAR expression (FIG. 9B). There is a collection of 205 probesets differentially expressed by m19-musBBz CAR T cells compared to m19z and m1928z CAR T cells (FIGS. 9C-9E). This includes the upregulation of effector genes (Gzmf, Ifng, Prf1), as well as exhaustion genes or transcription factors (Havcr2, CD244, KIrg1, Eomes) in m19z and m1928z CAR T cells (Tables 1-4). In contrast, m19-musBBz CAR T cells upregulate genes critical for NF-κB regulation, T cell quiescence, and memory (Fos, Jun, Tcf7, NF-κBia, Klf2/4). We also observed that cytokine production, immune phenotype, as well as in vivo leukemia eradication, B cell killing, and persistence were not significantly impacted by the fluorescent reporter (FIGS. 10A-10C). We followed the temporal kinetics of CAR T and B cell numbers in the blood to evaluate CAR T cell persistence using the fluorescent-tagged CARs. By 1 week of adoptive transfer there were already differences between CAR T and B cell numbers in the blood (FIG. 10D). This persisted up to week 4 after adoptive transfer with B cell numbers still being different but CAR T cell numbers starting to become similar. Therefore, we chose to focus our analyses of CAR T cell persistence in the blood at the timepoints between 1 and 4 weeks after adoptive transfer.

Inclusion of the Human 4-1BB Endodomain in mCD19 Targeted CAR T Cells Enhances In Vivo Function Clinical results (Davila M L, et al. Sci Transl Med. 2014 6(224):224ra25; Maude S L, et al. N Engl J Med. 2014 371(16):1507-17; Lee D W, et al. Lancet. 2015 385(9967): 517-28; Turtle C J, et al. J Clin Invest. 2016 126(6):2123-38; Park J H, et al. N Engl J Med. 2018 378(5):449-59; Maude S L, et al. N Engl J Med. 2018 378(5):439-48) have demonstrated similar efficacious CR rates for patients with B-ALL when treated with second-generation human CAR T cells that include a CD28 or 4-1BB endodomain. However, using stress test dosing in our mouse model the m19-musBBz appeared modestly less efficacious than m1928z even though there was evidence of 4-1BB co-stimulation (FIGS. 9C-9E). We speculated that sequence differences between human and mouse 4-1BB endodomains, which are 54% identical (FIG. 2A), contribute to the modestly reduced efficacy that is not consistent with clinical observations of 2nd generation CAR T cells. Previous studies have demonstrated that both mouse and human 4-1BB endodomains bind TRAFs, which enhance signaling downstream of TNF-receptor family proteins such as 4-1BB (Jang I K, et al. Biochem Biophys Res Commun. 1998 242(3):613-20; Arch R H, et al. Mol Cell Biol. 1998 18(1):558-65; McPherson A J, et al. J Biol Chem. 2012 287(27):23010-9; Saoulli K, et al. J Exp Med. 1998 187(11):1849-62; Ye H, et al. Mol Cell. 1999 4(3):321-30). However, in vitro assays (Jang I K, et al. Biochem Biophys Res Commun. 1998 242(3):613-20; Arch R H, et al. Mol Cell Biol. 1998 18(1):558-65) suggest that human 4-1BB binds TRAF 1-3 while mouse 4-1BB binds only TRAFs 1-2 leading us to hypothesize that substituting human 4-1BB in mCD19-targeted CAR T cells may enhance TRAF3 binding and CAR T cell function (Vallabhapurapu S, et al. Nat Immunol. 2008 9(12):1364-70). Furthermore, comparison of 4-1BB endodomains with differential TRAF binding abilities may allow us to identify signaling pathways that support enhanced in vivo function by CAR T cells that rely on 4-1BB co-stimulation. Therefore, we created a variant CAR (m19-humBBz) that included the human 4-1BB endodomain paired with the murine scFv, CD8, and CD3z domains included in the other anti-mouse CD19 CARs (FIG. 9A).

We compared the in vitro function of m19-humBBz CAR T cells with other CD19-targeted CAR T cells. After 4 hr stimulation with 3T3-mCD19 AAPC, intracellular flow cytometry demonstrated m1928z CD8+ CAR T cells were 8.4% positive for IFNγ, which is significantly greater than m19-humBBz (1.4%) or m19-musBBz CD8+ CAR T cells (average 0.3%) (FIG. 2B). In addition, m1928z CAR T cells produced the greatest amount of TNFα. There was also enhancement (approximately 2-fold) of TNFα production by T cells modified with the m19-humBBz CAR compared to the m19-musBBz CAR (FIG. 2B). A cytotoxicity assay at a E:T ratio of 10:1 demonstrated that T cells modified with the m19-humBBz CAR did not have enhanced killing compared to m19-musBBz and were less efficacious than m19z and m1928z CARs, which killed all target cells rapidly (FIG. 2C).

Figure 2E:
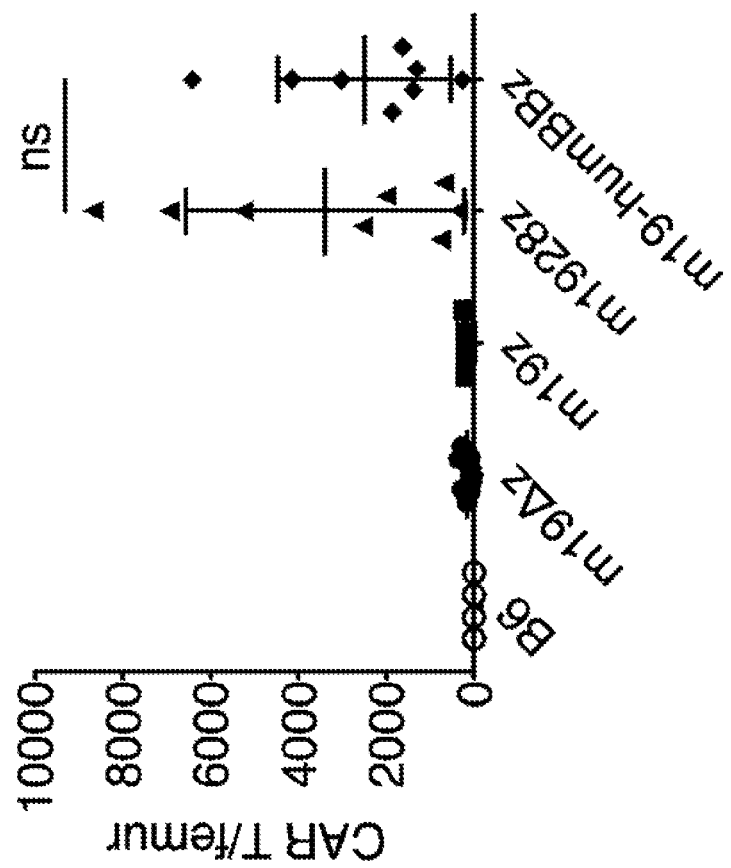
Figure 2E:
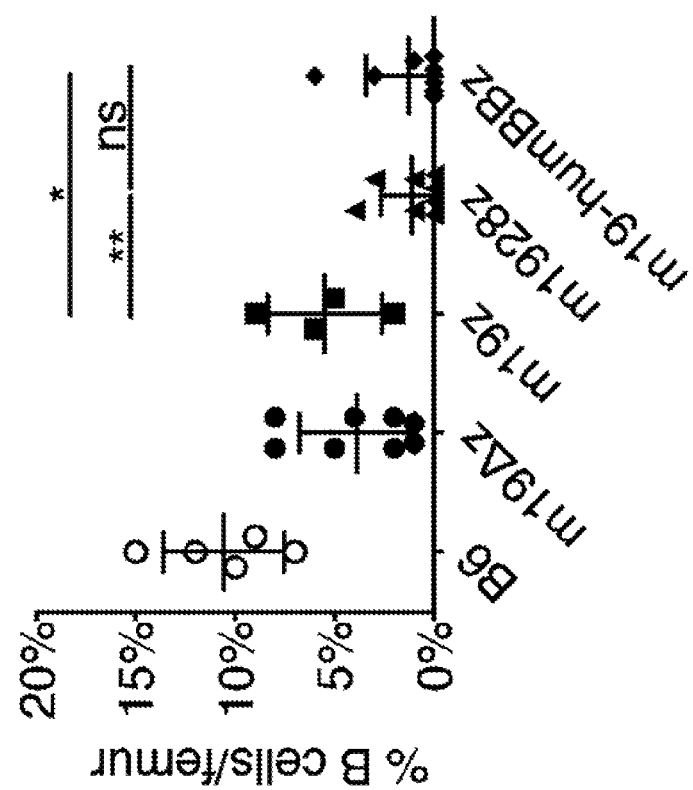

We also compared the in vivo function of m19-humBBz CAR T cells with other mCD19 targeted CAR T cells in our Eμ-ALL model using a stress test cell dose. CAR T cells among all the groups had similarly balanced CD4:CD8 ratios and an immune phenotype composed mostly of central memory (CD44+CD62L+) T cells (FIG. 11). As expected, overall survival (OS) was poor in m19Dz and m19z CAR T cell groups compared to OS imparted by m1928z CAR T cells, which was 57% at Day 150 (FIG. 2D). However, despite their poor in vitro function, under "stress test" conditions m19-humBBz CAR T cells mediated an OS of 70% at Day 150, which was significantly enhanced compared to m19Dz and m19z CAR T cells and similar to m1928z CAR T cells (FIG. 2D). The improved survival mediated by m19-humBBz and m1928z CAR T cells was reflected by B and CAR T cells in the femurs of treated mice. One week after treatment both m19-humBBz and m1928z CAR T cells have similar persistence in the BM and induce B cell aplasia significantly greater than m19z CAR T cells (FIG. 2E).

m19-humBBz CAR T Cells Rely on Persistence to Enhance Function In Vivo

It was recently reported (Zhao Z, et al. Cancer Cell. 2015 28(4):415-28.) that 4-1BB co-stimulation in human CAR T cells supported enhanced persistence in immune deficient mice. Therefore, we hypothesized that equivalent in vivo anti-leukemia killing by m19-humBBz and m1928z CAR T cells, despite differential in vitro function, was due to enhanced m19-humBBz CAR T cell persistence secondary to 4-1BB co-stimulation. Our rationale for evaluating this hypothesis was that identification of a signaling pathway contributing to enhanced persistence would allow potentiation of this attribute. However, we did not identify differences in second-generation CAR T cell persistence in our model (FIG. 2E). Therefore, we evaluated in vivo expansion of mCD19-targeted CAR T cells in Rag1$^{-/-}$ mice, which lack the mCD19 antigen, since the prior report (Zhao Z, et al. Cancer Cell. 2015 28(4):415-28.) demonstrating enhanced persistence was performed in immune deficient mice. Rag1$^{-/-}$ mice were i.v. injected with 1×106 CAR T cells and bone marrow (BM) was isolated 1 week later. The m19-humBBz CAR T cells had the greatest in vivo persistence at 1.5-fold greater than m1928z CAR T cells (FIG. 3A).

To determine if m19-humBBz CAR T cells required persistence for optimal function in vivo we irradiated CAR T cells (10 Gy) prior to injection. C57BL/6 mice were i.p. injected with cyclophosphamide followed by CAR T cells (FIG. 12) one day later. CAR T cell persistence and B cell killing in peripheral blood and BM were evaluated one week after CAR T cell transfer. In both the blood and BM, irradiation significantly reduced persistence of m19-humBBz but not m1928z CAR T cells (FIG. 3B). Correspondingly, in blood there was early B cell recovery in all mice in the irradiated m19-humBBz group compared to 9 out of 10 mice still maintaining B cell aplasia in the non-irradiated m19-humBBz group (FIG. 3C). In contrast, irradiation did not significantly impact B cell killing by m1928z CAR T cells in the blood or BM (FIG. 3C).

Figure 4B:
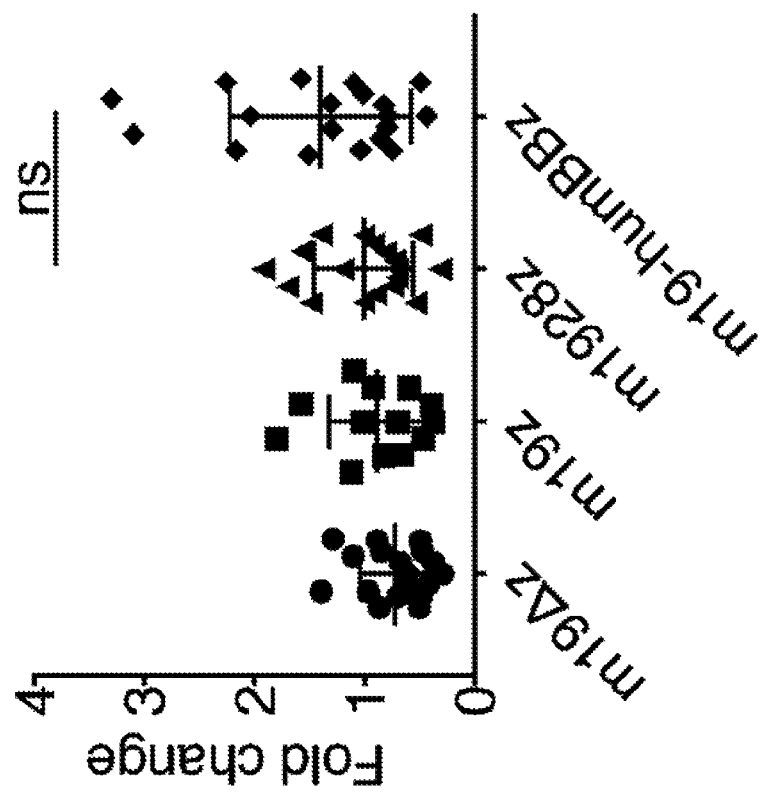
FIG. 4 shows m19-humBBz CAR T cells have higher anti-apoptotic protein expression than m1928z CAR T cells. Viability (A) and proliferation (B) of mCD19-targeted CAR T cells. CAR T cells were produced and proliferation was evaluated by fold change from the initial cell number to final cell yield at Day 4. Cell viability was measured by trypan blue staining on an automated cell counter (BIO-RAD). Data were pooled from 17 (viability) and 19 (proliferation) independent productions. (C) BCL2 and BCL-XL expression in CAR T cells by flow cytometry. Day 4 CAR T cells were intracellularly stained with anti-BCL2 and anti-BCL-XL antibodies and subjected to flow cytometry. Cells were pre-gated on live CAR T cells. Data are representative of two independent experiments. (D) BCL2 and BCL-XL protein expression after antigen stimulation. One million day 4 CAR T cells were stimulated on 1×105 3T3-mCD19 cells for 4 hr. Cell lysates from CAR T cells were prepared, BCA quantitated, normalized to total protein, and subjected to Western blot. Western blots are representative of two independent experiments. Semi-quantitation of Western blots was done using ImageJ software. BCL2 and BCL-XL expression in different CAR T cells were compared by normalizing to β-ACTIN. All data, unpaired t test. ns, not significant.
Figure 4A:
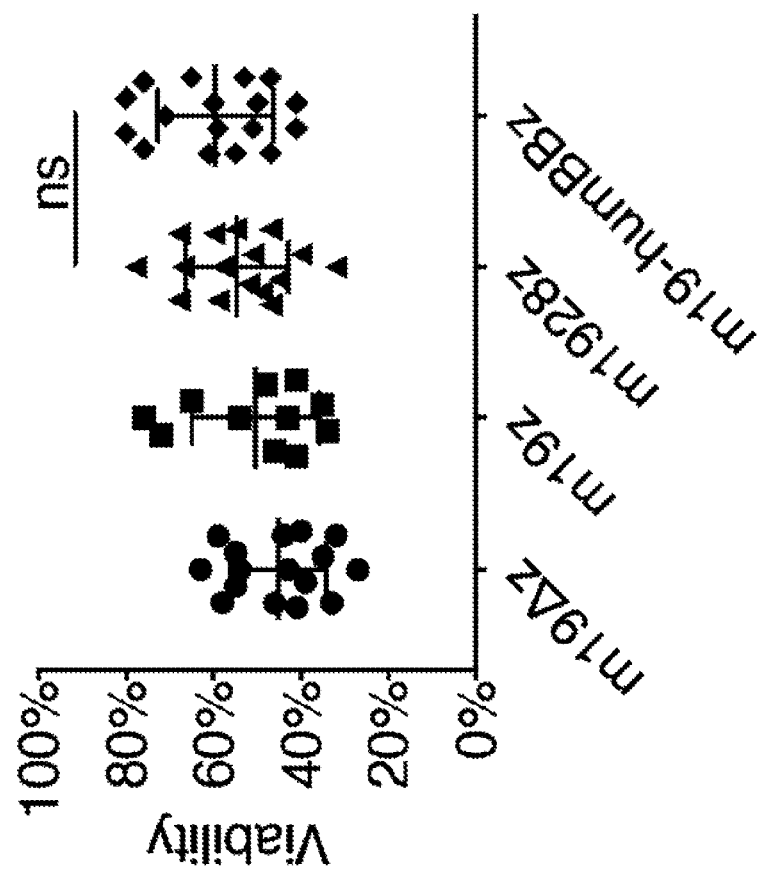
Figure 4C:
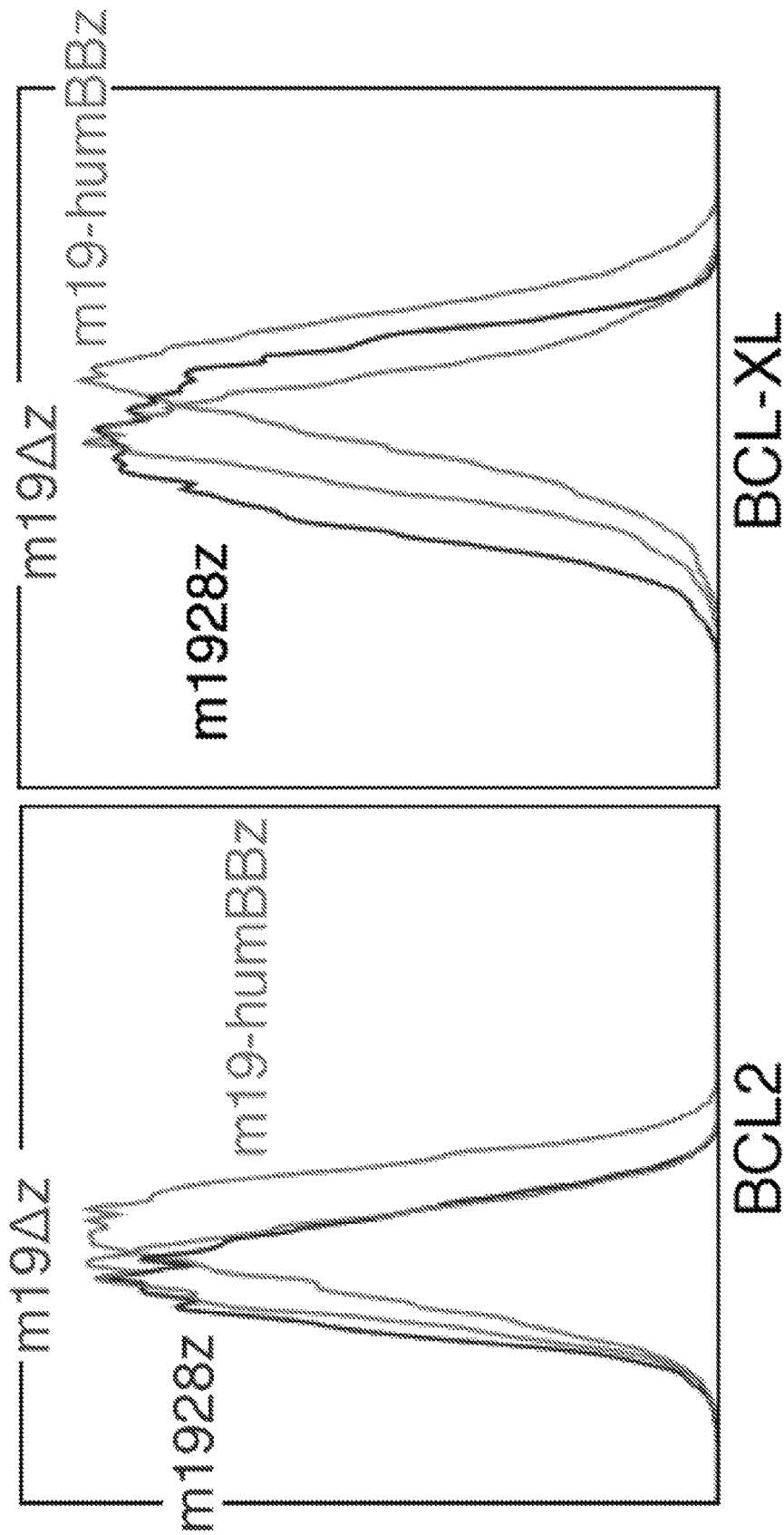
Figure 4D:
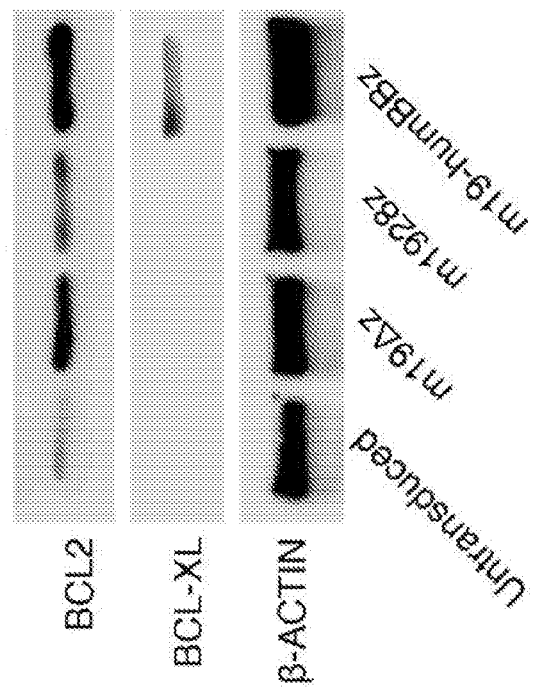

With evidence of enhanced in vivo persistence and previous studies demonstrating that 4-1BB co-stimulation is essential for T cell survival and anti-apoptosis (Lee H W, et al. J Immunol. 2002 169(9):4882-8) we evaluated CAR T cell viability and proliferation. From multiple independent productions, m19-humBBz CAR T cells showed a slightly increased, although not significantly higher viability and proliferation than m1928z CAR T cells (FIGS. 4A and 4B). We also evaluated the expression of anti-apoptotic proteins, BCL2 and BCL-XL, by flow cytometry. Without antigen stimulation m19-humBBz CAR T cells have 1.6-fold higher BCL2 (MFI 1107 vs. 668) and 1.9-fold higher BCL-XL (MFI 6185 vs. 3305) than m1928z CAR T cells (FIG. 4C). We also evaluated the expression of anti-apoptotic proteins by Western blotting after antigen-stimulation. The m19-humBBz CAR T cells have greater BCL2 (3.6 vs. 1.8) and BCL-XL (5.7 vs. 0.01) expression than m1928z CAR T cells after normalization to β-ACTIN (FIG. 4D).

Figure 13A:
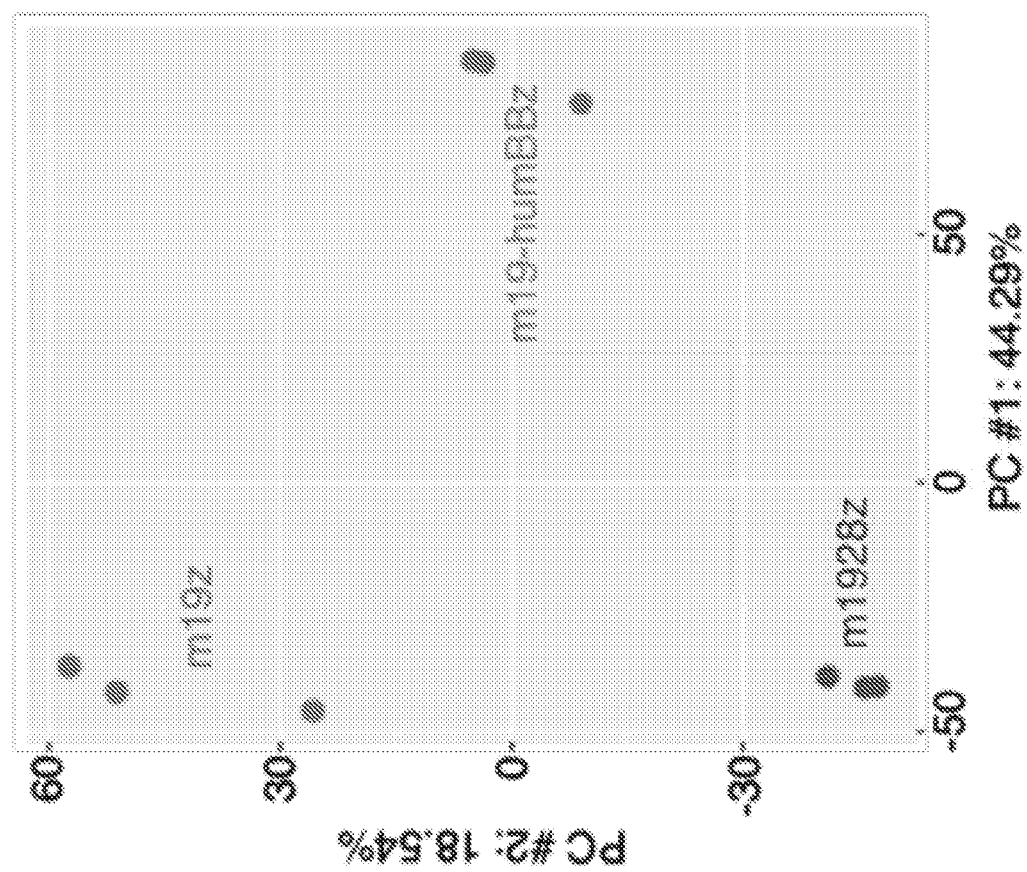
Figure 13B:
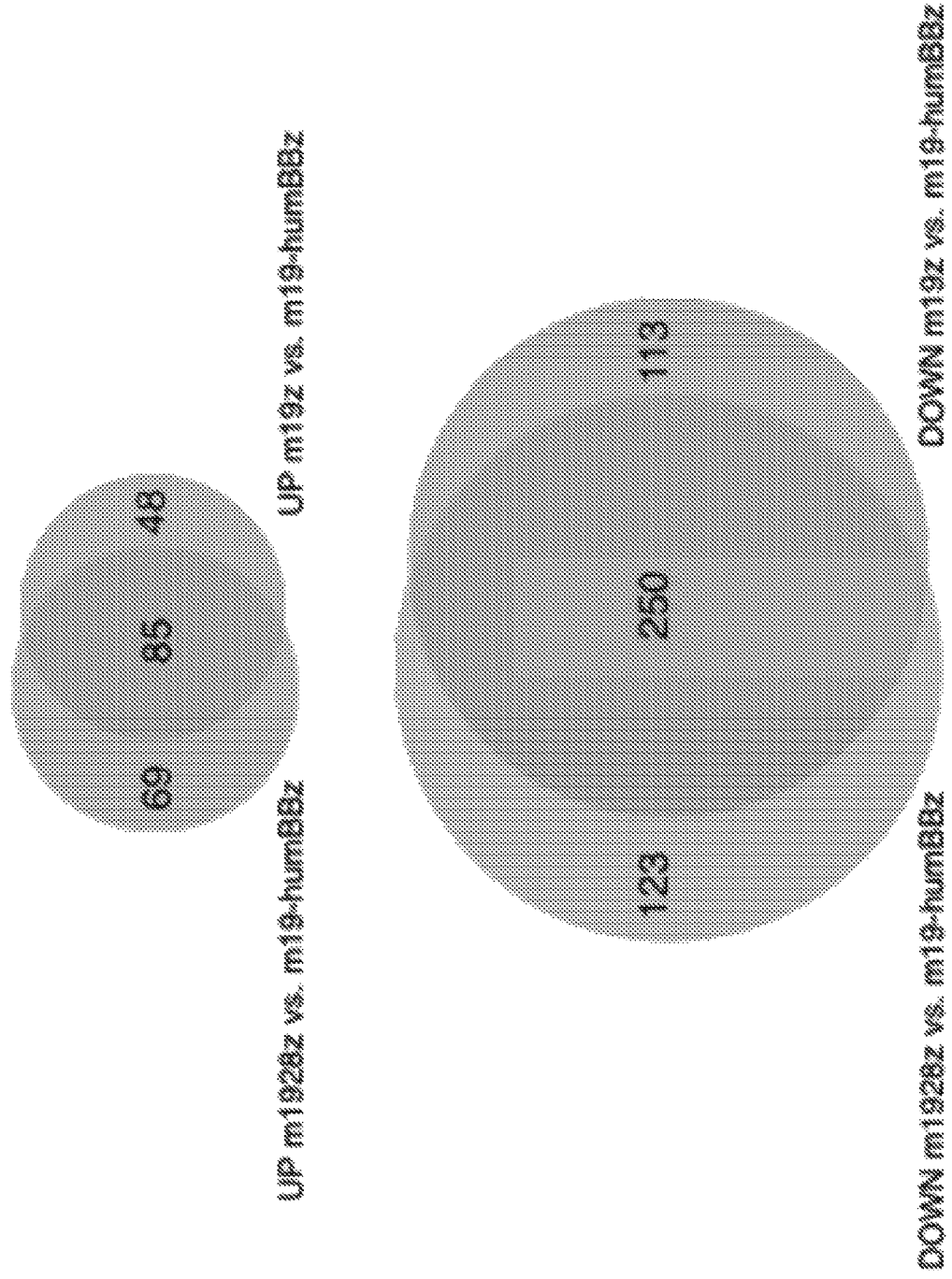
Figure 13C:
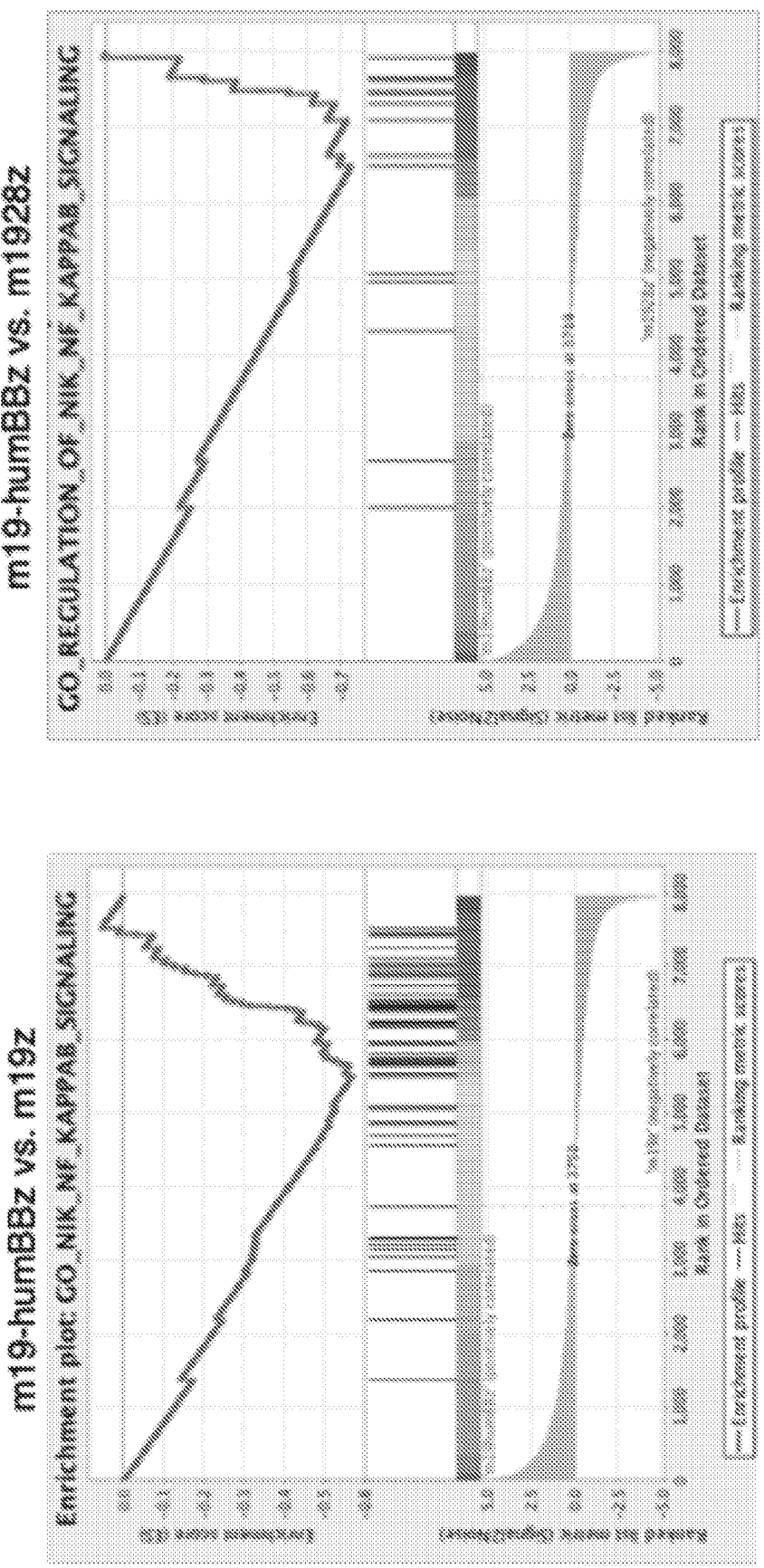

4-1BB Co-Stimulation Induces Greater NF-κB than CD28 Co-Stimulation in Mouse CAR T Cells We sought to identify signaling pathways that regulate in vivo persistence in CAR T cells to optimize these pathways and further enhance persistence since loss of CAR T cells lead to relapses in patients (Maude S L, et al. N Engl J Med. 2014 371(16):1507-17). Therefore, we sorted m19z, m19-humBBz, and m1928z CAR T cells after antigen-stimulation and performed RNA-SEQ, which confirmed each CAR group had a unique transcriptional profile (FIGS. 13A and 13B). Gene set Enrichment Analysis (GSEA) revealed enrichment for pathways that regulate NF-κB when comparing CAR T cells that co-stimulate 4-1BB vs. CD28 or lack co-stimulation (FIG. 13C). NF-κB is a key regulator of T cell survival (Watts T H. Annu Rev Immunol. 2005 23:23-68) as well as anti-tumor control (Barnes S E, et al. J Immunother Cancer. 2015 3(1):1) so we evaluated if differential levels of NF-κB account for enhanced in vivo CAR T cell persistence and/or function of m19-humBBz CAR T cells. Mechanistic studies (Arch R H, et al. Mol Cell Biol. 1998 18(1):558-65) of 4-1BB co-stimulation have been performed with 293 cells transduced with wild-type 4-1BB. We utilized a similar reporter cell line, NF-κB/293/GFP-Luc, which allows measurement of GFP fluorescence as an indicator of NF-κB signaling. Mouse CD19 targeted CARs were retrovirally transduced into NF-κB/293/GFP-Luc reporter cells and only m19-humBBz transduction induced NF-κB (FIG. 5A). We validated this observation in primary mCD19-targeted CAR T cells stimulated with antigen. CAR T cells were produced from NF-κB-RE-luc transgenic mice, which have a firefly luciferase transgene regulated by NF-κB responsive elements (Carlsen H, et al. J Immunol. 2002 168(3):1441-6). After 4 hr stimulation with 3T3-mCD19 AAPC, CAR T cell lysates were prepared and evaluated for bioluminescence. Compared to m19Δz, NF-κB signaling increased by 29-fold in m19-humBBz CAR T cells and about 5-fold in m1928z CAR T cells (FIG. 5B).

Mutations of the 4-1BB Co-Stimulatory Domain Modulate NF-κB and In Vitro Function of Human CD19-Targeted CAR T Cells We demonstrated that mCD19-targeted T cells with a CAR containing a 4-1BB domain have enhanced proliferation and NF-κB signaling. We wanted to validate these observations in primary human T cells and extend them by directly evaluating if NF-κB signaling correlated with CAR T cell viability and proliferation. We developed human CD19 (hCD19) targeted CARs (FIG. 5C) containing a wild-type (h19BBz) or mutated 4-1BB endodomain (mut01- mut04) to modulate NF-κB signaling. The 41BB endodomain mutants were located in previously identified (Jang I K, et al. Biochem Biophys Res Commun. 1998 242(3):613-20; Arch R H, et al. Mol Cell Biol. 1998 18(1):558-65; Saoulli K, et al. J Exp Med. 1998 187(11):1849-62; Ye H, et al. Mol Cell. 1999 4(3):321-30) TRAF1-3 binding domains. We measured the ability of the hCD19-targeted CARs to induce NF-κB in reporter cells. The h19BBz CAR and one with double 4-1BB endodomains (mut04) had high (26%) and moderate (12%) levels of NF-κB upregulation respectively (FIG. 5D). However, all three CARs with mutated TRAF binding domains (mut01-03) showed minimal NF-κB induction after transduction (FIG. 5D). Next, we evaluated how these differential levels of NF-κB signaling impact in vitro function of human T cells. We retrovirally transduced healthy donor human T cells with the h19BBz or mutated CARs, which displayed similar gene transfer and CD4/CD8 ratios (FIG. 14). Cell growth was monitored after stimulation with 3T3-hCD19 AAPC. Human CAR T cells with greater levels of NF-κB signaling (h19BBz and mut04) also had the greatest viability (70-74.3%) compared to CAR T cells with mutations (mut01-mut03, 55.3-65.6%) in the TRAF binding domains (FIG. 5E). Similarly, both h19BBz and mut04 hCD19-targeted CAR T cells proliferated significantly greater (18.6- and 12.2-fold, respectively) than mut01-mut03 hCD19-targeted CAR T cells (approximately 5-fold, FIG. 5F). However, at an E:T ratio of 10:1 all groups of CAR T cells killed 3T3-hCD19 cells similarly despite differences in NF-κB signaling (FIG. 5G).

TRAF1/NF-κB is Required for Optimal m19-humBBz CAR T Cell Function In Vivo

Studies have demonstrated that NF-κB signaling in T cells is mediated, at least in part, through the binding of TRAF1-3 to the intracellular domain of 4-1BB (Jang I K, et al. Biochem Biophys Res Commun. 1998 242(3):613-20; Arch R H, et al. Mol Cell Biol. 1998 18(1):558-65; McPherson A J, et al. J Biol Chem. 2012 287(27):23010-9; Saoulli K, et al. J Exp Med. 1998 187(11):1849-62; Ye H, et al. Mol Cell. 1999 4(3):321-30). It is speculated that TRAF2 is critical for enhanced function mediated by 4-1BB co-stimulation in CAR T cells but no direct evidence exists (Zhao Z, et al. Cancer Cell. 2015 28(4):415-28; Gomes-Silva D, et al. Cell Rep. 2017 21(1):17-26). Furthermore, our analyses of the function of human T cells modified with CARs containing mutated 4-1 BB (FIG. 5D) demonstrates that NF-κB signaling correlates with hCD19-targeted CAR T cell proliferation and viability but cannot distinguish which TRAFs are modulating NF-κB since the targeted domains can bind TRAF1, 2, or 3. Therefore, we applied our models to determine if TRAF1, TRAF2, or TRAF3 regulated NF-κB signaling and CAR T cell function.

We introduced TRAF dominant negative (DN) proteins into NF-κB/293/GFP-Luc reporter cells followed by m19-humBBz CAR transduction. Gene-transfer for CAR and TRAF DN proteins was confirmed by flow cytometry (FIG. 6A). Compared to cells transduced with only m19-humBBz, NF-κB signaling with TRAF1 DN decreased (FIG. 6A, GFP %: 45.5% vs. 13.4%; GFP MFI: 10929 vs. 1688). The TRAF3 DN group also displayed decreased NF-κB (FIG. 6A, GFP %: 45.5% vs. 30.8%; GFP MFI: 10929 vs. 6056), although not to the same extent as the TRAF1 DN group. In contrast, NF-κB signaling in the TRAF2 DN group was greater than the m19-humBBz control (FIG. 6A, GFP+%: 63.5% vs. 45.5%; GFP MFI: 14309 vs. 10929). We also evaluated if TRAF1 could be identified binding to the CAR. After transduction of NF-κB/293/GFP-Luc reporter cells with the m19-humBBz CAR we isolated the CAR by Protein L binding and assayed for retention of TRAF1. We detected TRAF1 in both the total protein lysate as well as the immunoprecipitate confirming that TRAF1 binds to the m19-humBBz CAR (FIG. 6B).

We aimed to validate that TRAF1 was required for 4-1 BB co-stimulatory enhancement of mCD19-targeted CAR T cell function by evaluating CAR T cells, derived from wild type C57BL/6 mice or Traf1$^{-/-}$ (Tsitsikov E N, et al. Immunity. 2001 15(4):647-57) mice, after adoptive transfer into immune competent mice. For immune phenotype both m1928z and m19-humBBz Traf1$^{-/-}$ CAR T cells have a higher CD4/CD8 ratio and a greater frequency of central memory cells (CD62L+CD44+) (FIG. 15). Also, m19-humBBz Traf1-/- CAR T cells had significantly lower viability and proliferation than m19-humBBz wild type CAR T cells, but m1928z CAR T cell viability or proliferation was not significantly affected by lack of TRAF1 (FIG. 6C). In vivo, B cells recovered 2 weeks after treatment with m19-humBBz Traf1-/- CAR T cells, while m19-humBBz wild type CAR T cells maintained B cell aplasia (FIG. 6D). Correspondingly, CAR T cell persistence in the m19-humBBz Traf1-/- group was significantly decreased compared to the m19-humBBz wild type CAR T cell group (FIG. 6D). However, the persistence of m1928z CAR T cells, or B cell killing, was not significantly reduced when the donor T cells were TRAF1 deficient (FIG. 6D).

Increasing NF-k B Signaling Enhances CAR T Cell Function

Figures 16A, 16B, 16C:
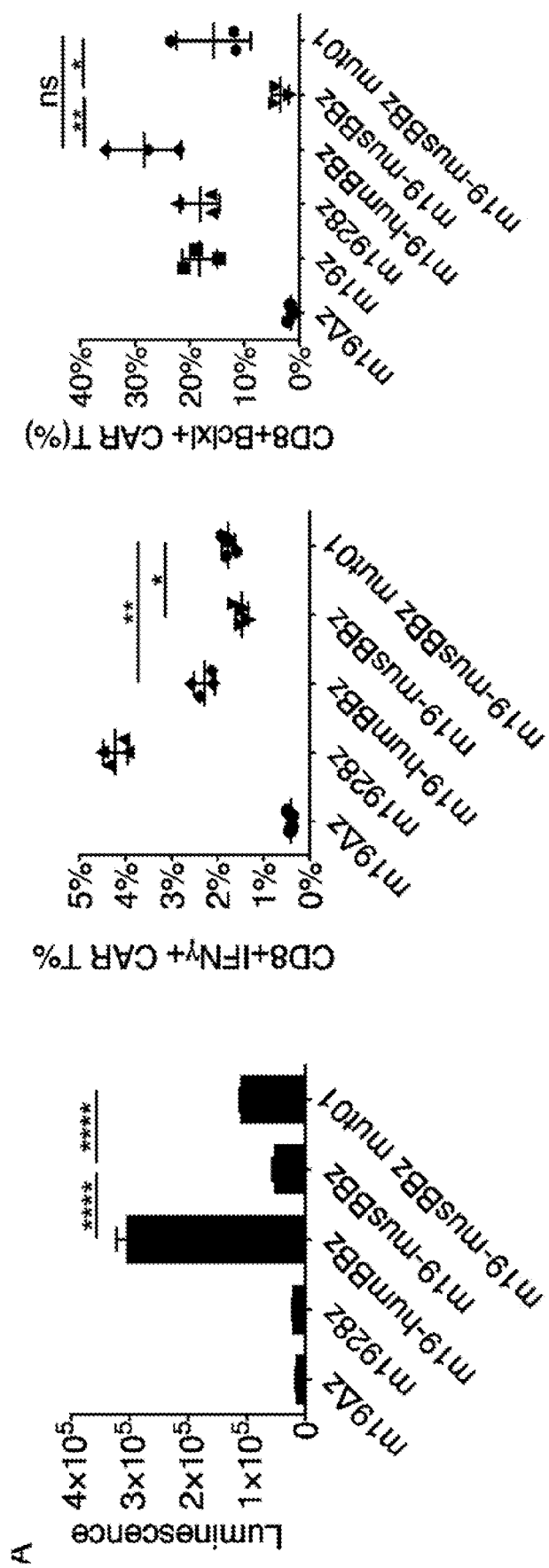
Figure 16D:
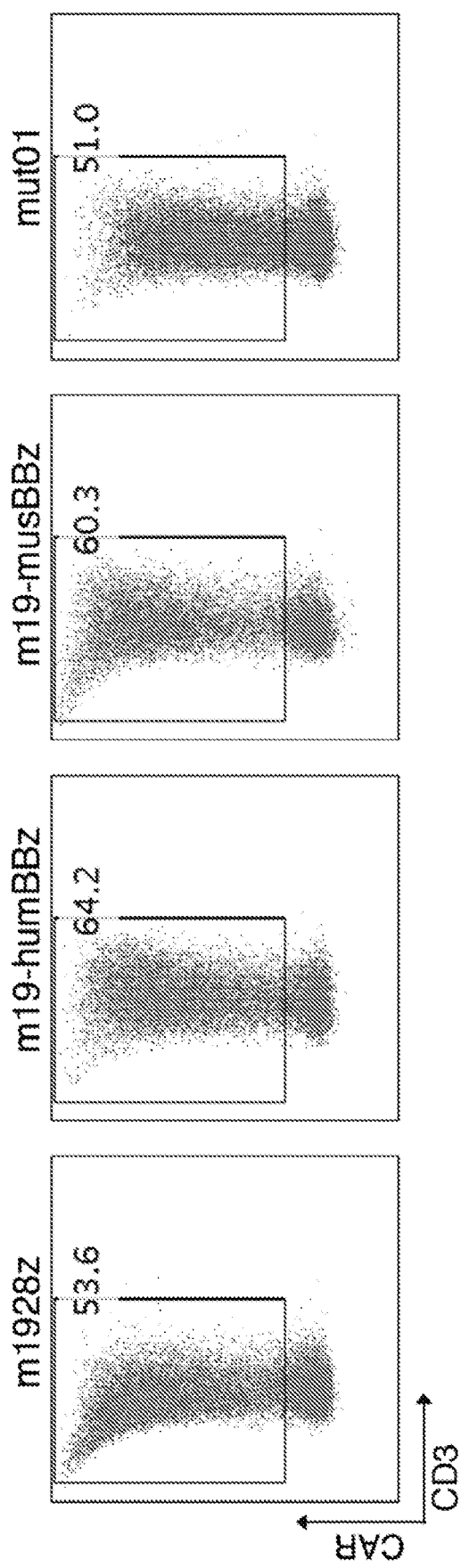

We hypothesize that the reduced efficacy of m19-musBBz CAR T cells is due to sub-optimal NF-κB signaling and can be optimized by mutations that enhance NF-κB signaling. Therefore, we created a m19-musBBz mut01 CAR that substituted the first 5 N-terminal amino acid mismatches (underlined in FIG. 2A) of mouse 4-1 BB with human 4-1 BB amino acids. This region of human 4-1 BB has been previously identified to bind TRAF3 greater than its mouse counterpart (Arch R H, et al. Mol Cell Biol. 1998 18(1):558-65), which we characterized as being required for optimal NF-κB (FIG. 6A). Using NF-κB-RE-luc transgenic mice as donors of T cells we demonstrated that m19-musBBz mut01 CAR T cells have about 2-fold greater NF-κB signaling compared to m19-musBBz, which correlated with increased cytokine production and anti-apoptotic protein production (FIG. 16A-16C). In vivo evaluation of m19-musBBz mut01 demonstrated B cell killing and CAR T cell persistence similar to m19-humBBz and significantly greater than m19-musBBz (FIG. 16D-16G).

Figure 17A:
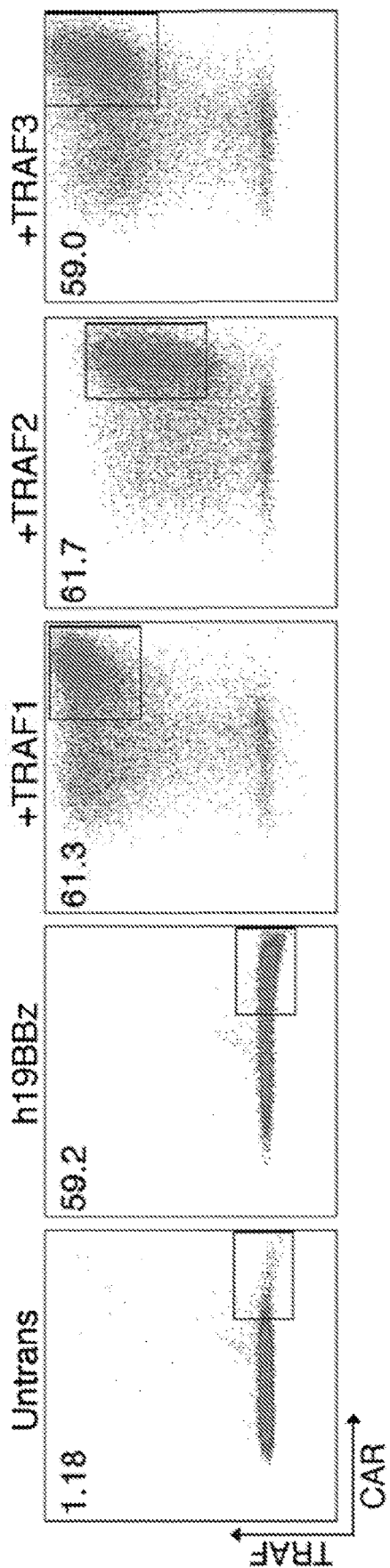
Figure 17B:
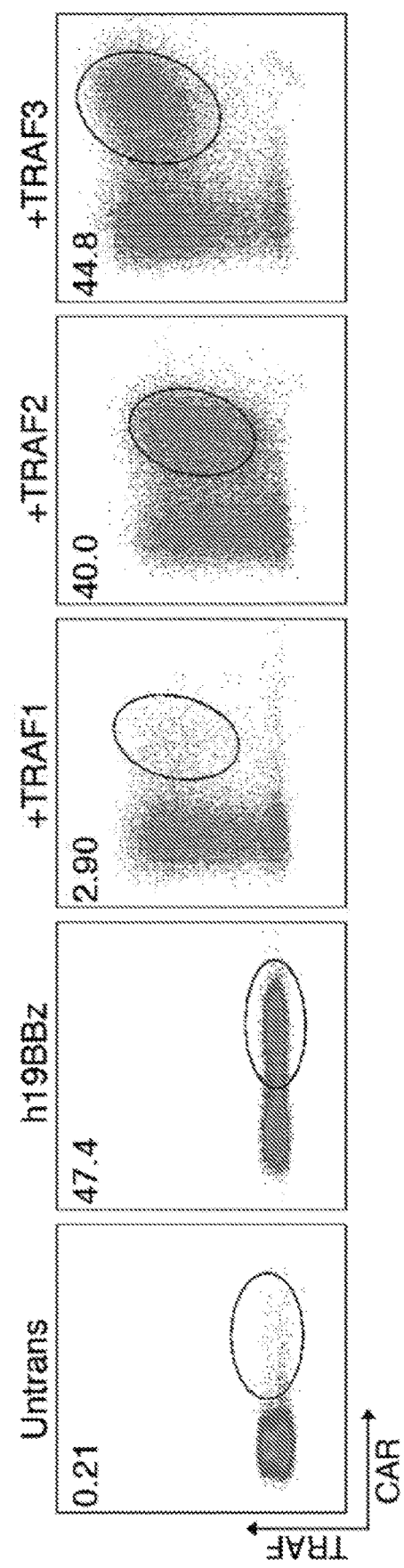
Figure 17C:
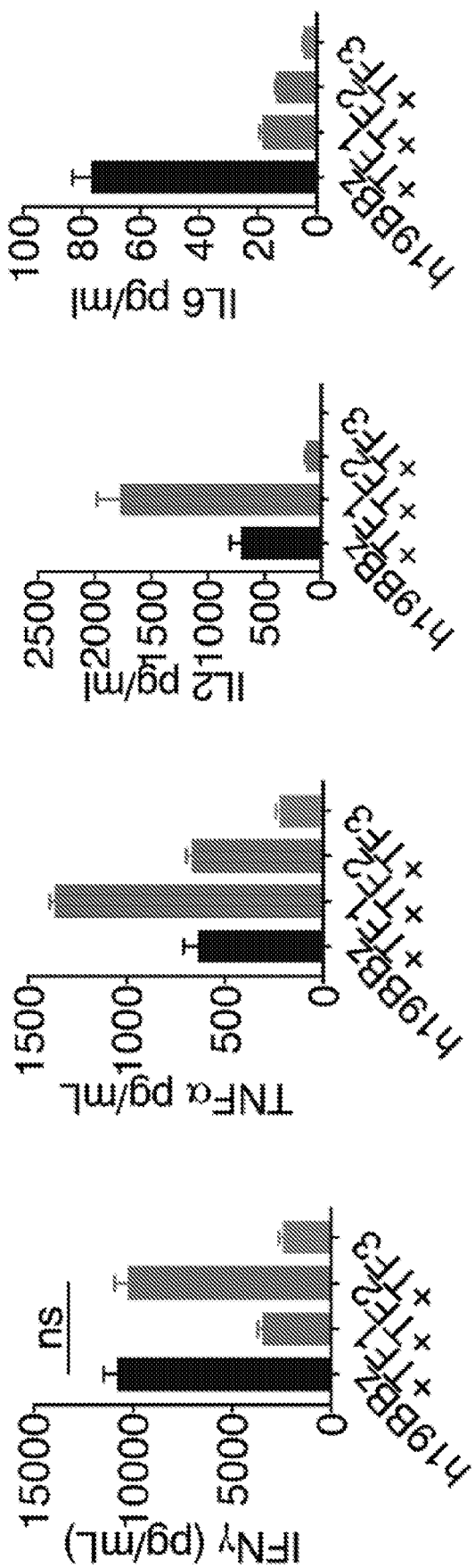
Figure 18A:
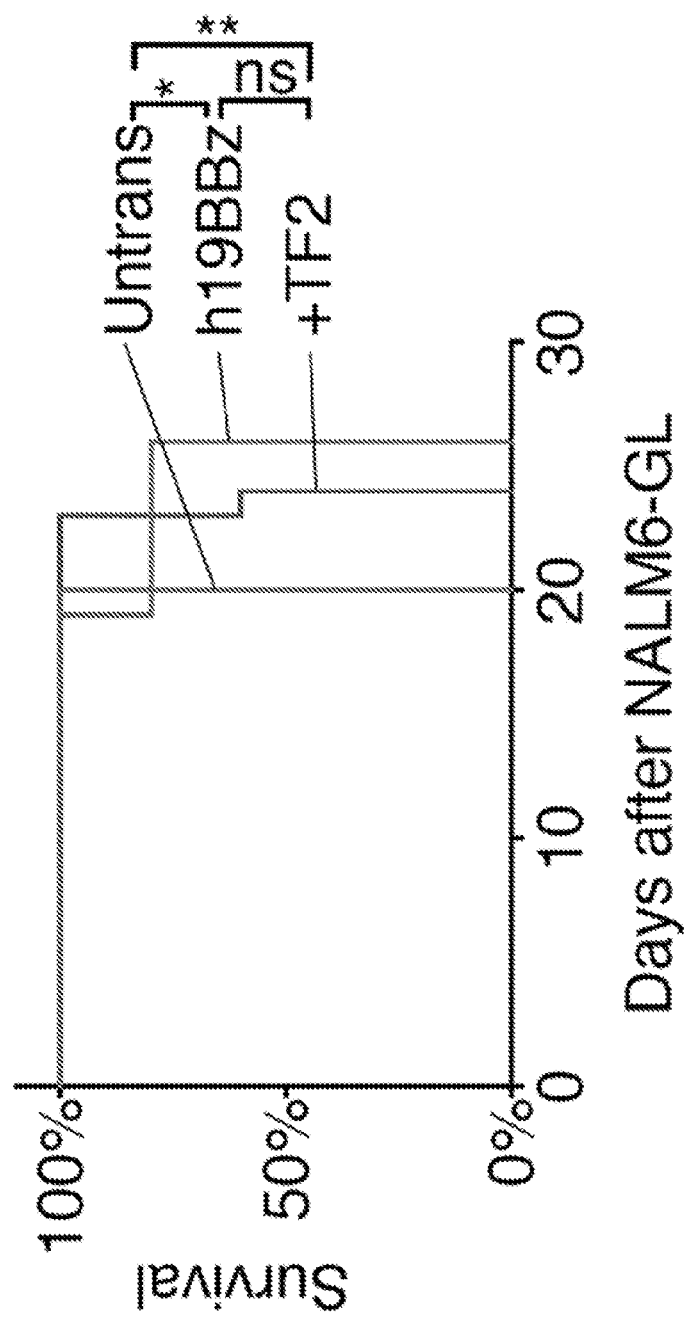
Figures 18B, 18C:
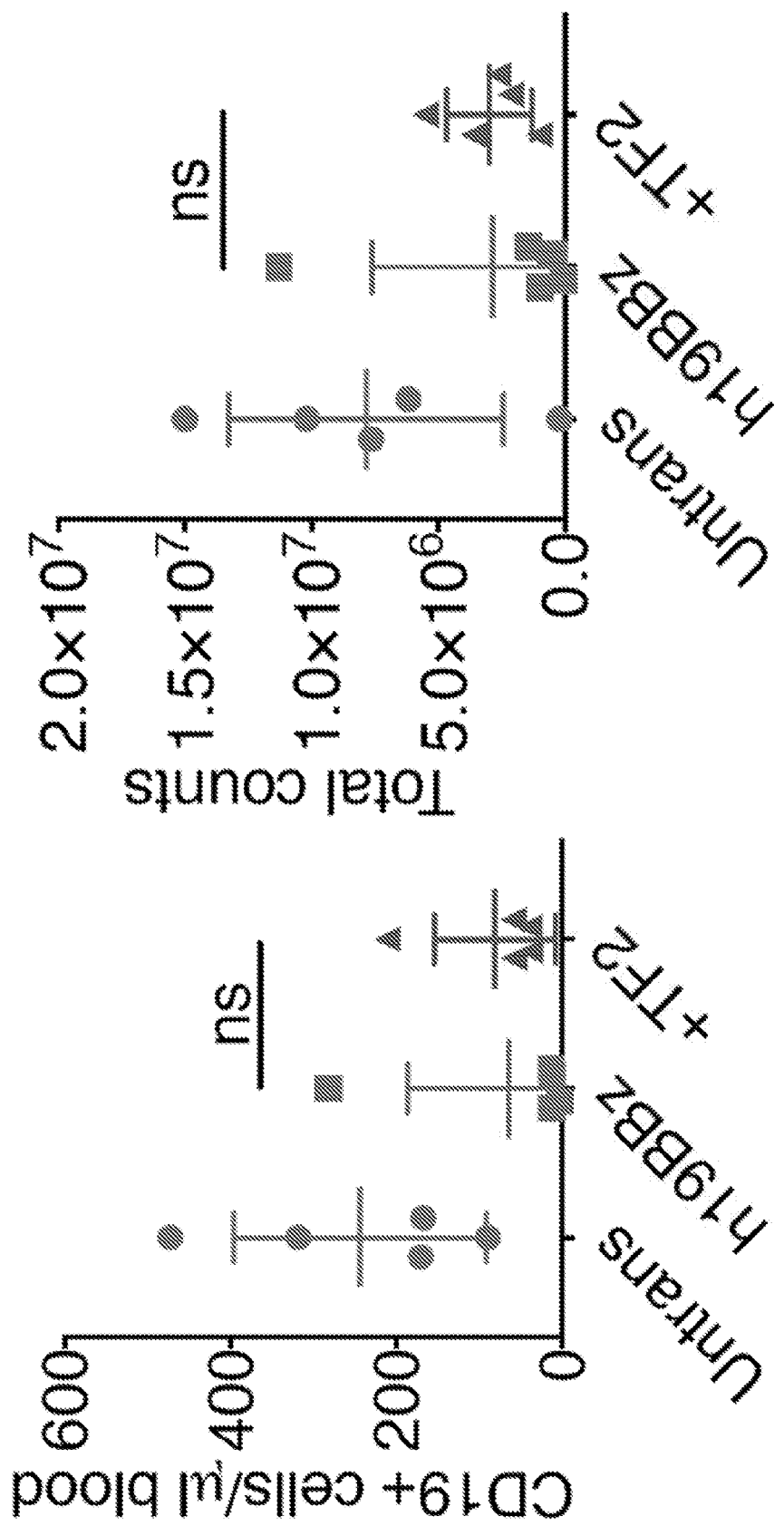
Figure 18D:
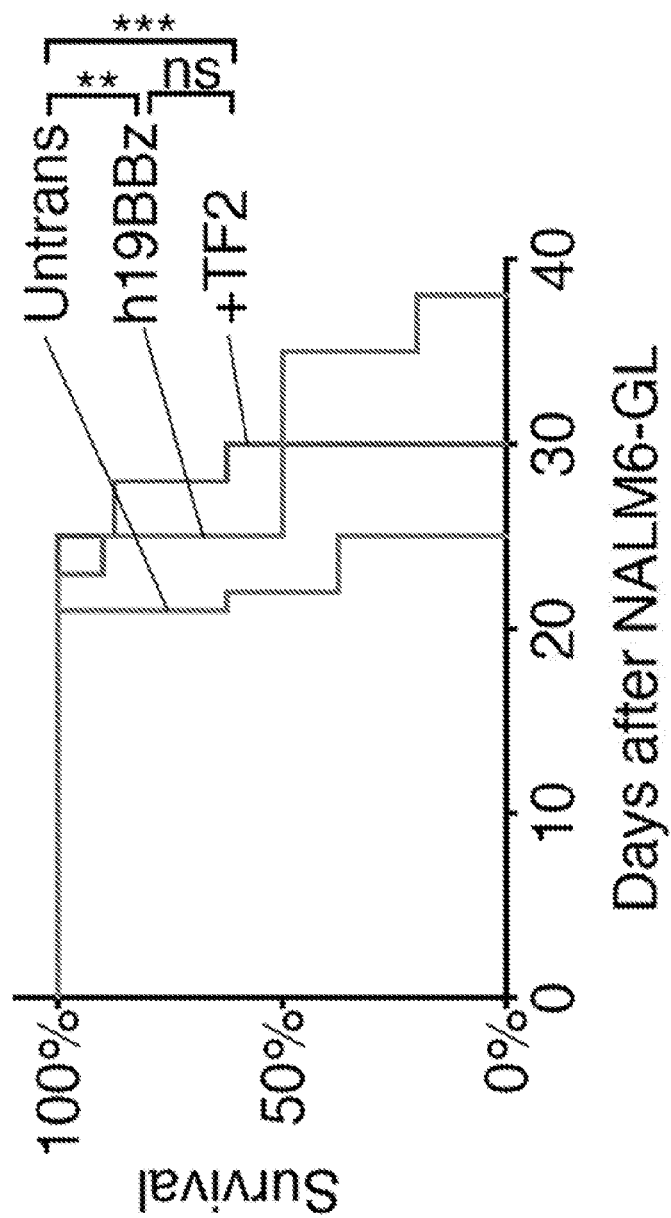
Figure 18F:
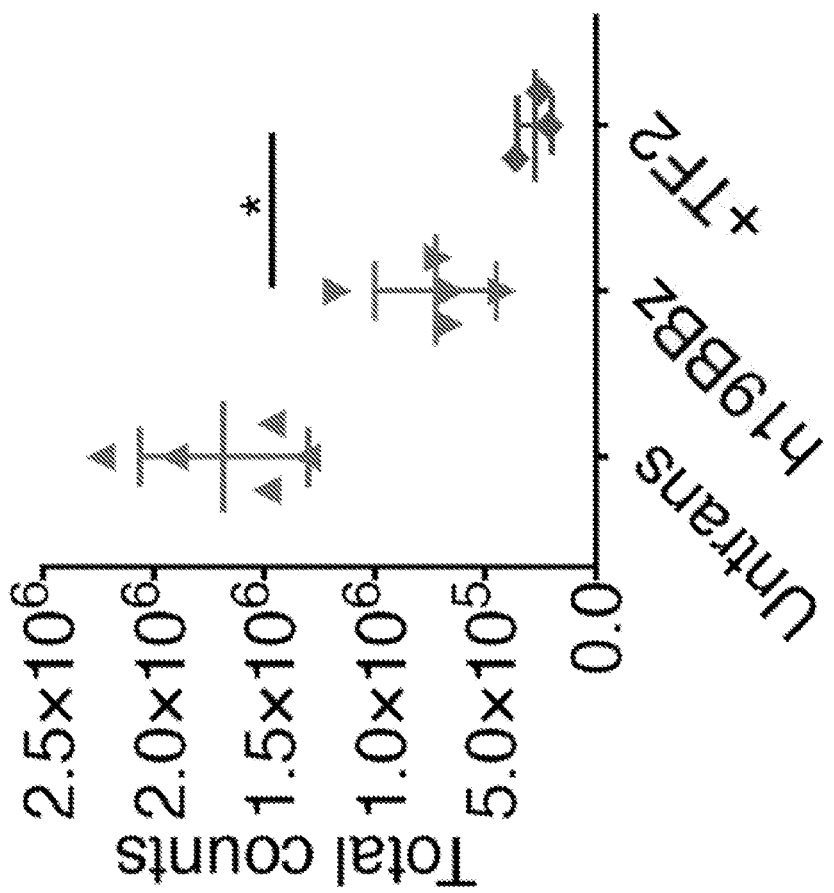
Figure 18E:
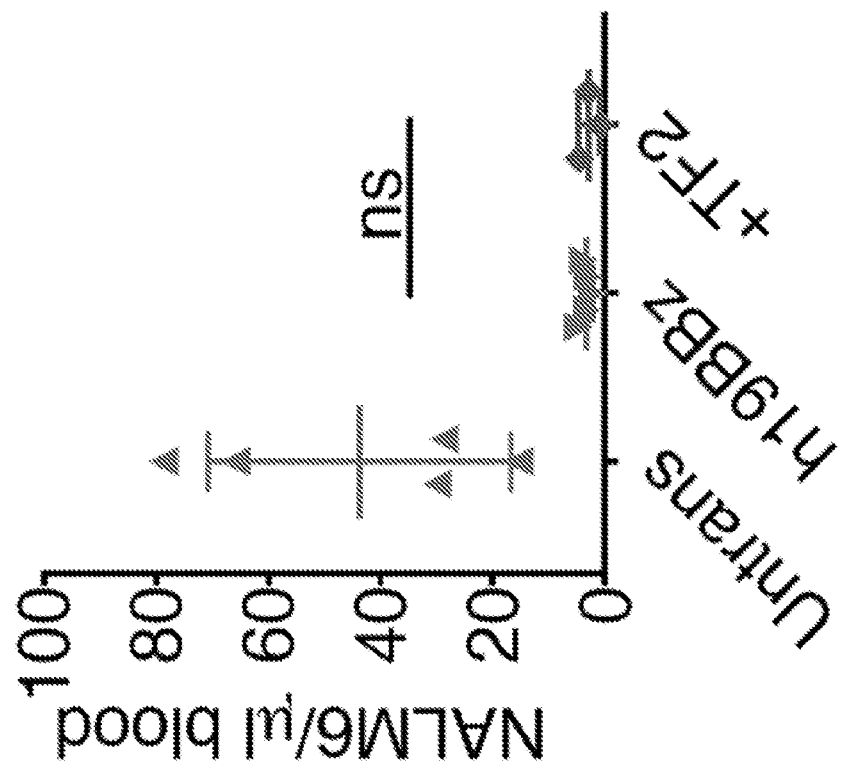

While mutating the 4-1BB co-stimulatory domain to increase TRAF binding and NF-κB signaling is one strategy to enhance CAR T cell function we aimed to demonstrate that another is to provide excess TRAF proteins in CAR T cells that utilize 4-1BB co-stimulation. We co-transduced the h19BBz CARs and TRAFs in the NF-κB/293/GFP-Luc reporter cells. Compared to reporter cells transduced with the h19BBz CAR alone TRAF2 supported a dramatic increase in NF-κB while excess TRAF1 or TRAF3 had negligible effects (FIG. 7A). We also co-transduced primary human T cells with h19BBz and TRAFs to evaluate the impact on CAR T cell function. Both TRAF2 and TRAF3 transduction significantly increased viability, proliferation and target-killing of h19BBz CAR T cells (FIGS. 7B-7D). However, co-transduction of TRAF1 with h19BBz CAR T cells resulted in decreased viability, proliferation and target-killing of h19BBz CAR T cells, which may be due to reduced CAR expression (FIGS. 17A-17B). Increased TRAF expression also modulates cytokine production after antigen stimulation (FIG. 17C). We also compared the in vivo activity of NSG mice treated with the NALM6 leukemia cell line followed by the adoptive transfer of h19BBz CAR T cells with or without excess TRAF2 (FIG. 18). Both h19BBz CAR T cell groups enhanced leukemia killing and survival compared to untransduced T cells, but neither group appeared superior to each other. This may be due to the nature of the aggressiveness of the NALM6/NSG mouse model (Zhao Z, et al. Cancer Cell. 2015 28(4):415-28), which requires rapid leukemia killing so that even 2nd generation CAR T cells do not prevent death.

Figure 7F:
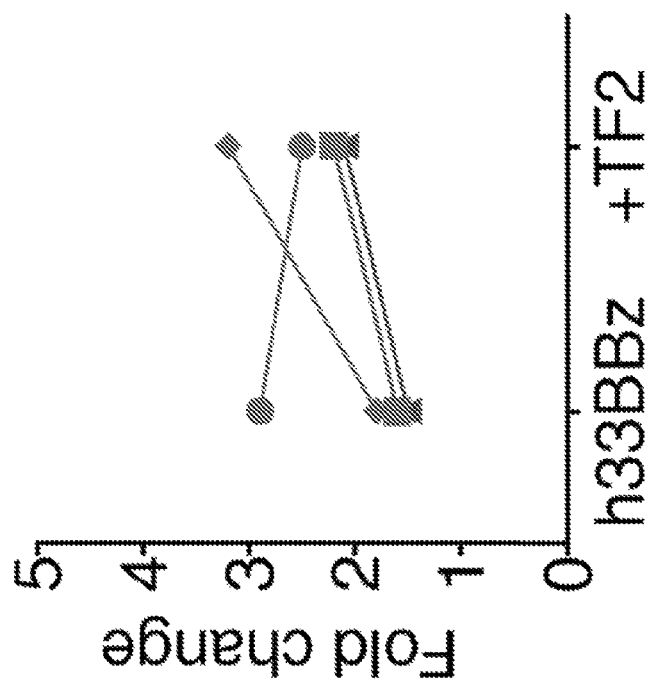
Figure 7E:
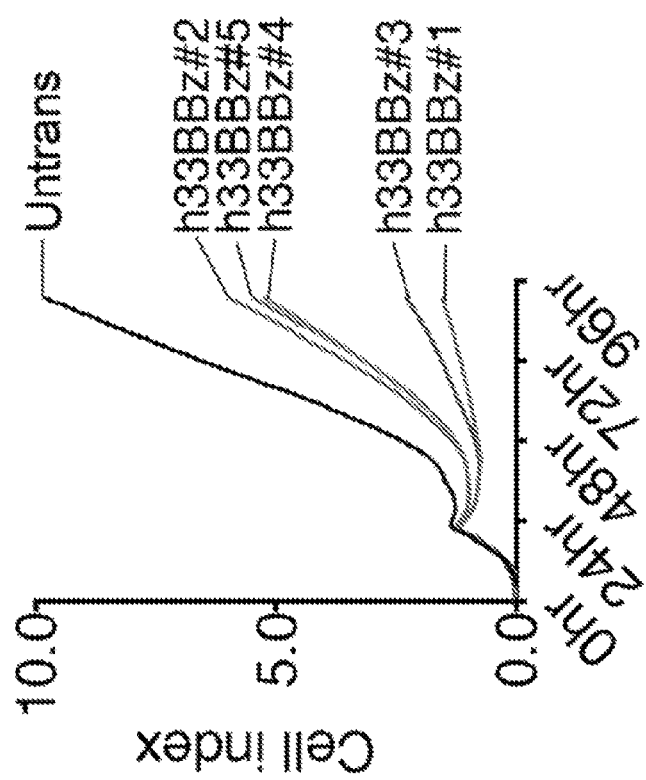
Figure 7G:
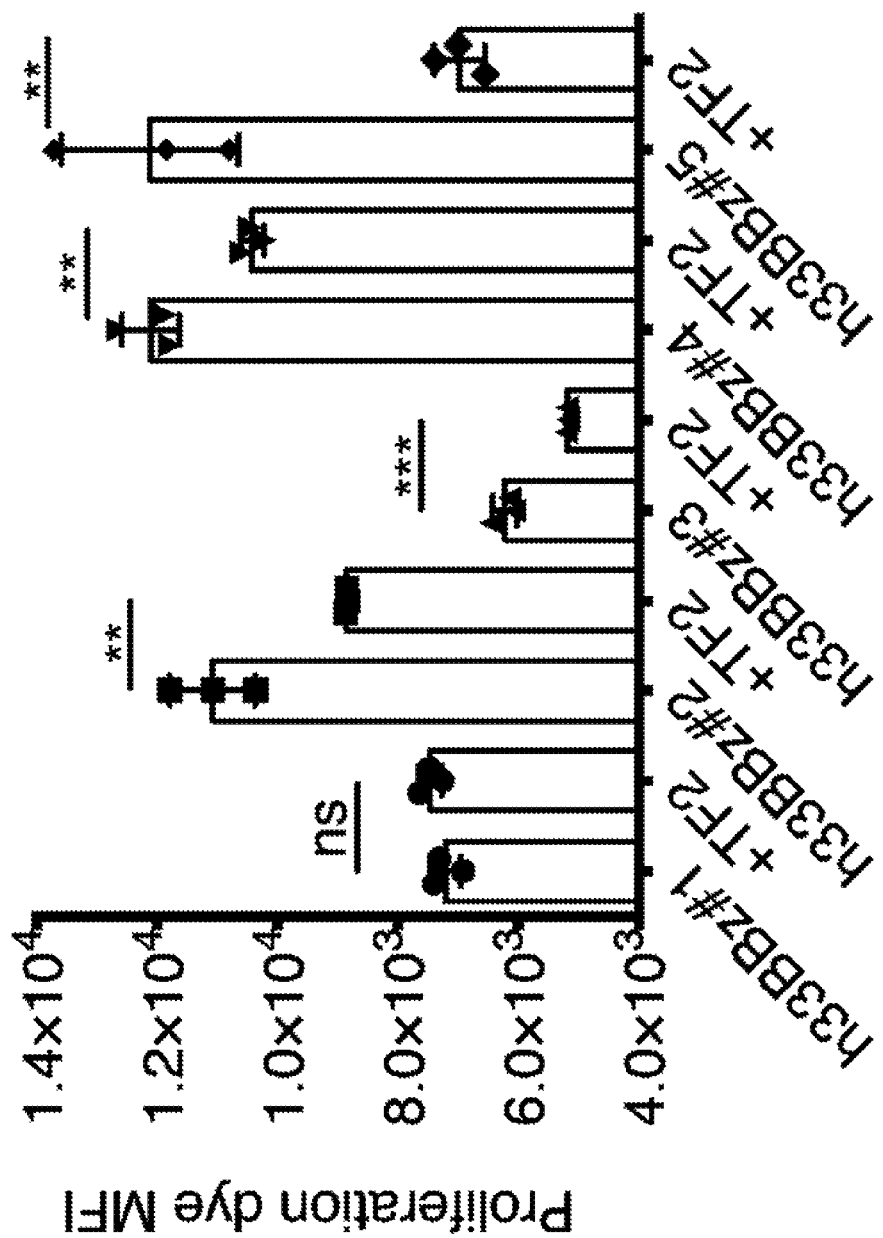

We have demonstrated the role of NF-κB and TRAFs in regulation of both human and mouse CD19-targeted CAR T cell function, however we can not exclude that the CD19 antigen may contribute to these results. Therefore, we evaluated how proliferation of CD33-targeted CAR T cells was impacted by over-expression of TRAF2, which greatly increases NF-κB (FIG. 7A). We created five de novo CD33-targeted CARs with the same design of the h19BBz CAR but replacing the anti-CD19 scFv with an anti-CD33 scFv and followed by the CD8 hinge and transmembrane domain, 4-1BB co-stimulatory domain, and CD3z. We validated the function of our CD33-targeted human CAR T cells by demonstrating cytotoxicity of CD33-positive targets in vitro (FIG. 7E). Over-expression of TRAF2 enhanced the number of CAR T cells produced, as well as their proliferation after antigen-simulation, in four of the five CD33-targeted CAR T cells assayed (FIGS. 7F-7G).

Discussion

In our immune competent animal model high doses of m19-musBBz CAR T cells had equivalent anti-leukemia efficacy as m1928z CAR T cells, however at a stress test dose ($3 \times 10^5$) they had reduced efficacy (FIGS. 1C-1F). We hypothesized that the m19-musBBz CAR was sub-optimal and sequence modifications could increase its efficacy to be equivalent to the m1928z CAR. Therefore, we replaced the mouse 4-1BB endodomain with the human 4-1BB endodomain (m19-humBBz) (FIG. 2). The in vivo function (FIG. 2D) of m19-humBBz CAR T cells was equivalent to m1928z CAR T cells at stress test dose levels, which is consistent with clinical results that demonstrate equivalent CR rates in patients treated with h19BBz or h1928z CAR T cells (Lee D W, et al. Lancet. 2015 385(9967):517-28; Neelapu S S, et al. N Engl J Med. 2017 377(26):2531-44, Maude S L, et al. N Engl J Med. 2018 378(5):439-48; Value in Using CAR T Cells for DLBCL. Cancer Discov. 2018 8(2):131-2). However, the in vitro function of m19-humBBz CAR T cells, as measured by cytokine production and cytotoxicity, was inferior compared to m1928z CAR T cells (FIGS. 2B and 2C). These results are consistent with prior studies that demonstrated human CAR T cells provided CD28 co-stimulation secreted cytokines, such as IL2, IFNγ and TNFα, at greater levels than CARs with 4-1BB co-stimulatory domains (Imai C, et al. Leukemia. 2004 18(4): 676-84; Milone M C, et al. Mol Ther. 2009 17(8):1453-64; Brentjens R J, et al. Clin Cancer Res. 2007 13(18 Pt 1):5426-35; Zhong X S, et al. Mol Ther. 2010 18(2):413-20).

Efficacious in vivo leukemia eradication despite inferior in vitro function appeared inconsistent with an optimal cytotoxic CAR T cell so we evaluated potential mechanisms that could compensate. Others (Zhao Z, et al. Cancer Cell. 2015 28(4):415-28) have observed increased persistence of h19BBz CAR T cells supported enhanced malignant B cell killing in immune deficient mice but the tumor killing was not equivalent to h1928z CAR T cells and all the mice in this study died rapidly from leukemia progression regardless of CAR evaluated. We considered that antigen may be a confounding variable between the previous study and ours (FIGS. 1 and 2) in light of a recent study that demonstrated CAR T cell exhaustion could be induced upon engagement of antigen in TCR-transgenic immune competent mouse models (Yang Y, et al. Sci Transl Med. 2017 9(417)). Therefore, we compared persistence in Rag1$^{-/-}$ mice and determined that mouse T cells modified with a CAR containing the 4-1BB co-stimulatory domain supported the greatest persistence (FIG. 3A). Furthermore, when we irradiated mCD19-targeted CAR T cells before infusion into immune competent mice only m19-humBBz CAR T cells had significantly reduced persistence and B cell killing, while m1928z CAR T cell persistence and B cell killing was not significantly affected, demonstrating that persistence is critical for enhancement of in vivo CAR T cell function mediated by 4-1BB co-stimulation (FIG. 3).

Additional support of the enhanced persistence of CAR T cells with 4-1BB co-stimulation is the increase of anti-apoptotic proteins in m19-humBBz CAR T cells, which is a novel observation (FIG. 4). We compared gene expression of the mCD19-targeted CAR T cell groups to identify pathways that could contribute to enhanced anti-apoptosis and/or persistence imparted by 4-1BB co-stimulation. GSEA demonstrated that m19-humBBz differed in expression of a NF-κB regulatory pathway when compared to m19z or m1928z CAR T cells, which was similar to enrichment of NF-κB regulatory genes in m19-musBBz (Tables 1-4 and FIG. 13). Using a 293 reporter cell line we identified NF-κB signaling only with the m19-humBBz CAR and also validated that NF-κB signaling is enhanced in m19-humBBz mouse CAR T cells compared to m1928z mouse CAR T cells (FIGS. 5A and 5B). While NF-κB is known to be critical for T cell function (Watts T H. Annu Rev Immunol. 2005 23:23-68; Barnes S E, et al. J Immunother Cancer. 2015 3(1):1) we determined that the level of NF-κB signaling for CARs with a 4-1BB co-stimulatory domain is much greater than CARs with a CD28 co-stimulatory domain, which likely contributes to the differential in vivo function of CD19-targeted CAR T cells. We also validated our observation in primary human CAR T cells. Mutations of 4-1BB in an anti-human CD19 CAR variably reduced NF-κB, which correlated with the attenuation of viability and/or proliferation (FIGS. 5C-5F). Recent studies suggest that CD28 co-stimulation directs differentiation of human CAR T cells to effector memory, while 4-1BB co-stimulation promotes differentiation to central memory cells (Zhao Z, et al. Cancer Cell. 2015 28(4):415-28; Kawalekar O U, et al. Immunity. 2016 44(2):380-90; Long A H, et al. Nat Med. 2015 21(6):581-90). Furthermore, these studies identified distinct metabolic and gene expression pathways associated with the CD28 or 4-1BB endodomains and they suggest that 4-1BB co-stimulation promotes CAR T cell persistence and protects against CAR T cell exhaustion (Zhao Z, et al. Cancer Cell. 2015 28(4):415-28; Kawalekar O U, et al. Immunity. 2016 44(2):380-90; Long A H, et al. Nat Med. 2015 21(6):581-90). Therefore, we cannot rule out that these distinct metabolic or gene expression patterns after co-stimulation dictate the role of NF-κB signaling in CAR T cells. However, it may also be that NF-κB signaling drives different metabolic or signaling pathways in CAR T cells, which is a hypothesis that we are evaluating. In fact, prior studies have established that NF-κB signaling is required for maintaining memory T cells and can also increase mitochondrial respiration (Knudson K M, et al. Proc Natl Acad Sci USA. 2017 114(9):E1659-E67; Mauro C, et al. Nat Cell Biol. 2011 13(10):1272-9).

Figure 16G:
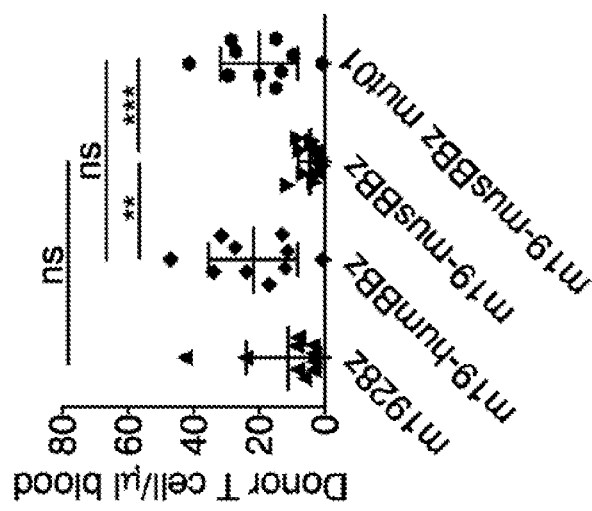
Figure 16F:
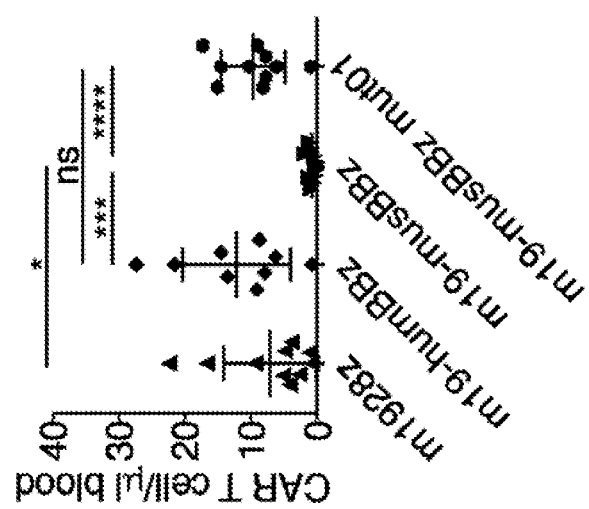
Figure 16E:
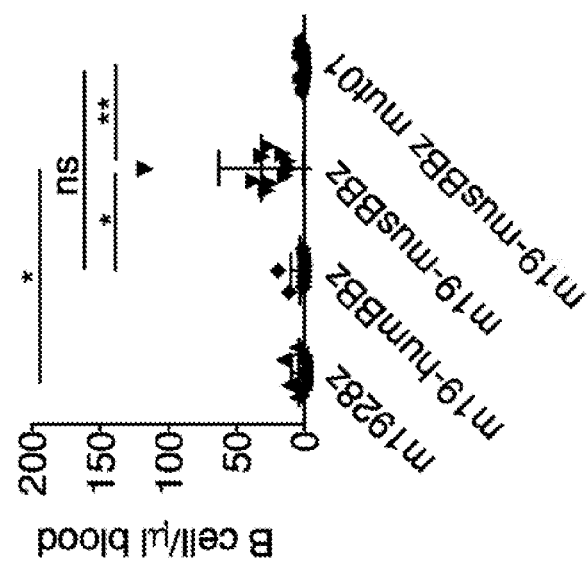

The critical role for NF-κB in 4-1BB co-stimulatory enhancement of CAR T cell function suggests a mechanism for the reduced efficacy of the m19-musBBz CAR. After antigen-stimulation NF-κB signaling of m19-humBBz CAR T cells is 4.7 times greater than m19-musBBz CAR T cells (FIG. 16A). There are a total of 19 aa differences between the mouse and human 4-1BB endodomains and only one of them is located in the QEE domains identified critical for co-stimulation and the Q→E substitution is reported to not affect 4-1BB co-stimulation (Jang I K, et al. Biochem Biophys Res Commun. 1998 242(3):613-20; Arch R H, et al. Mol Cell Biol. 1998 18(1):558-65). By mutating 5 aa in the N-terminal portion of the mouse 4-1BB endodomain we improved NF-κB signaling in mCD19-targeted CAR T cells, which resulted in enhanced cytokine production and anti-apoptotic protein expression, as well as in vivo B cell killing and CAR T persistence (FIG. 16E-16G). Arch and Thompson (Arch R H, et al. Mol Cell Biol. 1998 18(1):558-65) mutated this same domain in mouse 4-1BB and reported that TRAF3 recruitment was enhanced. This suggests that optimization of TRAF recruitment to co-stimulatory domains can enhance CAR T cell function. TRAF proteins regulate T cell function by linking extracellular activation receptors, including 4-1BB, and intracellular signaling pathways thereby impacting T cell differentiation, proliferation, survival and cytokine production (Watts T H. Annu Rev Immunol. 2005 23:23-68; So T, et al. Tohoku J Exp Med. 2015 236(2):139-54). TRAF proteins have been speculated as having multiple roles in transducing 4-1BB co-stimulation in CARs but to date, none have been able to confirm or define their specific roles (Zhao Z, et al. Cancer Cell. 2015 28(4):415-28; Gomes-Silva D, et al. Cell Rep. 2017 21(1): 17-26). Using a 293 reporter we determined that TRAF1 and TRAF3 are required for optimal NF-κB activation by 4-1BB co-stimulation, which we confirmed for TRAF1 in primary mouse CAR T cells (FIG. 6). A TRAF2-DN inhibitor increased NF-κB signaling of m19-humBBz CARs, which may be due to its role in degrading the NF-κB-inducing Kinase (NIK) since it serves as a negative regulator of the alternative NF-κB signaling pathway (Zarnegar B J, et al. Nat Immunol. 2008 9(12):1371-8). While depletion of TRAFs negatively impacted CAR T cell function, overexpressing TRAF2 or TRAF3 in primary human h19BBz CAR T cells enhanced viability, proliferation and cytotoxicity (FIG. 7A-7D). T cells with h19BBz and excess TRAF2 dramatically increased NF-κB compared to h19BBz CAR T cells (7.7-fold) further confirming that increased NF-κB enhances CAR T cell function (FIG. 7A). However, we also observed enhancement of CAR T cell function in some groups that is independent of NF-κB. Human T cells with the h19BBz CAR and excess TRAF3, despite having enhanced function had negligible changes in NF-κB, which suggests TRAF3 may be mediating its potentiating effects through another signaling pathway(s). We suspect this may be through enhancement of endogenous CD28 co-stimulation since TRAF3 is required for TCR/CD28 signaling (Xie P, et al. J Immunol. 2011 186(1):143-55). We also validated our observation for the role of excess TRAF2 in enhancing CAR T cell proliferation with CD33 targeted CAR T cells (FIGS. 7E-7G).

Transduction of TRAFs and CARs into T cells may allow potentiation of both 4-1BB and CD28 costimulation. Combining both TRAFs and CARs may substitute for a third generation CAR design that includes both CD28 and 4-1BB endodomains, which were envisioned with the goal of enhancing both cytotoxicity and persistence (Zhong X S, et al. Mol Ther. 2010 18(2):413-20; Till B G, et al. Blood. 2012 119(17):3940-50). However, both these designs may be hampered by trying to merge phenotypes that are mutually exclusive, although dissociation of the co-stimulary domains have had some success with enhancing third generation CAR T cell function (Zhao Z, et al. Cancer Cell. 2015 28(4):415-28). Furthermore, continuous TRAF enhancement of 4-1BB co-stimulation and NF-κB signaling could result in tonic signaling and CAR T cell death (Gomes-Silva D, et al. Cell Rep. 2017 21(1):17-26) or even carcinogenesis (Park M H, et al. Cells. 2016 5(2)) suggesting that an optimal TRAF+CAR design may require a molecular switch to regulate TRAF expression.

The clinical evaluation of hCD19-targeted CAR T cells in patients has generated promising results, which is represented by the recent approval of three CAR therapies for B cell malignancies. Understanding the biology of this unique cellular immunotherapy will be important to improve efficacy and reduce toxicity. Our study demonstrates that enhancement of CAR T function by 4-1BB requires TRAF1 and TRAF3 to optimally activate NF-κB. Furthermore, our strategy of co-expressing a 4-1BB based CAR and TRAF proteins enhanced CAR T cell viability, proliferation and cytotoxicity. Overexpressing TRAF proteins could also benefit CD28-based CAR T cells since some TRAFs interact with CD28 (Xie P, et al. J Immunol. 2011 186(1):143-55). Considering the antagonistic roles of both TRAF1 and TRAF2 in the NF-κB pathway and for the role of TRAF3 in both 4-1BB and CD28 co-stimulation it will be necessary to evaluate the impact of individual TRAFs in CARs with different co-stimulatory domains to identify how they regulate optimal CAR T cell signaling and function.

TABLE 1

Probesets increased in m19z and m1928z vs. m19-musBBz CART cells

| Probeset ID | Gene Symbol | Fold-Change | Probeset ID | Gene Symbol | Fold-Change |
| --- | --- | --- | --- | --- | --- |
| 1418679_at | Gzmf | 8.0 | 1422601_at | Serpinb9 | 2.9 |
| 1422668_at | Serpinb9b | 7.8 | 1417523_at | Plek | 2.9 |
| 1419561_at | Ccl3 | 6.9 | 1450495_a_at | Klrk1 | 2.9 |
| 1450297_at | Il6 | 6.8 | 1423101_at | Paqr4 | 2.9 |
| 1416842_at | Gstm5 | 6.5 | 1431724_a_at | P2ry12 | 2.9 |
| 1420789_at | Klra5 | 5.1 | 1422887_a_at | Ctbp2 | 2.8 |
| 1448390_a_at | Dhrs3 | 4.9 | 1424356_a_at | Metrnl | 2.8 |
| 1453060_at | Rgs8 | 4.9 | 1417434_at | Gpd2 | 2.7 |
| 1449835_at | Pdcd1 | 4.8 | 1421188_at | Ccr2 | 2.7 |
| 1448942_at | Gng11 | 4.8 | 1424711_at | Tmem2 | 2.7 |
| 1422867_at | Gzmg | 4.8 | 1420343_at | Gzmd | 2.6 |
| 1450650_at | Myo10 | 4.8 | 1448328_at | Sh3bp2 | 2.6 |
| 1416714_at | Irf8 | 4.7 | 1419814_s_at | S100a1 | 2.6 |
| 1416666_at | Serpine2 | 4.6 | 1423543_at | Swap70 | 2.6 |
| 1420398_at | Rgs18 | 4.6 | 1421186_at | Ccr2 | 2.6 |

TABLE 1-continued

Probesets increased in m19z and m1928z vs. m19-musBBz CART cells

| Probeset ID | Gene Symbol | Fold-Change | Probeset ID | Gene Symbol | Fold-Change |
|---|---|---|---|---|---|
| 1448452_at | Irf8 | 4.5 | 1450871_a_at | Bcat1 | 2.6 |
| 1423231_at | Nrgn | 4.4 | 1420344_x_at | Gzmd | 2.6 |
| 1423319_at | Hhex | 4.4 | 1420388_at | Prss12 | 2.6 |
| 1422544_at | Myo10 | 4.3 | 1427985_at | Spin4 | 2.6 |
| 1426318_at | Serpinb1b | 4.3 | 1449852_a_at | Ehd4 | 2.5 |
| 1425947_at | Ifng | 4.3 | 1436584_at | Spry2 | 2.5 |
| 1449991_at | Cd244 | 4.1 | 1448562_at | Upp1 | 2.5 |
| 1451862_a_at | Prf1 | 4.1 | 1428077_at | Tmem163 | 2.5 |
| 1420788_at | Klrg1 | 4.1 | 1422880_at | Sypl | 2.5 |
| 1451584_at | Havcr2 | 4.1 | 1449799_s_at | Pkp2 | 2.5 |
| 1424099_at | Gpx8 | 4.0 | 1422879_at | Sypl | 2.4 |
| 1426169_a_at | Lat2 | 4.0 | 1450140_a_at | Cdkn2a | 2.4 |
| 1422804_at | Serpinb6b | 4.0 | 1449164_at | Cd68 | 2.4 |
| 1449570_at | Klrb1c | 3.9 | 1449383_at | Adssl1 | 2.4 |
| 1450750_a_at | Nr4a2 | 3.9 | 1417753_at | Pkd2 | 2.4 |
| 1448749_at | Plek | 3.8 | 1420159_at | Myo1e | 2.4 |
| 1449965_at | Mcpt8 | 3.8 | 1422881_s_at | Sypl | 2.4 |
| 1449254_at | Spp1 | 3.7 | 1417588_at | Galnt3 | 2.4 |
| 1426063_a_at | Gem | 3.7 | 1421317_x_at | Myb | 2.4 |
| 1428034_a_at | Tnfrsf9 | 3.7 | 1450646_at | Cyp51 | 2.3 |
| 1422837_at | Scel | 3.7 | 1422734_at | Myb | 2.3 |
| 1417335_at | Sult2b1 | 3.6 | 1432459_a_at | Zbtb32 | 2.3 |
| 1450171_x_at | Gzme | 3.6 | 1450194_at | Myb | 2.3 |
| 1418317_at | Lhx2 | 3.6 | 1419091_a_at | Anxa2 | 2.3 |
| 1421256_at | Gzmc | 3.6 | 1417178_at | Gipc2 | 2.3 |
| 1451021_a_at | Klf5 | 3.6 | 1434705_at | Ctbp2 | 2.3 |
| 1433741_at | Cd38 | 3.5 | 1423596_at | Nek6 | 2.3 |
| 1434025_at | — | 3.4 | 1426334_a_at | Bcl2l11 | 2.3 |
| 1428379_at | Slc17a6 | 3.4 | 1417400_at | Rai14 | 2.3 |
| 1417749_a_at | Tjp1 | 3.4 | 1452011_a_at | Uxs1 | 2.2 |
| 1425470_at | LOC105247125 | 3.4 | 1422255_at | Kcna4 | 2.2 |
| 1421688_a_at | Ccl1 | 3.4 | 1418026_at | Exo1 | 2.2 |
| 1421227_at | Gzmd | 3.3 | 1424966_at | Tmem40 | 2.2 |
| 1426037_a_at | Rgs16 | 3.3 | 1432410_a_at | Bmp7 | 2.2 |
| 1449888_at | Epas1 | 3.3 | 1425785_a_at | Txk | 2.2 |
| 1418610_at | Slc17a6 | 3.3 | 1416304_at | Litaf | 2.2 |
| 1448748_at | Plek | 3.2 | 1416303_at | Litaf | 2.2 |
| 1418340_at | Fcer1g | 3.2 | 1431422_a_at | Dusp14 | 2.2 |
| 1425125_at | Oit3 | 3.2 | 1451122_at | Gm38481 | 2.2 |
| 1460469_at | Tnfrsf9 | 3.2 | 1450131_a_at | Bspry | 2.2 |
| 1424588_at | Srgap3 | 3.1 | 1451318_a_at | Lyn | 2.1 |
| 1417936_at | Ccl9 | 3.1 | 1426001_at | Eomes | 2.1 |
| 1449856_at | Rgs18 | 3.1 | 1421048_a_at | Ypel1 | 2.1 |
| 1426120_a_at | Cd244 | 3.1 | 1431782_s_at | Ypel1 | 2.1 |
| 1426808_at | Lgals3 | 3.1 | 1422477_at | Cables1 | 2.1 |
| 1419647_a_at | Ier3 | 3.1 | 1434427_a_at | Rnf157 | 2.1 |
| 1452492_a_at | Slc37a2 | 3.0 | 1426171_x_at | Klra7 | 2.1 |
| 1416431_at | Tubb6 | 3.0 | 1435086_s_at | Klhdc2 | 2.1 |
| 1419412_at | Xcl1 | 3.0 | 1422557_s_at | Mt1 | 2.1 |
| 1418910_at | Bmp7 | 2.9 | 1423804_a_at | Gm38481 | 2.1 |
| 1450136_at | Cd38 | 2.9 | 1430394_a_at | Abcb9 | 2.1 |
| 1426911_at | Dsc2 | 2.9 | 1450290_at | Pdcd1lg2 | 2.0 |
| 1451458_at | Tmem2 | 2.9 | | | |

TABLE 2

Probesets increased in m19-musBBz vs. m19z and m1928z CAR T cells

| Probeset ID | Gene Symbol | Fold-Change | Probeset ID | Gene Symbol | Fold-Change |
|---|---|---|---|---|---|
| 1423100_at | Fos | 14.0 | 1453678_at | Mbd1 | 2.5 |
| 1448830_at | Dusp1 | 4.6 | 1449049_at | Tlr1 | 2.5 |
| 1423756_s_at | Igfbp4 | 4.3 | 1419695_at | St8sia1 | 2.4 |
| 1459884_at | Cox7c | 4.1 | 1437658_a_at | Snord22 | 2.4 |
| 1433863_at | Btf3 | 4.0 | 1419418_a_at | Morc1 | 2.4 |
| 1452519_a_at | Zfp36 | 4.0 | 1448656_at | Cacnb3 | 2.4 |
| 1459885_s_at | Cox7c | 3.9 | 1456266_at | Gm5481 | 2.4 |
| 1436882_at | Ubl5 | 3.7 | 1436686_at | Zfp706 | 2.4 |
| 1427351_s_at | Ighm | 3.6 | 1456603_at | Fam101b | 2.3 |
| 1417394_at | Klf4 | 3.6 | 1442745_x_at | Gm39971 | 2.3 |
| 1428585_at | Actn1 | 3.5 | 1448325_at | Ppp1r15a | 2.3 |
| 1433471_at | Tcf7 | 3.4 | 1425919_at | Ndufa12 | 2.3 |

TABLE 2-continued

Probesets increased in m19-musBBz vs. m19z and m1928z CAR T cells

| Probeset ID | Gene Symbol | Fold-Change | Probeset ID | Gene Symbol | Fold-Change |
|---|---|---|---|---|---|
| 1437405_a_at | Igfbp4 | 3.4 | 1442744_at | Gm39971 | 2.3 |
| 1416107_at | Nsg2 | 3.4 | 1419694_at | St8sia1 | 2.3 |
| 1420161_at | LOC105245295 | 3.3 | 1441023_at | Eif2s2 | 2.3 |
| 1425086_a_at | Slamf6 | 3.3 | 1418741_at | Itgb7 | 2.3 |
| 1427329_at | Ighm | 3.2 | 1456386_at | Rbm39 | 2.3 |
| 1428283_at | Cyp2s1 | 3.1 | 1448327_at | Actn2 | 2.3 |
| 1435290_x_at | H2-Aa | 3.1 | 1420088_at | Nfkbia | 2.3 |
| 1450461_at | Tcf7 | 3.1 | 1451731_at | Abca3 | 2.3 |
| 1422134_at | Fosb | 3.0 | 1421214_at | Cmah | 2.3 |
| 1448890_at | Klf2 | 2.9 | 1449815_a_at | Ssbp2 | 2.3 |
| 1449216_at | Itgae | 2.9 | 1427615_at | Itga4 | 2.3 |
| 1438076_at | Gm5481 | 2.9 | 1446147_at | Gm39971 | 2.2 |
| 1417409_at | Jun | 2.9 | 1418128_at | Adcy6 | 2.2 |
| 1442494_at | C79242 | 2.8 | 1438211_s_at | Dbp | 2.2 |
| 1428357_at | Tdrp | 2.7 | 1436871_at | Srsf7 | 2.2 |
| 1423555_a_at | Ifi44 | 2.6 | 1437390_x_at | Stx1a | 2.2 |
| 1426640_s_at | Trib2 | 2.6 | 1435316_at | Psma6 | 2.2 |
| 1449731_s_at | Nfkbia | 2.6 | 1438675_at | Sfswap | 2.2 |
| 1449025_at | Ifit3 | 2.6 | 1427335_at | Tmem260 | 2.2 |
| 1421194_at | Itga4 | 2.6 | 1446148_x_at | Gm39971 | 2.2 |
| 1448306_at | Nfkbia | 2.5 | 1454703_x_at | Snhg1 | 2.2 |
| 1420659_at | Slamf6 | 2.5 | 1449858_at | Cd86 | 2.2 |
| 1438398_at | Rbm39 | 2.5 | 1448420_a_at | Fbxl12 | 2.1 |

TABLE 3

Probesets differentially expressed in m19z vs. m19-musBBz CAR T cells

| Probeset ID | Gene Symbol | Fold-Change | Probeset ID | Gene Symbol | Fold-Change |
|---|---|---|---|---|---|
| 1437279_x_at | Sdc1 | 9.1 | 1449903_at | Crtam | 2.3 |
| 1426260_a_at | Ugt1a1 | 5.2 | 1417300_at | Smpdl3b | 2.3 |
| 1425471_x_at | LOC105247125 | 5.0 | 1452565_x_at | — | 2.3 |
| 1425538_x_at | Ceacam1 | 4.8 | 1426541_a_at | Endod1 | 2.3 |
| 1418547_at | Tfpi2 | 4.5 | 1423418_at | Fdps | 2.2 |
| 1415943_at | Sdc1 | 4.5 | 1422748_at | Zeb2 | 2.2 |
| 1427038_at | Penk | 4.5 | 1449184_at | Pglyrp1 | 2.2 |
| 1420421_s_at | Klrb1b | 4.2 | 1452661_at | Tfrc | 2.2 |
| 1426261_s_at | Ugt1a1 | 4.1 | 1424650_at | Pdia5 | 2.2 |
| 1451446_at | Antxr1 | 3.8 | 1417162_at | Tmbim1 | 2.2 |
| 1418186_at | Gstt1 | 3.7 | 1422123_s_at | Ceacam1 | 2.2 |
| 1448898_at | Ccl9 | 3.5 | 1422533_at | Cyp51 | 2.2 |
| 1421578_at | Ccl4 | 3.4 | 1460678_at | Klhdc2 | 2.2 |
| 1426182_a_at | Klrc1 | 3.3 | 1460682_s_at | Ceacam1 | 2.2 |
| 1425923_at | Mycn | 3.3 | 1459903_at | Sema7a | 2.2 |
| 1455423_at | Khdc1a | 3.3 | 1452404_at | Phactr2 | 2.2 |
| 1452367_at | Coro2a | 3.2 | 1437330_at | Lrrk1 | 2.1 |
| 1416156_at | Vcl | 3.1 | 1423590_at | Napsa | 2.1 |
| 1455265_a_at | Rgs16 | 3.1 | 1426542_at | Endod1 | 2.1 |
| 1429159_at | Itih5 | 3.1 | 1448752_at | Car2 | 2.1 |
| 1428574_a_at | Chn2 | 3.0 | 1454904_at | Mtm1 | 2.1 |
| 1451452_at | Rgs16 | 3.0 | 1418206_at | Sdf2l1 | 2.1 |
| 1425675_s_at | Ceacam1 | 2.9 | 1438165_x_at | Vat1 | 2.1 |
| 1418084_at | Nrp1 | 2.8 | 1417100_at | Cd320 | 2.1 |
| 1427630_x_at | Ceacam1 | 2.8 | 1418401_a_at | Dusp16 | 2.1 |
| 1438312_s_at | Ltbp3 | 2.8 | 1427005_at | Plk2 | 2.1 |
| 1425436_x_at | Klra3 | 2.8 | 1421933_at | Cbx5 | 2.1 |
| 1429183_at | Pkp2 | 2.7 | 1426543_x_at | Endod1 | 2.1 |
| 1425005_at | Klrc1 | 2.7 | 1450651_at | Myo10 | 2.1 |
| 1422967_a_at | Tfrc | 2.7 | 1449911_at | Lag3 | 2.1 |
| 1448944_at | Nrp1 | 2.7 | 1425469_a_at | LOC105247125 | 2.1 |
| 1418879_at | Fam110c | 2.6 | 1433443_a_at | Hmgcs1 | 2.0 |
| 1430419_at | — | 2.6 | 1428942_at | Mt2 | 2.0 |
| 1424783_a_at | Ugt1a1 | 2.6 | 1452539_a_at | Cd247 | 2.0 |
| 1415964_at | Scd1 | 2.6 | 1423413_at | Ndrg1 | 2.0 |
| 1450494_x_at | Ceacam1 | 2.6 | 1425179_at | Shmt1 | 2.0 |
| 1450790_at | Tg | 2.6 | 1415811_at | Uhrf1 | 2.0 |
| X00686_5_at | — | 2.6 | 1418350_at | Hbegf | 2.0 |
| 1425745_a_at | Tacc2 | 2.6 | 1449152_at | Cdkn2b | 2.0 |
| 1428573_at | Chn2 | 2.6 | 1460353_at | Ndc1 | 2.0 |
| 1422067_at | Klrb1b | 2.5 | 1449482_at | Hist3h2ba | −2.0 |
| 1418449_at | Lad1 | 2.5 | 1420404_at | Cd86 | −2.0 |
| 1426300_at | Alcam | 2.5 | 1423169_at | Taf7 | −2.0 |

TABLE 3-continued

Probesets differentially expressed in m19z vs. m19-musBBz CAR T cells

| Probeset ID | Gene Symbol | Fold-Change | Probeset ID | Gene Symbol | Fold-Change |
|---|---|---|---|---|---|
| 1426472_at | Zfp52 | 2.5 | 1425518_at | Rapgef4 | -2.2 |
| 1449481_at | Slc25a13 | 2.4 | 1420805_at | Myl10 | -2.2 |
| 1418049_at | Ltbp3 | 2.4 | 1436677_at | 1810032O08Rik | -2.3 |
| 1448943_at | Nrp1 | 2.4 | 1424800_at | Enah | -2.3 |
| X57349_5_at | Tfrc | 2.4 | 1417483_at | Nfkbiz | -2.4 |
| 1450296_at | Klrb1a | 2.3 | 1417928_at | Pdlim4 | -2.4 |
| 1422639_at | Calcb | 2.3 | | | |

TABLE 4

Probesets differentially expressed in m1928z vs. m19-musBBz CAR T cells

| Probeset ID | Gene Symbol | Fold-Change | Probeset ID | Gene Symbol | Fold-Change |
|---|---|---|---|---|---|
| 1449280_at | Esm1 | 5.2 | 1423851_a_at | Shisa2 | 2.1 |
| 1422824_s_at | Eps8 | 3.8 | 1456098_a_at | Elmo2 | 2.1 |
| 1439036_a_at | Atp1b1 | 3.6 | 1420407_at | Ltb4r1 | 2.1 |
| 1419594_at | Ctsg | 3.6 | 1451944_a_at | Tnfsf11 | 2.1 |
| 1422823_at | Eps8 | 3.3 | 1452478_at | Alpk2 | 2.1 |
| 1426680_at | Sepn1 | 3.1 | 1416846_a_at | Pdzrn3 | 2.1 |
| 1421654_a_at | Lmna | 3.0 | 1418685_at | Tirap | 2.1 |
| 1420463_at | Clnk | 2.9 | 1421642_a_at | Cysltr2 | 2.1 |
| 1422280_at | Gzmk | 2.9 | 1421525_a_at | Naip5 | 2.1 |
| 1428572_at | Basp1 | 2.8 | 1422041_at | Pilrb1 | 2.0 |
| 1425503_at | Gcnt2 | 2.8 | 1425733_a_at | Eps8 | 2.0 |
| 1434868_at | 4933431E20Ri | 2.7 | 1418057_at | Tiam1 | 2.0 |
| 1423530_at | Stk32c | 2.7 | 1460192_at | Osbpl1a | 2.0 |
| 1450989_at | Tdgf1 | 2.7 | 1453915_a_at | Slc37a3 | 2.0 |
| 1427918_a_at | Rhoq | 2.7 | 1418943_at | Zak | 2.0 |
| 1424089_a_at | Tcf4 | 2.7 | 1455570_x_at | Cnn3 | -2.0 |
| 1434148_at | Tcf4 | 2.6 | 1450484_a_at | Cmpk2 | -2.0 |
| 1428197_at | Tspan9 | 2.6 | 1420089_at | Nfkbia | -2.0 |
| 1450792_at | Tyrobp | 2.6 | 1436836_x_at | Cnn3 | -2.0 |
| 1448590_at | Col6a1 | 2.6 | 1424378_at | Ldlrap1 | -2.0 |
| 1451867_x_at | Arhgap6 | 2.5 | 1426043_a_at | Capn3 | -2.0 |
| 1431226_a_at | Fndc4 | 2.5 | 1425065_at | Oas2 | -2.0 |
| 1419184_a_at | Fhl2 | 2.5 | 1438397_at | Rbm39 | -2.0 |
| 1423852_at | Shisa2 | 2.4 | 1421922_at | Sh3bp5 | -2.1 |
| 1415973_at | Marcks | 2.4 | 1419135_at | Ltb | -2.1 |
| 1430826_s_at | Gcnt2 | 2.4 | 1438215_at | Srsf3 | -2.1 |
| 1449170_at | Piwil2 | 2.4 | 1455220_at | Frat2 | -2.1 |
| 1456700_x_at | Marcks | 2.4 | 1436994_a_at | Hist1h1c | -2.1 |
| 1416318_at | Serpinb1a | 2.4 | 1426997_at | Thra | -2.1 |
| 1449456_at | Cma1 | 2.4 | 1431388_at | Mphosph10 | -2.1 |
| 1451733_at | Gcnt2 | 2.4 | 1450783_at | Ifit1 | -2.1 |
| 1419083_at | Tnfsf11 | 2.3 | 1417395_at | Klf4 | -2.1 |
| 1455901_at | Chpt1 | 2.3 | 1452844_at | Pou6f1 | -2.1 |
| 1448730_at | Cpa3 | 2.3 | 1450648_s_at | H2-Ab1 | -2.1 |
| 1450344_a_at | Ptger3 | 2.3 | 1433428_x_at | Tgm2 | -2.1 |
| 1418260_at | Hunk | 2.3 | 1422010_at | Tlr7 | -2.1 |
| 1415972_at | Marcks | 2.3 | 1436364_x_at | Nfix | -2.1 |
| 1438169_a_at | Frmd4b | 2.3 | 1427313_at | Ptgir | -2.1 |
| 1435172_at | Eomes | 2.3 | 1436032_at | — | -2.1 |
| 1420364_at | Gpr87 | 2.3 | 1437277_x_at | Tgm2 | -2.1 |
| 1416724_x_at | Tcf4 | 2.3 | 1425702_a_at | Enpp5 | -2.1 |
| 1450764_at | Aoah | 2.3 | 1438674_a_at | Sfswap | -2.2 |
| 1418912_at | Plxdc2 | 2.3 | 1421840_at | Abca1 | -2.2 |
| 1448460_at | Acvrl | 2.2 | 1451767_at | Ncf1 | -2.2 |
| 1421415_s_at | Gcnt2 | 2.2 | 1437513_a_at | Serinc1 | -2.2 |
| 1417163_at | Dusp10 | 2.2 | 1450336_at | Setd1a | -2.2 |
| 1448798_at | Eps8l3 | 2.2 | 1425570_at | Slamf1 | -2.2 |
| 1417777_at | Ptgr1 | 2.2 | 1434062_at | Rabgap1l | -2.2 |
| 1448233_at | Prnp | 2.2 | 1420342_at | Gdap10 | -2.2 |
| 1416723_at | Tcf4 | 2.2 | 1421923_at | Sh3bp5 | -2.3 |
| 1424733_at | P2ry14 | 2.2 | 1427511_at | — | -2.3 |
| 1425137_a_at | H2-Q10 | 2.2 | 1460251_at | Fas | -2.3 |
| 1435870_at | Chpt1 | 2.1 | 1425519_a_at | Cd74 | -2.3 |
| 1425452_s_at | Fam84a | 2.1 | 1425569_a_at | Slamf1 | -2.4 |
| 1433558_at | Dab2ip | 2.1 | 1418174_at | Dbp | -2.4 |
| 1434149_at | Tcf4 | 2.1 | 1451542_at | Ssbp2 | -2.5 |
| 1417421_at | S100a1 | 2.1 | 1452416_at | Il6ra | -2.5 |
| 1433575_at | Sox4 | 2.1 | 1454675_at | Thra | -2.5 |
| 1417714_x_at | Hba-al | 2.1 | 1450048_a_at | Idh2 | -2.5 |

TABLE 4-continued

Probesets differentially expressed in m1928z vs. m19-musBBz CAR T cells

| Probeset ID | Gene Symbol | Fold-Change | Probeset ID | Gene Symbol | Fold-Change |
|---|---|---|---|---|---|
| 1416129_at | Errfi1 | 2.1 | 1418398_a_at | Tspan32 | −2.5 |
| 1435446_a_at | Chpt1 | 2.1 | 1422231_a_at | Tnfrsf25 | −2.6 |
| 1449270_at | Plxdc2 | 2.1 | 1418126_at | Ccl5 | −2.6 |
| 1450744_at | Ell2 | 2.1 | 1423466_at | Ccr7 | −2.7 |
| 1456028_x_at | Marcks | 2.1 | 1419696_at | Cd4 | −2.8 |
| 1415971_at | Marcks | 2.1 | 1436363_a_at | Nfix | −3.0 |
| 1421187_at | Ccr2 | 2.1 | 1416330_at | Cd81 | −3.6 |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A chimeric antigen receptor (CAR) polypeptide, comprising a tumor associated antigen (TAA) binding domain, a transmembrane domain, an intracellular signaling domain, and a co-stimulatory signaling region, wherein the co-stimulatory signaling region comprises a cytoplasmic domain of a mutated 41BB comprising the amino acid sequence KRGRKKLLYIFKQPFMRPVQTTX$_1$X$_2$X$_3$X$_4$GCSCRFP X$_5$X$_6$X$_7$X$_8$GGCEL (SEQ ID NO:23), wherein X$_1$ is not Gln, wherein X$_2$ is not Glu, wherein X$_3$ is not Glu, wherein X$_4$ is not Asp, wherein X$_5$ is not Glu, wherein X$_6$ is not Glu, wherein X$_7$ is not Glu, wherein X$_8$ is not Glu, or any combination thereof.

2. The polypeptide of claim 1, wherein the co-stimulatory signaling region comprises two cytoplasmic domains of the mutated 41 BB.

3. The polypeptide of claim 2, wherein the 41BB comprises an amino acid sequence KRGRKKLLYIFKQPFMRPVQTTX$_1$X$_2$X$_3$X$_4$GCSCRFP X$_5$X$_6$X$_7$X$_8$GGCELKRGRKKLLYIFKQPFMR PVQTTX$_9$X$_{10}$X$_{11}$X$_{12}$GCSCRFPX$_{13}$X$_{14}$X$_{15}$X$_{16}$GGCEL (SEQ ID NO:24), wherein X$_1$ is not Gln, wherein X$_2$ is not Glu, wherein X$_3$ is not Glu, wherein X$_4$ is not Asp, wherein X$_5$ is not Glu, wherein X$_6$ is not Glu, wherein X$_7$ is not Glu, wherein X$_8$ is not Glu, wherein X$_9$ is not Gln, wherein X$_{10}$ is not Glu, wherein X$_{11}$ is not Glu, wherein X$_{12}$ is not Asp, wherein X$_{13}$ is not Glu, wherein X$_{14}$ is not Glu, wherein X$_{15}$ is not Glu, wherein X$_{18}$ is not Glu, or any combination thereof.

4. The polypeptide of claim 1, wherein the CAR polypeptide is defined by the formula:

SP-TAA-HG-TM-CSR-ISD; or

SP-TAA-HG-TM-ISD-CSR wherein "SP" represents a signal peptide,
wherein "TAA" represents a tumor associated antigen-binding region,
wherein "HG" represents an optional hinge domain,
wherein "TM" represents a transmembrane domain,
wherein "CSR" represents the co-stimulatory signaling region,
wherein "ISD" represents an intracellular signaling domain, and
wherein "-" represents a bivalent linker.

5. The polypeptide of claim 1, wherein the intracellular signaling domain comprises a CD3 zeta (CD3ζ) signaling domain.

6. The polypeptide of claim 1, wherein the 41BB comprises an amino acid sequence selected from SEQ ID NOS: 2-4, 6-19, or 20.

7. The polypeptide of claim 1, wherein the 41 BB comprises an amino acid sequence KRGRKKLLYIFKQPFMRPVQTTQEEDGCSCRFPX$_5$X$_6$ X$_7$X$_8$GGCEL (SEQ ID NO:22), wherein X$_5$ is not Glu, wherein X$_6$ is not Glu, wherein X$_7$ is not Glu, wherein X$_8$ is not Glu, or any combination thereof.

8. The polypeptide of claim 1, further comprising a cytoplasmic domain of CD28 lacking a YMNM subdomain, lacking a PRRP subdomain, and/or lacking a PYAP subdomain.

9. An isolated nucleic acid sequence encoding the polypeptide of claim 1.

10. A vector comprising the isolated nucleic acid sequence of claim 9.

11. An immune effector cell comprising the vector of claim 10.

12. The cell of claim 11, wherein the immune effector cell is selected from the group consisting of an αβT cell, γδT cell, a Natural Killer (NK) cells, a Natural Killer T (NKT) cell, an innate lymphoid cell (ILC), a cytokine induced killer (CIK) cell, a cytotoxic T lymphocyte (CTL), a lymphokine activated killer (LAK) cell, a regulatory T cell, and any combination thereof.

13. The cell of claim 12, wherein the immune effector cell exhibits an anti-tumor immunity when the antigen binding domain of the CAR binds to TAA.

14. An immune effector cell, co-expressing the chimeric antigen receptor (CAR) polypeptide of claim 1 and one or more exogenous TRAF2 and/or TRAF3 proteins.

15. A method of providing an anti-tumor immunity in a subject with a TAA-expressing cancer, the method comprising administering to the subject an effective amount of the immune effector cell of claim 14, thereby providing an anti-tumor immunity in the subject.

16. The method of claim 15, wherein the immune effector cell is selected from the group consisting of a T cell, a Natural Killer (NK) cell, a cytotoxic T lymphocyte (CTL), and a regulatory T cell.

17. The method of claim 15, further comprising administering to the subject a checkpoint inhibitor.

18. The method of claim 17, wherein the checkpoint inhibitor comprises an anti-PD-1 antibody, anti-PD-L1 antibody, anti-CTLA-4 antibody, or a combination thereof.

* * * * *